United States Patent
Colletti et al.

(10) Patent No.: US 8,455,520 B2
(45) Date of Patent: Jun. 4, 2013

(54) SOLUBLE EPOXIDE HYDROLASE INHIBITORS, COMPOSITIONS CONTAINING SUCH COMPOUNDS AND METHODS OF TREATMENT

(75) Inventors: Steven L. Colletti, Princeton Junction, NJ (US); Hong Shen, West Windsor, NJ (US); Fa-Xiang Ding, Staten Island, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 596 days.

(21) Appl. No.: 12/668,494

(22) PCT Filed: Jul. 11, 2008

(86) PCT No.: PCT/US2008/008693
§ 371 (c)(1),
(2), (4) Date: Jan. 11, 2010

(87) PCT Pub. No.: WO2009/011872
PCT Pub. Date: Jan. 22, 2009

(65) Prior Publication Data
US 2010/0197691 A1 Aug. 5, 2010

Related U.S. Application Data

(60) Provisional application No. 60/959,814, filed on Jul. 17, 2007.

(51) Int. Cl.
| | |
|---|---|
| A61K 31/4985 | (2006.01) |
| A61K 31/4725 | (2006.01) |
| A61K 31/4545 | (2006.01) |
| A61K 31/454 | (2006.01) |
| A61K 31/451 | (2006.01) |
| A61K 31/445 | (2006.01) |
| C07D 417/12 | (2006.01) |
| C07D 413/12 | (2006.01) |
| C07D 413/04 | (2006.01) |
| C07D 401/12 | (2006.01) |
| C07D 401/06 | (2006.01) |
| C07D 401/04 | (2006.01) |
| C07D 211/60 | (2006.01) |
| C07D 211/56 | (2006.01) |
| C07D 211/62 | (2006.01) |
| C07D 211/34 | (2006.01) |
| C07D 211/22 | (2006.01) |
| C07D 211/16 | (2006.01) |

(52) U.S. Cl.
USPC .......... 514/330; 514/326; 514/321; 514/323; 514/322; 514/318; 514/249; 544/353; 546/146; 546/194; 546/198; 546/199; 546/201; 546/205; 546/211; 546/209; 546/210; 546/226

(58) Field of Classification Search
USPC .............. 514/318, 323, 322, 326, 330, 249, 514/321; 546/194, 199, 198, 201, 209, 210, 546/226, 146, 205, 211; 544/237, 353
See application file for complete search history.

(56) References Cited

U.S. PATENT DOCUMENTS

| | | | |
|---|---|---|---|
| 4,707,487 | A | 11/1987 | Arrang et al. |
| 5,955,496 | A | 9/1999 | Hammock et al. |
| 6,150,415 | A | 11/2000 | Hammock et al. |
| 6,890,925 | B2 | 5/2005 | Ingraham et al. |
| 2003/0022097 | A1 | 1/2003 | Malik et al. |
| 2005/0059665 | A1 | 3/2005 | Khanapure et al. |
| 2005/0277674 | A1 | 12/2005 | Hinze et al. |
| 2006/0167052 | A1 | 7/2006 | Ikeura et al. |

FOREIGN PATENT DOCUMENTS

| | | |
|---|---|---|
| CA | 2 145 000 | 5/2002 |
| EP | 0 197 840 A1 | 10/1986 |
| EP | 0 673 928 A1 | 9/1995 |
| EP | 0 625 507 B1 | 7/1997 |
| WO | 97/38665 | 10/1997 |
| WO | 00/23060 | 4/2000 |
| WO | 00/35877 A1 | 6/2000 |
| WO | 01/14328 A2 | 3/2001 |
| WO | 01/85714 A1 | 11/2001 |
| WO | WO 0185714 A1 * | 11/2001 |
| WO | 03/049741 A1 | 6/2003 |

(Continued)

OTHER PUBLICATIONS

Dennedy et al. Medicine, 2010, 38, 610-617.*
Zhang et al. European Journal of Pharmacology 2011, 654, 68-74.*
Vogel et al., "Endogenous Role of Microsomal Epoxide Hydrolase", Eur. J. Biochem., vol. 126, pp. 425-431 (1982).
Schladt et al., "Distribution and Inducibility of Cytosolic Epoxide Hydrolase in Male Sprague-Dawley Rats", Biochemical Pharmacology, vol. 35, No. 19, pp. 3309-3316 (1986).
Seidegard et al., "Measurement and Characterization of Membrane-bound and Soluble Epoxide Hyrdolase Activities in Resting Mononuclear Leukocytes from Human Blood", Cancer Research, vol. 44, pp. 3654-3660 (1984).

(Continued)

Primary Examiner — Joseph Kosack
Assistant Examiner — Matthew Coughlin
(74) Attorney, Agent, or Firm — Anna L. Cocuzzo; Richard C. Billups; John C. Todaro

(57) ABSTRACT

Compounds of the Formula: (I) as well as pharmaceutically acceptable salts and hydrates thereof, that are useful for treating hypertension, diabetes, inflammation, atherosclerosis, pain, and the like are disclosed. Pharmaceutical compositions and methods of use are also included.

(I)

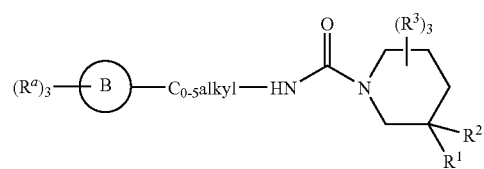

21 Claims, No Drawings

FOREIGN PATENT DOCUMENTS

| | | |
|---|---|---|
| WO | 03/101964 A1 | 12/2003 |
| WO | 2004/043949 A1 | 5/2004 |
| WO | 2004/048334 A1 | 6/2004 |
| WO | 2005/051390 A1 | 6/2005 |
| WO | 2005/081954 A2 | 9/2005 |
| WO | 2006/115285 A1 | 11/2006 |
| WO | 2006/136606 A2 | 12/2006 |
| WO | 2006/137350 A1 | 12/2006 |
| WO | 2007/009001 A1 | 1/2007 |
| WO | 2007/035478 A2 | 3/2007 |
| WO | 2007/134958 | 11/2007 |

OTHER PUBLICATIONS

Kim et al., "Reciprocal Relationships Between Insulin Resistence and Endothelial Dysfunction", Circulation, vol. 113, pp. 1888-1904 (2006).

Imig et al., "Soluble Epoxide Hydrolase Inhibition Lowers Arterial Blood Pressure in Angiotensin II Hypertension", Hypertension, vol. 39, Part 2, pp. 690-694 (2002).

Node et al., "Anti-inflammatory Properties of Cytochrome P450 Epoxygenase-Derived Eicosanoids", Science, vol. 285(5431), pp. 1276-1279 (1999).

Campbell, "New role for epoxyeicosatrienoic acids as anti-inflammatory", TIPS, vol. 21, pp. 125-127 (2000).

Zeldin et al., "Reply: cytochrome P450-derived eicosanoids and the vascular wall", TIPS, vol. 21, pp. 127-128 (2000).

Kessler et al., "Proinflammatory Mediators Chronically Downregulate the Formation of the Endothelium-Derived Hyperpolarizing Factor in Arteries Via a Nitric Oxide/Cyclic GMP-Dependent Mechanism", Circulation, vol. 99, pp. 1878-1884 (1999).

Morisseau et al., "Potent Urea and Carbamate Inhibitors of Soluble Epoxide Hydrolases", Proc. Natl. Acad. Science, vol. 96, pp. 8849-8854 (1999).

Miyamoto et al., "Inhibition of Epoxide Hydrolases and Glutathione S-Transferases 2-, 3-, and 4-Substituted Derivatives of 4'-Phenylchalcoem and Its Oxide", Archives of Biochemistry and Biophysics, vol. 254, No. 1, pp. 203-213 (1987).

Dietze et al., "Inhibition of Cytosolic Epoxide Hydrolase by trans-3-Phenylglycidols", Biochemical Pharmacology, vol. 42, No. 6, pp. 1163-1175 (1991).

Dietze et al., Inhibition of Epoxide Hydrolase From Human, Monkey, Bovine, Rabbit and Murine Liver by Trans-3-Phenylglycidols, Comp. Biochem. Physiol., vol. 104B, pp. 309-314 (1993).

Schmelzer et al., "Enhancement of Antinociciption by Coadministration of Nonsteroidal Anti-Inflammatory Drugs and Soluble Epoxide Hydrolase Inhibitors", PNAS, vol. 103, No. 37, pp. 13646-13651 (2006).

Zeldin, "Epoxygenase Pathways of Arachidonic Acid Metabolism", The J. of Biological Chemistry, vol. 276, No. 39, pp. 36059-36062 (2001).

Spector et al., "Epoxyeicosatrienoic Acids (EETs): Metabolism and Biochemical Function", Progress in Lipid Research, vol. 43, pp. 55-90 (2004).

Newman et al., "Epoxide Hydrolases: their roles and interactions with lipid metabolism", Progress in Lipid Research, vol. 44, pp. 1-51 (2005).

* cited by examiner

SOLUBLE EPOXIDE HYDROLASE INHIBITORS, COMPOSITIONS CONTAINING SUCH COMPOUNDS AND METHODS OF TREATMENT

REFERENCE TO RELATED APPLICATIONS

This application is a U.S. National Phase application under 35 U.S.C. §371 of PCT Application No. PCT/US2008/008693, filed Jul. 11, 2008, which published as WO 2009/011872 on Jan. 22, 2009, and claims priority under 35 U.S.C. §119 from U.S. Provisional Application No. 60/959,814, filed Jul. 17, 2007.

BACKGROUND OF THE INVENTION

The present invention relates to trisubstituted urea compounds possessing soluble epoxide hydrolase (sEH) inhibitory activity, compositions containing sEH inhibitory compounds, and methods of treatment relating to diseases and conditions in which soluble epoxide hydrolase is implicated.

Epoxide hydrolases are a group of enzymes ubiquitous in nature, detected in species ranging from plants to mammals. These enzymes are functionally related in that they catalyze the addition of water to an epoxide, resulting in the formation of a diol. Diols are frequently found as intermediates in metabolic pathways.

Several types of epoxide hydrolases have been characterized, including soluble epoxide hydrolase, also referred to as cytosolic epoxide hydrolase, cholesterol epoxide hydrolase, LTA4 hydrolase, hepoxilin hydrolase, and microsomal epoxide hydrolase (mEH), (Fretland, et al. Chem. Biological Interactions, 129: 41-59 (2000)). Epoxide hydrolases have been found in mammalian heart, kidney and liver tissue (Vogel et al. Eur. J. Biochem. 126: 425-431 (1982) Schladt et al., Biochem Pharmacol. 35: 3309-3316 (1986). Epoxide hydrolases have also been detected in human blood components including lymphocytes (e.g., T-lymphocytes), monocytes, erythrocytes, and platelets. In the blood, most of the sEH detected was present in lymphocytes (Seidegard, et al. Cancer Research 44: 3654-3660 (1984).

The epoxide hydrolases differ in their specificity towards epoxide substrates. For example, sEH is selective for aliphatic epoxides such as epoxide fatty acids while microsomal epoxide hydrolase (mEH) is more selective for cyclic and arene epoxides. The primary known physiological substrates of sEH are the four regioisomeric epoxides of arachidonic acid, 5,6-, 8,9-, 11,12- and 14,15-epoxyeicosatrienoic acid, also known as epoxyeicosatrienoic acids or EETs. It has been reported that red blood cells can be reservoirs of EETs as well (Mini review: Jiang, H. Prostaglandins & other Lipid Mediators 2007, 82, 4). Also known to be substrates for sEH are epoxides of linoleic acid known as leukotoxin or isoleukotoxin.

The EETs are known to be vasodilatory mediators. Their role in vessel relaxation of peripheral vessels and renal microvessels, stems from their activation of BKCa ion channels. Furthermore 11,12-EET has been identified as the endothelial derived hyperpolarization factor (EDHF). These properties of EETs render them an attractive target for elevation in vivo, with application to improving endothelial dysfunction. Endothelial mediated vessel relaxation can contribute 25-40% of insulin stimulated glucose uptake during a euglycemic clamp (Kim, et. al. Circulation 2006, 113, 1888). Hence, one object of the present invention is to provide compounds that are useful for the treatment of type 2 diabetes and related conditions.

Endothelial dysfunction plays a significant role in a large number of pathological conditions including type 1 and 2 diabetes, insulin resistance, hypertension, atherosclerosis, coronary artery disease, angina, ischemia, ischemic stroke, Raynaud's disease and renal disease (Cersosimo, et. al. Diabetes/Metabolism Research and Reviews 2006, 22, 423).

Other effects of EET's involve kidney function. In angiotensin II infused rats, treatment with a selective sEH inhibitor attenuated the afferent arteriolar diameter in the kidney and lowered urinary albumin secretion, a marker of compromised renal function, suggesting antihypertensive and renal vascular protective effects of increased EET levels. Administration of a (selective) sEH inhibitor to angiotensin II treated rats was demonstrated to lower systolic blood pressure (Imig, et al. Hypertension, 39: 690-694 (2002)). Hence, one object of the present invention is to provide end organ protection along with the treatment of hypertension.

EET's, and especially 11,12-EET, also have been shown to exhibit anti-inflammatory properties (Node, et al. Science 285: 1276-1279 (1999)); Campbell, TIPS 21: 125-127 (2000); Zeldin et al. TIPS 21: 127-128 (2000)). Node et al. demonstrated that 11,12-EET decreased expression of cytokine induced endothelial cell adhesion molecules, especially VCAM-1. Moreover, EETs prevented leukocyte adhesion to the vascular wall and the mechanism responsible involved inhibition of NFκB and IKB kinase. Vascular inflammation plays a role in endothelial dysfunction (Kessler, et al. Circulation, 99: 1878-1884 (1999)). Hence, the ability of EETs to inhibit the NFκB pathway should also help ameliorate this condition. In addition, the administration of EETs and/or the administration of a selective sEH inhibitor was demonstrated to attenuate tobacco smoke induced inflammation, as assessed by total bronchioalveolar lavage cell numbers and concommitant reduction in neutrophils, alveolar macrophages and lymphocytes.

Hammock et al. have demonstrated usefulness in the treatment of inflammatory diseases, in particular, adult respiratory distress syndrome and other acute inflammatory conditions mediated by lipid metabolites, by the administration of inhibitors of epoxide hydrolase (WO98/06261, U.S. Pat. No. 5,955,496).

More recently, Hammock, et al. disclosed certain biologically stable inhibitors of sEH for the treatment of inflammatory diseases, for use in affinity separations of epoxide hydrolases and in agricultural applications (U.S. Pat. No. 6,150, 415). Hammock et al. generally described compounds that can be used to deliver a reactive functionality to the catalytic site, e.g., alkylating agents or Michael acceptors, and that these reactive functionalities can be used to deliver fluorescent or affinity labels to the enzymes active site for enzyme detection. Certain urea and carbamate inhibitors of sEH have also been described in the literature (Morisseau, et al. Proc. Nat. Acad. Sci. 96: 8849-8854 (1999)).

A number of other chemical classes of sEH inhibitors have been identified. Among these are chalcone oxide derivatives (Miyamoto, et al. Arch. Biochem. Biophys. 254: 203-213 (1987)) and various trans-3-phenylglyucidols (Dietze, et al. Biochem. Pharm. 42: 1163-1175 (1991)) and Dietze, et al. Comp. Biochem. Physiol. B. 104: 309-314 (1993)).

It has recently been shown that sEH inhibition reduces COX-2 expression in mammals, and decreases PGE2 and PGD2 levels, similar to coxibs. Therefore, sEH inhibitors could be indicated for inflammatory pain (Schmelzer, et. al. PNAS 2006, 103, 13646). It has also been disclosed that 14,15-EET is 100-fold more potent than morphine dosed vPAG in rat brains, and EETs induce Met-enkephalin release in the spinal cord. This suggests that sEH inhibitors could also be used for CNS analgesia (Harder, D. presented at 9$^{th}$ Annual WEC, March 2007).

The anti-inflammatory functions of EETs also indicate that it is possible to use sEH inhibitors as ophthalmic agents to alleviate eye disorders, such as reducing intraocular pressure and reducing progression of age-related macular degeneration (WO 2007/009001 A1).

All four EET regioisomers inhibit arachidonic acid-induced aggregation of human platelets, induce t-PA expression and hyperpolarize platelets. This supports the potential use of sEH inhibitors as anti-thrombotic agents.

Another object of the present invention is to provide compounds that are useful for the treatment of hyperlipidemias, dyslipidemias, atherosclerosis and related conditions.

Another object is to provide a pharmaceutical composition for oral use.

These and other objects will be apparent from the description provided herein.

SUMMARY OF THE INVENTION

A compound represented by formula I is disclosed:

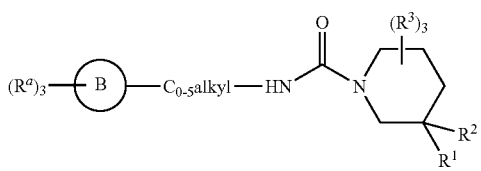

or a pharmaceutically acceptable salt or solvate thereof is disclosed wherein:

ring B represents Aryl, HAR, Hetcy, $C_{3-7}$cycloalkyl, $C_{5-7}$cycloalkyl fused to an Aryl or HAR group, Aryl or HAR fused to $C_{5-7}$cycloalkyl, or $C_{6-10}$bicycloalkyl;

each $R^a$ is defined as follows:
a) each $R^a$ is H or halo, or
b) 1-2 $R^a$ groups represent H or halo,
0-1 $R^a$ represents Aryl, HAR or Hetcy, each of which being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;
and any remaining $R^a$ groups are selected from the group consisting of $C_{1-3}$alkyl, $OC_{1-3}$alkyl, halo$C_{1-3}$alkyl, Ohalo$C_{1-3}$alkyl, $S(O)_xC_{1-3}$alkyl, $S(O)_x$-halo$C_{1-3}$alkyl, $S(O)_x$Aryl wherein x is 0, 1 or 2, $CO_2R^b$ or $C_{1-3}$alkyl-$CO_2R^b$, wherein $R^b$ is H, $C_{1-4}$alkyl, halo$C_{1-4}$alkyl, Aryl, HAR or Hetcy;

$R^1$ is selected from the group consisting of:
a) $CO_2R^d$ in which $R^d$ represents H, $C_{1-3}$alkyl-$R^e$, Aryl, HAR or Hetcy, wherein $R^e$ is selected from the group consisting of H, $OC_{1-3}$alkyl, halo, Ohalo$C_{1-3}$alkyl, $S(O)_xC_{1-3}$alkyl, $S(O)_x$halo$C_{1-3}$alkyl, Aryl, HAR, Hetcy, $S(O)_x$-Aryl or $CO_2R^b$;
b) halo or CN;
c) $C_{1-6}$alkyl or $OC_{1-6}$alkyl, each optionally substituted with up to 3 halo groups, and a member selected from the group consisting of:
i) CN, $C(O)NH_2$, $C(O)NHCH_3$ or $C(O)N(CH_3)_2$;
ii) $CO_2R^d$ with $R^d$ as previously defined in a) above;
iii) OH, $OC_{1-3}$alkyl, haloOC$_{1-3}$alkyl, $NH_2$, $NHCH_3$ or $N(CH_3)_2$;
iv) Aryl or HAR, each being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;

d) Aryl or HAR, each optionally substituted with 1-2 halo, $C_{1-3}$alkyl, halo$C_{1-3}$alkyl, $OC_{1-3}$alkyl, Ohalo$C_{1-3}$alkyl and Aryl($R^a$)$_3$ groups and 0-1 members selected from the group consisting of: CN, HAR($R^a$)$_3$, $CO_2C_{1-6}$alkyl, $CO_2H$, $C(O)N(R^f)_2$, NHC(O)N($R^f$)$_2$ and NHC(O)OR$^g$ wherein each $R^f$ is H or $C_{1-6}$alkyl and each $R^g$ represents $C_{1-3}$alkyl, halo$C_{1-3}$alkyl, Aryl, HAR or Hetcy;

$R^2$ is selected from the group consisting of:
—(CR$^h_2$)$_{0-2}$—Y—(CR$^h_2$)$_{0-2}$-Aryl($R^a$)$_3$, and —(CR$^h_2$)$_{0-2}$—Y—(CR$^h_2$)$_{0-2}$-HAR($R^a$)$_3$,
wherein Y represents a bond, $CH_2$, O, $S(O)_x$, $C(O)NR^f$, NR$^f$C(O), C(O) or NR$^f$C(O)O; x, and $R^f$ are as previously defined and $R^h$ represents a member selected from the group consisting of: H, $C_{1-3}$alkyl, $OC_{1-3}$alkyl and halo;

and each $R^3$ is selected from the group consisting of: H, halo, $C_{1-3}$alkyl, $OC_{1-3}$alkyl, halo$C_{1-3}$alkyl and Ohalo$C_{1-3}$alkyl, or one $R^3$ group is selected from d) above, and the other two $R^3$ groups represent H, halo, $C_{1-3}$alkyl, $OC_{1-3}$alkyl, halo$C_{1-3}$alkyl, Ohalo$C_{1-3}$alkyl, $CO_2R^b$ or $C(O)NHR^b$.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-7 carbon atoms are intended, forming 1-3 carbocyclic rings that are fused. "Cycloalkyl" can also be fused to an aryl or heteroaryl group. Examples of cycloalkyl include cyclopropyl, cyclobutyl, cyclopentyl, cyclohexyl, cycloheptyl, tetrahydronaphthyl, decahydronaphthyl, indanyl and the like. Haloalkoxy and haloOalkyl are used interchangeably and refer to halo substituted alkyoxy groups linked through the oxygen atom. Haloalkyl and haloalkoxy include mono-substituted as well as multiple substituted alkyl and alkoxy groups, up to perhalo substituted alkyl and alkoxy. For example, trifluoromethyl and trifluoromethoxy are included.

"Aryl" (Ar) means mono- and bicyclic aromatic rings containing 6-10 carbon atoms. Examples of aryl include phenyl, naphthyl, indenyl and the like.

"Heteroaryl" (HAR) unless otherwise specified, means mono-, bicyclic and tricyclic aromatic ring systems containing at least one heteroatom selected from O, S, S(O), $SO_2$ and N, with each ring containing 5 to 6 atoms. HAR groups may contain from 5-14, preferably 5-13 atoms. Examples include, but are not limited to, pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzopyrazolyl, benzotriazolyl, furo(2,3-b)pyridyl, benzoxazinyl, tetrahydrohydroquinolinyl, tetrahydroisoquinolinyl, quinolyl, isoquinolyl, indolyl, dihydroindolyl, quinoxalinyl, quinazolinyl, naphthyridinyl, pteridinyl, 2,3-dihydrofuro(2,3-b)pyridyl and the like. Heteroaryl also includes aromatic carbocyclic or heterocyclic groups fused to heterocycles that are non-aromatic or partially aromatic, and optionally containing a carbonyl. Examples of additional heteroaryl groups include indolinyl, dihydrobenzofuranyl, dihydrobenzothiophenyl, dihydrobenzoxazolyl, and aromatic heterocyclic groups fused to cycloalkyl rings. Examples also include the following:

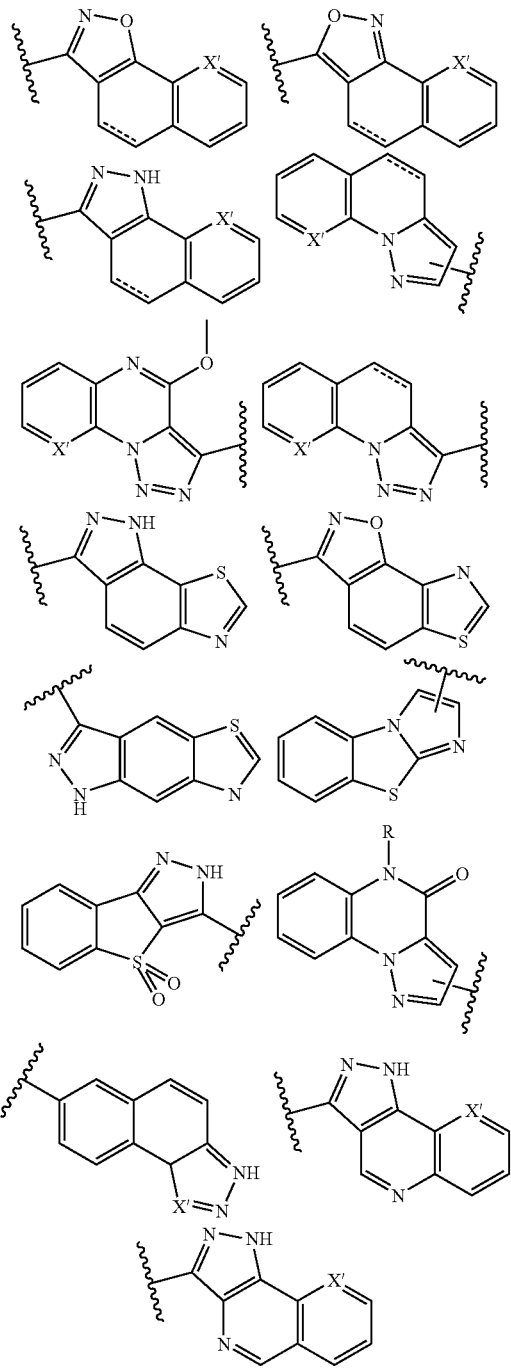

----- is a single or double bond
X' = CH or N
R = H or CH$_3$

Heteroaryl also includes such groups in charged form, e.g., pyridinium.

"Heterocyclyl" (Hetcy) unless otherwise specified, means mono- and bicyclic saturated and partially saturated rings and ring systems containing at least one heteroatom selected from N, S and O, each of said ring having from 3 to 10 atoms in which the point of attachment may be carbon or nitrogen.

Examples of "heterocyclyl" include, but are not limited to, azetidinyl, pyrrolidinyl, piperidinyl, piperazinyl, imidazolidinyl, tetrahydrofuranyl, 1,4-dioxanyl, morpholinyl, thiomorpholinyl, tetrahydrothienyl and the like. Heterocycles can also exist in tautomeric forms, e.g., 2- and 4-pyridones. Heterocycles moreover includes such moieties in charged form, e.g., piperidinium.

"Halogen" (Halo) includes fluorine, chlorine, bromine and iodine.

In its broadest aspect, the invention relates to a compound represented by formula I is disclosed:

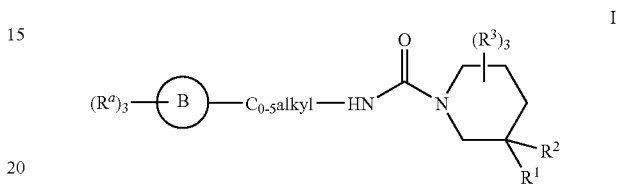

or a pharmaceutically acceptable salt or solvate thereof is disclosed wherein:

ring B represents Aryl, HAR, Hetcy, $C_{3-7}$cycloalkyl, $C_{5-7}$cycloalkyl fused to an Aryl or HAR group, Aryl or HAR fused to $C_{5-7}$cycloalkyl, or $C_{6-10}$bicycloalkyl;

each $R^a$ is defined as follows:
a) each $R^a$ is H or halo, or
b) 1-2 $R^a$ groups represent H or halo,
0-1 $R^a$ represents Aryl, HAR or Hetcy, each of which being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;
and any remaining $R^a$ groups are selected from the group consisting of: $C_{1-3}$alkyl, $OC_{1-3}$alkyl, halo$C_{1-3}$alkyl, Ohalo$C_{1-3}$alkyl, $S(O)_xC_{1-3}$alkyl, $S(O)_x$-halo$C_{1-3}$alkyl, $S(O)_x$Aryl wherein x is 0, 1 or 2, $CO_2R^b$ or $C_{1-3}$alkyl-$CO_2R^b$, wherein $R^b$ is H, halo$C_{1-4}$alkyl, Aryl, HAR or Hetcy;

$R^1$ is selected from the group consisting of:
a) $CO_2R^d$ in which $R^d$ represents H, $C_{1-3}$alkyl-$R^e$, Aryl, HAR or Hetcy, wherein $R^e$ is selected from the group consisting of H, $OC_{1-3}$alkyl, halo, Ohalo$C_{1-3}$alkyl, $S(O)_xC_{1-3}$alkyl, $S(O)_x$halo$C_{1-3}$alkyl, Aryl, HAR, Hetcy, $S(O)_x$-Aryl or $CO_2R^b$;
b) halo or CN;
c) $C_{1-6}$alkyl or $OC_{1-6}$alkyl, each optionally substituted with up to 3 halo groups, and a member selected from the group consisting of:
i) CN, $C(O)NH_2$, $C(O)NHCH_3$ or $C(O)N(CH_3)_2$;
ii) $CO_2R^d$ with $R^d$ as previously defined in a) above;
iii) OH, $OC_{1-3}$alkyl, haloO$C_{1-3}$alkyl, $NH_2$, $NHCH_3$ or $N(CH_3)_2$;
iv) Aryl or HAR, each being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;
d) Aryl or HAR, each optionally substituted with 1-2 halo, $C_{1-3}$alkyl, halo$C_{1-3}$alkyl, $OC_{1-3}$alkyl, Ohalo$C_{1-3}$alkyl and Aryl($R^a$)$_3$ groups and 0-1 members selected from the group consisting of: CN, HAR($R^a$)$_3$, $CO_2C_{1-6}$alkyl, $CO_2H$, $C(O)N(R^f)_2$, $NHC(O)N(R^f)_2$ and $NHC(O)OR^g$ wherein each $R^f$ is H or $C_{1-6}$alkyl and each $R^g$ represents $C_{1-3}$alkyl, halo$C_{1-3}$alkyl, Aryl, HAR or Hetcy;

$R^2$ is selected from the group consisting of:
—$(CR^h{}_2)_{0-2}$—Y—$(CR^h{}_2)_{0-2}$-Aryl($R^a$)$_3$, and —$(CR^h{}_2)_{0-2}$—Y—$(CR^h{}_2)_{0-2}$-HAR($R^a$)$_3$, wherein Y represents a bond, $CH_2$, O, $S(O)_x$, $C(O)NR^f$, $NR^fC(O)$, $C(O)$ or $NR^fC(O)O$; x, and $R^f$ are as previously defined and $R^h$ represents a member selected from the group consisting of: H, $C_{1-3}$alkyl, $OC_{1-3}$alkyl and halo;

and each $R^3$ is selected from the group consisting of: H, halo, $C_{1-3}$alkyl, $OC_{1-3}$alkyl, halo$C_{1-3}$alkyl and Ohalo$C_{1-3}$alkyl, or one $R^3$ group is selected from d) above, and the other two $R^3$ groups represent H, halo, $C_{1-3}$alkyl, $OC_{1-3}$alkyl, halo$C_{1-3}$alkyl, $CO_2R^b$ or $C(O)NHR^b$.

One group of compounds of the invention that is of interest relates to compounds of formula I or a pharmaceutically acceptable salt or solvate thereof wherein ring B represents: a) Aryl which is further defined as phenyl; b) HAR which is selected from the group consisting of: pyridyl, pyrazolyl, thiadiazolyl, benzisoxazolyl, benzthiazolyl, pyrimidinyl, thiazolyl, oxadiazolyl, triazolyl, tetrazolyl, and benzopyrazinyl; c) $C_{10}$-bicycloalkyl and d) $C_{6-7}$cycloalkyl fused to an Aryl group, wherein Aryl is further defined as phenyl. Within this subset, all other variables are as originally defined with respect to formula I.

Another aspect of the invention that is of interest relates to a subset of compounds of formula I or a pharmaceutically acceptable salt or solvate thereof wherein: $C_{0-5}$alkyl is further defined as a group selected from: a direct bond; —$CH_2$—; —$(CH_2)_2$—; —$(CH_2)_3$—; —$(CH_2)_4$—;

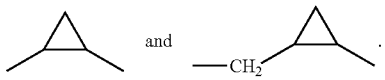

Within this subset, all other variables are as originally defined with respect to formula I.

Yet another aspect of the invention that is of interest relates to compounds of formula I or a pharmaceutically acceptable salt or solvate thereof wherein each $R^a$ is defined as follows:

a) each $R^a$ is H or halo which is further defined as F or Cl, or b) 1-2 $R^a$ groups represent H or halo which is further defined as F or Cl, 0-1 $R^a$ represents Aryl which is further defined as phenyl, or HAR which is further defined as a 5-10 membered heteroaryl group having 1-2 N atoms, each of which being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;

and any remaining $R^a$ groups are selected from the group consisting of: $C_{1-3}$alkyl, $OC_{1-3}$alkyl, halo$C_{1-3}$alkyl and Ohalo$C_{1-3}$alkyl. Within this subset, all other variables are as originally defined with respect to formula I.

Another aspect of the invention that is of interest relates to compounds of formula I or a pharmaceutically acceptable salt or solvate thereof wherein $R^1$ is selected from the group consisting of:

a) $CO_2R^d$ in which $R^d$ represents H or $C_{1-3}$alkyl-$R^e$, wherein $R^e$ represents H or Aryl;
b) CN or halo, which is further defined as F or Cl;
c) $C_{1-6}$alkyl or $OC_{1-6}$alkyl, each optionally substituted with up to 3 halo groups selected from Cl and F, and a member selected from the group consisting of:
  i) CN, $C(O)NH_2$, and $C(O)NHCH_3$;
  ii) $CO_2R^d$ with $R^d$ as previously defined in a) above;
  iii) $OC_{1-3}$alkyl and Ohalo$C_{1-3}$alkyl, in which the halo atoms are selected from Cl and F;
  iv) Aryl, which is defined as phenyl, HAR, which is a 5-10 membered mono or bicyclic ring system with 1-4 heteroatoms selected from O, S and N, 0-1 of which are O or S, and 0-4 of which are N,
  said Aryl and HAR each being optionally substituted with 1-2 halo atoms selected from F and Cl, $C_{1-2}$alkyl or halo$C_{1-2}$alkyl groups, in which the halo atoms are selected from F and Cl, and 0-1 members selected from —$C_{1-3}$alkyl-Aryl and —$CO_2$—$C_{1-6}$alkyl;
d) Aryl or HAR, each optionally substituted with 1-2 halo atoms selected from F and Cl, $C_{1-2}$alkyl, halo$C_{1-2}$alkyl, $OC_{1-2}$alkyl, Ohalo$C_{1-2}$alkyl, the halo atoms contained in haloalkyl and Ohaloalkyl being selected from F and Cl, and Aryl$(R^a)_3$ in which the Aryl portion is phenyl, and 0-1 members selected from the group consisting of: CN, HAR$(R^a)_3$, $CO_2C_{1-4}$alkyl, $CO_2H$ and $C(O)N(R^f)_2$, wherein each $R^f$ is H or $C_{1-6}$alkyl. Within this subset, all other variables are as originally defined with respect to formula I.

Another aspect of the invention that is of interest relates to compounds of formula I or a pharmaceutically acceptable salt or solvate thereof wherein $R^2$ is selected from the group consisting of: —$(CR^h_2)_{0-1}$—Y—$(CR^h_2)_{0-2}$-Aryl$(R^a)_3$, and —$(CR^h_2)_{0-1}$—Y—$(CR^h_2)_{0-2}$-HAR$(R^a)_3$, in which Aryl represents phenyl or naphthyl, and HAR represents a 5-10 membered mono or bicyclic aromatic ring system containing 1-4 heteroatoms selected from O, S and N, 0-1 of which are O or S, and 1-4 of which are N;

Y represents a bond, $CH_2$, O, $C(O)NR^f$, $NR^fC(O)$ or $NR^fC(O)O$; and $R^h$ represents a member selected from the group consisting of: H, $CH_3$ and F.

Within this subset, all other variables are as originally defined with respect to formula I.

Another aspect of the invention that is of interest relates to compounds of formula I or a pharmaceutically acceptable salt or solvate thereof wherein each $R^3$ is selected form the group consisting of: H, F, $CH_3$, $OCH_3$, $CF_3$ and $OCF_3$ Within this subset, all other variables are as originally defined with respect to formula I.

Another aspect of the invention that is of particular interest relates to compounds of formula I or a pharmaceutically acceptable salt or solvate thereof wherein ring B is selected from the group consisting of: phenyl, pyridyl, pyrazolyl, thiadiazolyl, benzisoxazolyl, benzthiazolyl; pyrimidinyl, thiazolyl, oxadiazolyl, triazolyl, tetrazolyl, benzopyrazinyl and tetrahydronaphthyl. Within this subset, all other variables are as originally defined with respect to formula I.

Yet another aspect of the invention that is of particular interest relates to compounds of formula I or a pharmaceutically acceptable salt or solvate thereof wherein ring B is selected from the group consisting of: phenyl, pyridyl, pyrazolyl, thiadiazolyl, benzthiazolyl, pyrimidinyl, thiazolyl, oxadiazolyl, triazolyl, tetrazolyl and tetrahydronaphthyl. Within this subset, all other variables are as originally defined with respect to formula I.

Yet another aspect of the invention that is of more particular interest relates to compounds of formula I or a pharmaceutically acceptable salt or solvate thereof wherein ring B is selected from the group consisting of: phenyl, pyridyl, pyrazolyl, and thiadiazolyl. Within this subset, all other variables are as originally defined with respect to formula I.

Yet another aspect of the invention that is of even more particular interest relates to compounds of formula I or a pharmaceutically acceptable salt or solvate thereof wherein ring B represents phenyl. Within this subset, all other variables are as originally defined with respect to formula I.

Yet another aspect of the invention that is of interest relates to compounds of formula I or a pharmaceutically acceptable salt or solvate thereof wherein $C_{0-5}$ alkyl represents a member selected from the group consisting of: a bond, —$CH_2$—, —$CH_2CH_2$—, —$CH_2CH_2CH_2$—,

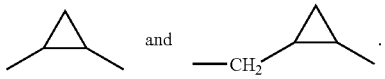

Within this subset, all other variables are as originally defined with respect to formula I.

More particularly, an aspect of the invention that is of interest relates to compounds of formula I or a pharmaceutically acceptable salt or solvate thereof wherein $C_{0-5}$ alkyl represents a member selected from the group consisting of: a bond, —$CH_2$—, —$CH_2CH_2$—, —$CH_2CH_2CH_2$— and

Within this subset, all other variables are as originally defined with respect to formula I.

Another aspect of the invention that is of particular interest relates to compounds of formula I or a pharmaceutically acceptable salt or solvate thereof wherein: one $R^a$ represents H;

another $R^a$ is selected from the group consisting of: H and Cl, and the third $R^a$ is selected from the group consisting of H, Cl, phenyl, pyridyl, indolyl, isoquinolinyl, and benzopyrazolyl, $CH_3$, $OCH_3$, $CF_3$, $SCF_3$ and $OCF_3$. Within this subset, all other variables are as originally defined with respect to formula I.

Yet another aspect of the invention that is of particular interest relates to compounds of formula I or a pharmaceutically acceptable salt or solvate thereof wherein: two $R^a$ groups represents H;

and the third $R^a$ is selected from the group consisting of H, Cl, phenyl, pyridyl, $CH_3$, $OCH_3$, $CF_3$, $SCF_3$ and $OCF_3$. Within this subset, all other variables are as originally defined with respect to formula I.

Yet another aspect of the invention that is of particular interest relates to compounds of formula I or a pharmaceutically acceptable salt or solvate thereof wherein:

$R^1$ is selected from the group consisting of:
a) $CO_2R^d$ in which $R^d$ represents H or $CH_2$—$R^e$, wherein $R^e$ represents H, $CH_3$, or phenyl;
b) F, Cl or CN;
c) $C_{1-3}$alkyl or $OC_{1-3}$alkyl, each optionally substituted with up to 3 fluorine atoms, and a member selected from the group consisting of:
  i) CN or $C(O)NH_2$;
  ii) $CO_2R^d$ with $R^d$ as previously defined in a) above;
  iii) Phenyl or HAR, which is a 5-10 membered mono or bicyclic ring system with 1-4 heteroatoms selected from O, S and N, 0-1 of which are O or S, and 0-4 of which are N,
    said Aryl and HAR each being optionally substituted with 1-2 halo atoms selected from F and Cl, $C_{1-2}$alkyl or halo$C_{1-2}$ alkyl groups, in which the halo atoms are selected from F and Cl, and 0-1 members selected from —$C_{1-3}$alkyl-Aryl and —$CO_2$—$C_{1-6}$alkyl;
d) Phenyl or HAR containing 5-10 atoms, 1-4 of which are heteroatoms, 0-1 being selected from O and S, and 1-4 of which are N atoms, said Phenyl and HAR being optionally substituted with 1-2 halo atoms selected from F and Cl, $C_{1-2}$alkyl, halo$C_{1-2}$alkyl, $OC_{1-2}$alkyl, Ohalo$C_{1-2}$alkyl, the halo atoms contained in haloalkyl and Ohaloalkyl being selected from F and Cl, and Phenyl$(R^a)_3$, and 0-1 members selected from the group consisting of: CN, HAR$(R^a)_3$, $CO_2C_{1-4}$alkyl, $CO_2H$ and $C(O)N(R^f)_2$, wherein each $R^f$ is H or $C_{1-6}$alkyl. Within this subset, all other variables are as originally defined with respect to formula I.

Another aspect of the invention that is of particular interest relates to compounds of formula I or a pharmaceutically acceptable salt or solvate thereof wherein $R^2$ is selected from the group consisting of:

—$(CR^h_2)_{0-1}$—Y—$(CR^h_2)_{0-2}$-Aryl$(R^a)_3$, and —$(CR^h_2)_{0-1}$ —Y—$(CR^h_2)_{0-2}$-HAR$(R^a)_3$, in which Aryl represents phenyl or naphthyl, and HAR represents a 5-9 membered mono or bicyclic aromatic ring system containing 1-4 heteroatoms selected from O, S and N, 0-1 of which are O or S, and 1-4 of which are N;

Y represents a bond, $CH_2$, O, $C(O)NR^f$, $NR^fC(O)$, or $NR^fC(O)O$; and each $R^h$ represents a hydrogen atom. Within this subset, all other variables are as originally defined with respect to formula I.

Yet another aspect of the invention that is of particular interest relates to compounds of formula I or a pharmaceutically acceptable salt or solvate thereof wherein: each $R^3$ is selected from the group consisting of: H, F and $CH_3$. Within this subset, all other variables are as originally defined with respect to formula I.

More particularly, an aspect of the invention that is of interest relates to a compound of the formula:

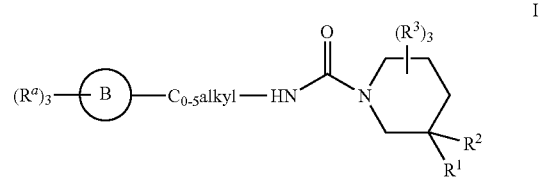

or a pharmaceutically acceptable salt or solvate thereof is disclosed wherein:

ring B represents: a) Aryl which is further defined as phenyl; b) HAR which is selected from the group consisting of: pyridyl, pyrazolyl, thiadiazolyl, benzisoxazolyl, benzthiazolyl, pyrimidinyl, thiazolyl, oxadiazolyl, triazolyl, tetrazolyl and benzopyrazinyl; c) $C_{10}$-bicycloalkyl and d) $C_{6-7}$-cycloalkyl fused to an Aryl group, wherein Aryl is further defined as phenyl;

—$C_{0-5}$alkyl is further defined as a group selected from: a direct bond; —$CH_2$—; —$(CH_2)_2$—; —$(CH_2)_3$—; —$(CH_2)_4$—;

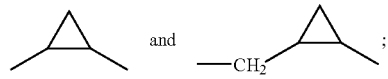

each $R^a$ is defined as follows:

a) each $R^a$ is H or halo which is further defined as F or Cl, or b) 1-2 $R^a$ groups represent H or halo which is further defined as F or Cl, 0-1 $R^a$ represents Aryl which is further defined as phenyl, or HAR which is further defined as a 5-10 membered heteroaryl group having 1-2 N atoms, each of which being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;

and any remaining $R^a$ groups are selected from the group consisting of: $C_{1-3}$alkyl, $OC_{1-3}$alkyl, halo$C_{1-3}$alkyl and Ohalo$C_{1-3}$alkyl;

$R^1$ is selected from the group consisting of:

a) $CO_2R^d$ in which $R^d$ represents H or $C_{1-3}$alkyl-$R^e$, wherein $R^e$ represents H or Aryl;

b) CN or halo, which is further defined as F or Cl;

c) $C_{1-6}$alkyl or $OC_{1-6}$alkyl, each optionally substituted with up to 3 halo groups selected from Cl and F, and a member selected from the group consisting of:

i) CN, $C(O)NH_2$, and $C(O)NHCH_3$;

ii) $CO_2R^d$ with $R^d$ as previously defined in a) above;

iii) $OC_{1-3}$alkyl and Ohalo$C_{1-3}$alkyl, in which the halo atoms are selected from Cl and F;

iv) Aryl, which is defined as phenyl, HAR, which is a 5-10 membered mono or bicyclic ring system with 1-4 heteroatoms selected from O, S and N, 0-1 of which are O or S, and 0-4 of which are N, said Aryl and HAR each being optionally substituted with 1-2 halo atoms selected from F and Cl, $C_{1-2}$alkyl or halo $C_{1-2}$alkyl groups, in which the halo atoms are selected from F and Cl, and 0-1 members selected from —$C_{1-3}$alkyl-Aryl and —$CO_2$—$C_{1-6}$alkyl;

d) Aryl or HAR, each optionally substituted with 1-2 halo atoms selected from F and Cl, $C_{1-2}$alkyl, halo$C_{1-2}$alkyl, $OC_{1-2}$alkyl, Ohalo$C_{1-2}$alkyl, the halo atoms contained in haloalkyl and Ohaloalkyl being selected from F and Cl, and Aryl($R^a$)$_3$ in which the Aryl portion is phenyl, and 0-1 members selected from the group consisting of: CN, HAR($R^a$)$_3$, $CO_2C_{1-4}$alkyl, $CO_2H$ and $C(O)N(R^f)_2$, wherein each $R^f$ is H or $C_{1-6}$alkyl;

$R^2$ is selected from the group consisting of:
—($CR^h_2$)$_{0-1}$—Y—($CR^h_2$)$_{0-2}$-Aryl($R^a$)$_3$, and —($CR^h_2$)$_{0-1}$—Y—($CR^h_2$)$_{0-2}$-HAR($R^a$)$_3$, in which Aryl represents phenyl or naphthyl, and HAR represents a 5-10 membered mono or bicyclic aromatic ring system containing 1-4 heteroatoms selected from O, S and N, 0-1 of which are O or S, and 1-4 of which are N;

Y represents a bond, $CH_2$, O, $C(O)NR^f$, $NR^fC(O)$ or $NR^fC(O)O$; and $R^h$ represents a member selected from the group consisting of: H, $CH_3$ and F;

and each $R^3$ is selected form the group consisting of: H, F, $CH_3$, $OCH_3$, $CF_3$ and $OCF_3$ Within this subset, all other variables are as originally defined with respect to formula I.

More particularly, an aspect of the invention that is of interest relates to a compound of formula I:

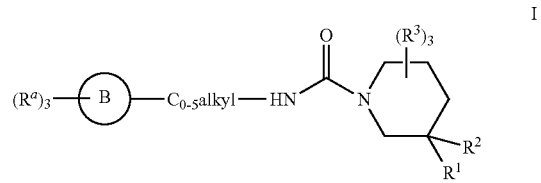

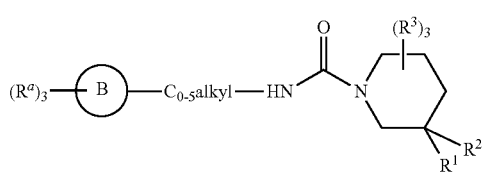

or a pharmaceutically acceptable salt or solvate thereof is disclosed wherein:

ring B is selected from the group consisting of: phenyl; pyridyl, pyrazolyl, thiadiazolyl, benzisoxazolyl, benzthiazolyl, benzopyrazinyl, pyrimidinyl, thiazolyl, oxadiazolyl, triazolyl, tetrazolyl and tetrahydronaphthyl;

$C_{0-5}$ alkyl represents a member selected from the group consisting of: a bond, —$CH_2$—, —$CH_2CH_2$—, —$CH_2CH_2CH_2$—,

; and and one $R^a$ represents H;

another $R^a$ is selected from the group consisting of: H and Cl, and the third $R^a$ is selected from the group consisting of H, Cl, phenyl, pyridyl, indolyl, isoquinolinyl, and benzopyrazolyl, $CH_3$, $OCH_3$, $CF_3$ and $OCF_3$;

$R^1$ is selected from the group consisting of:

a) $CO_2R^d$ in which $R^d$ represents H or $CH_2$—$R^e$, wherein $R^e$ represents H or methyl;

b) For CN;

c) $C_{1-3}$alkyl or $OC_{1-3}$alkyl, each optionally substituted with up to 3 fluorine atoms, and a member selected from the group consisting of:

i) CN or $C(O)NH_2$;

ii) $CO_2R^d$ with $R^d$ as previously defined in a) above;

iii) Phenyl or HAR, which is a 5-10 membered mono or bicyclic ring system with 1-4 heteroatoms selected from O, S and N, 0-1 of which are O or S, and 0-4 of which are N, said Aryl and HAR each being optionally substituted with 1-2 halo atoms selected from F and Cl, $C_{1-2}$alkyl or halo$C_{1-2}$ alkyl groups in which the halo atoms are F atoms, and 0-1 members selected from —$C_{1-3}$alkyl-Aryl and —$CO_2$—$C_{1-6}$ alkyl;

d) Phenyl or HAR containing 5-10 atoms, 1-4 of which are heteroatoms, 0-1 being selected from O and S, and 1-4 of which are N atoms, said Phenyl and HAR being optionally substituted with 1-2 halo atoms selected from F and Cl, $C_{1-2}$alkyl, halo$C_{1-2}$alkyl, $OC_{1-2}$alkyl, Ohalo$C_{1-2}$alkyl, the halo atoms contained in haloalkyl and Ohaloalkyl being F atoms, and Phenyl($R^a$)$_3$, and 0-1 members selected from the group consisting of: CN, HAR($R^a$)$_3$, $CO_2C_{1-4}$alkyl, $CO_2H$ and $C(O)N(R^f)_2$, wherein each $R^f$ is H or $C_{1-6}$alkyl;

$R^2$ is selected from the group consisting of:

—$(CR^h{}_2)_{0-1}$—Y—$(CR^h{}_2)_{0-2}$-Aryl$(R^a)_3$, and —$(CR^h{}_2)_{0-1}$—Y—$(CR^h{}_2)_{0-2}$-HAR$(R^a)_3$, in which Aryl represents phenyl or naphthyl, and HAR represents a 5-10 membered mono or bicyclic aromatic ring system containing 1-4 heteroatoms selected from O, S and N, 0-1 of which are O or S, and 1-4 of which are N;

Y represents a bond, $CH_2$, O, C(O)$NR^f$, $NR^f$C(O), or $NR^f$C(O)O; and each $R^h$ represents a hydrogen atom, and each $R^3$ is selected from the group consisting of: H, F and $CH_3$ Within this subset, all other variables are as originally defined with respect to formula I.

Examples of compounds that fall within the invention described herein include those shown in Table I:

TABLE 1

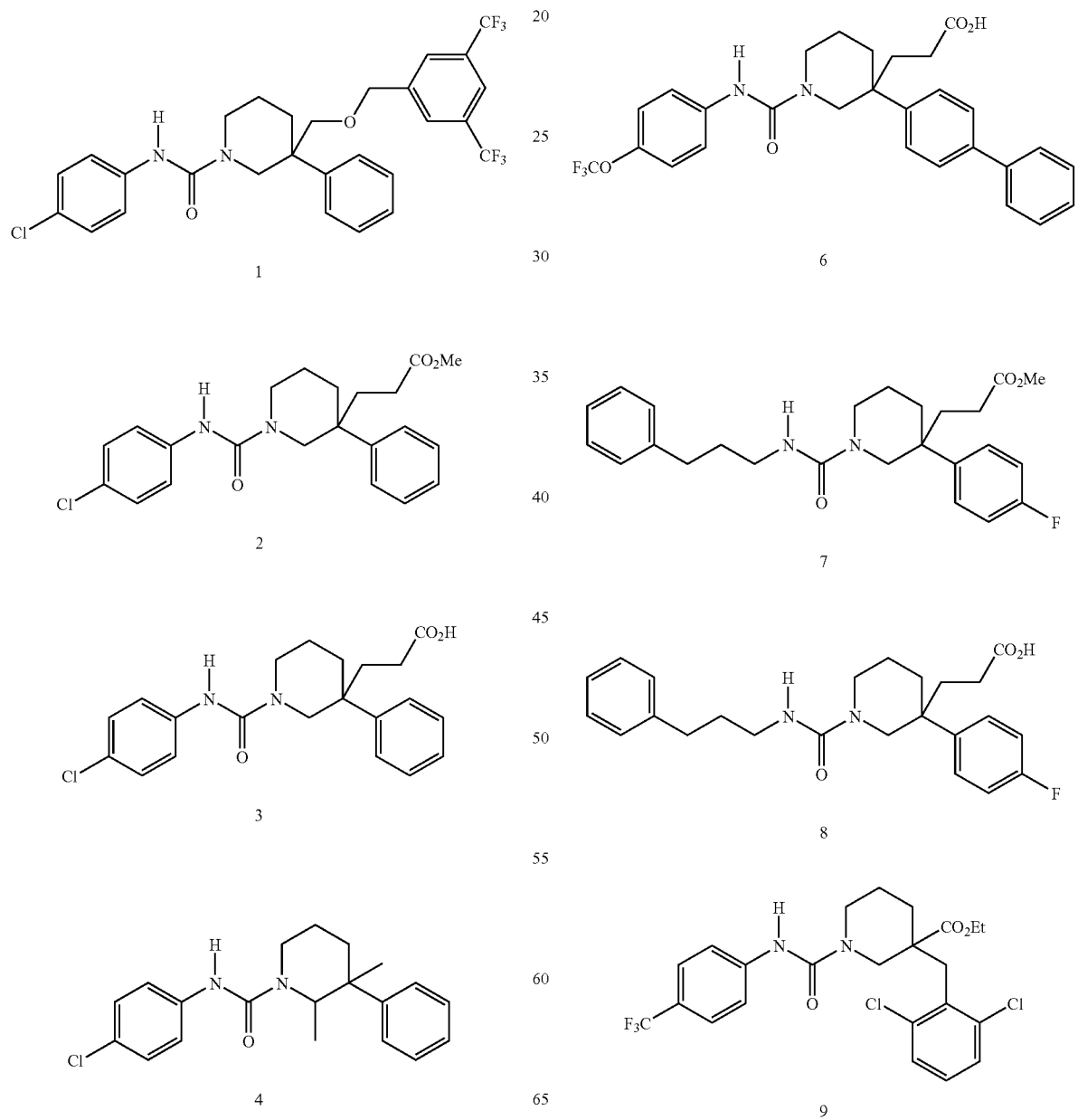

TABLE 1-continued

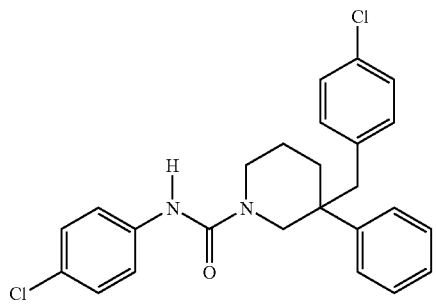 [SMILES: O=C(Nc1ccc(Cl)cc1)N1CCCC(Cc2ccc(Cl)cc2)(c2ccccc2)C1]

TABLE 1-continued
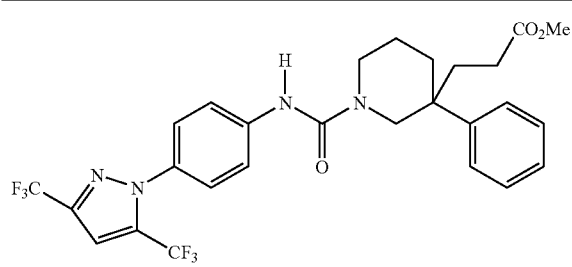
10
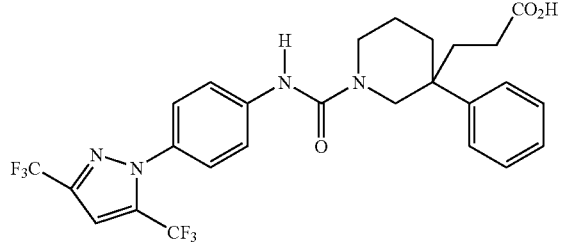 [SMILES: O=C(O)CCC1(c2ccccc2)CCCN(C(=O)Nc2ccc(-n3nc(C(F)(F)F)cc3C(F)(F)F)cc2)C1]
11
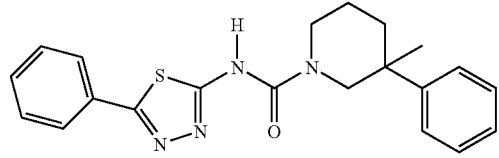 [SMILES: CC1(c2ccccc2)CCCN(C(=O)Nc2nnc(-c3ccccc3)s2)C1]
12
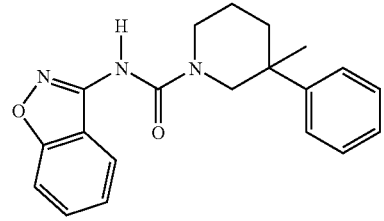 [SMILES: CC1(c2ccccc2)CCCN(C(=O)Nc2noc3ccccc23)C1]
13
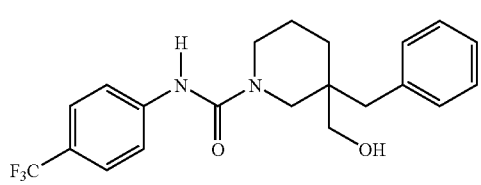 [SMILES: O=C(Nc1ccc(C(F)(F)F)cc1)N1CCCC(CO)(Cc2ccccc2)C1]
14
TABLE 1-continued
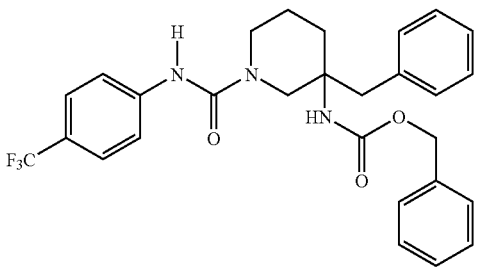 [SMILES: O=C(NC1(Cc2ccccc2)CCCN(C(=O)Nc2ccc(C(F)(F)F)cc2)C1)OCc1ccccc1]
15
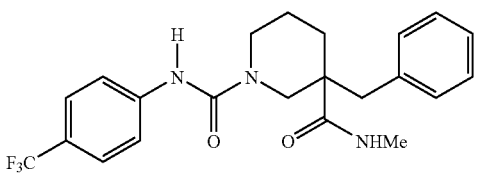 [SMILES: CNC(=O)C1(Cc2ccccc2)CCCN(C(=O)Nc2ccc(C(F)(F)F)cc2)C1]
16
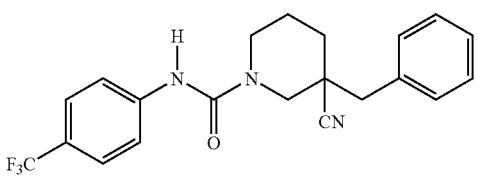 [SMILES: N#CC1(Cc2ccccc2)CCCN(C(=O)Nc2ccc(C(F)(F)F)cc2)C1]
17
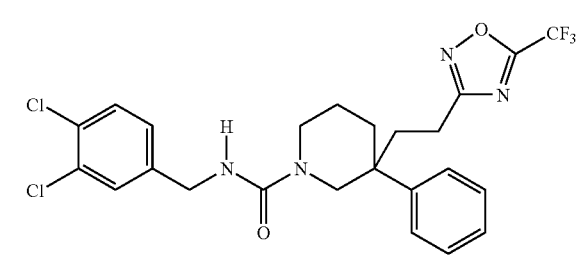
18
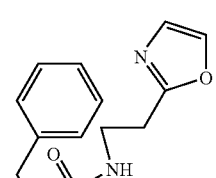
19

TABLE 1-continued
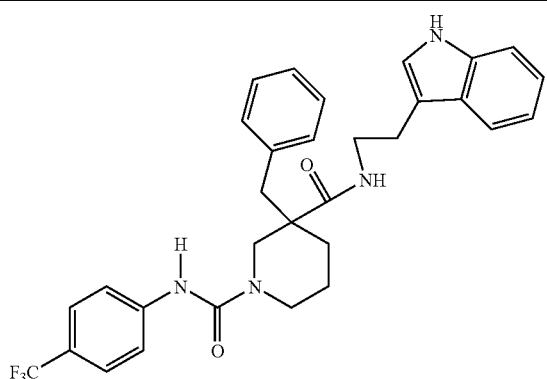
20
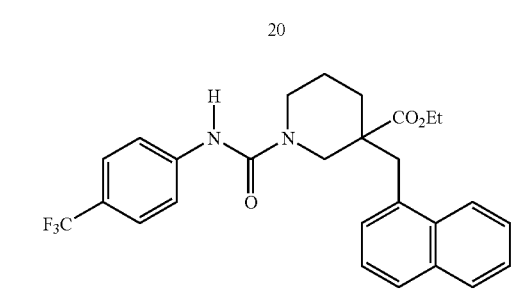
21
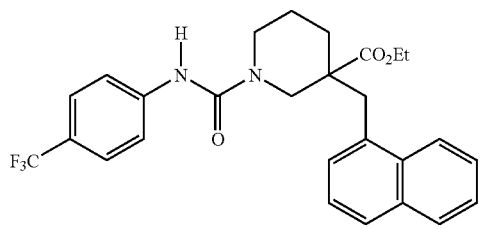 [SMILES: CCOC(=O)C1(Cc2cccc3ccccc23)CCCN(C(=O)Nc2ccc(C(F)(F)F)cc2)C1]
22
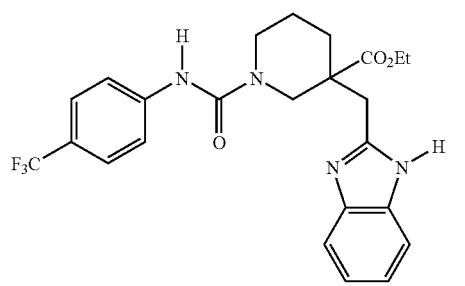 [SMILES: CCOC(=O)C1(Cc2nc3ccccc3[nH]2)CCCN(C(=O)Nc2ccc(C(F)(F)F)cc2)C1]
23
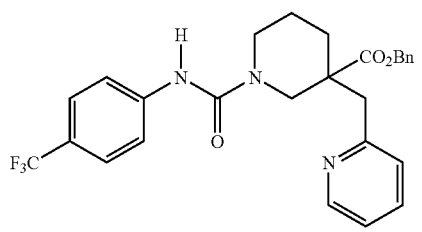 [SMILES: O=C(Nc1ccc(C(F)(F)F)cc1)N1CCCC(Cc2ccccn2)(C(=O)OCc2ccccc2)C1]
24
TABLE 1-continued
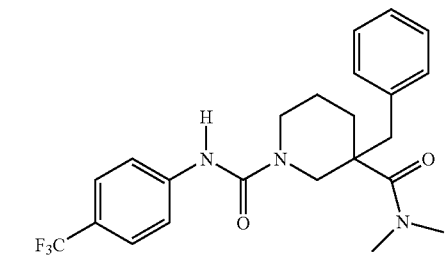 [SMILES: CN(C)C(=O)C1(Cc2ccccc2)CCCN(C(=O)Nc2ccc(C(F)(F)F)cc2)C1]
25
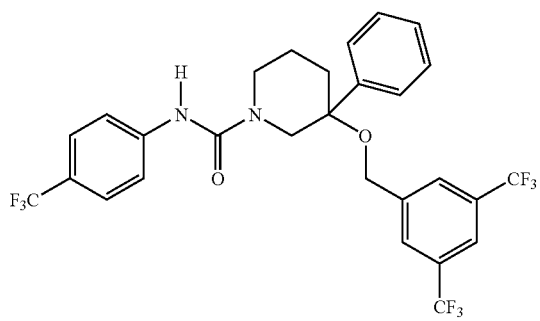 [SMILES: O=C(Nc1ccc(C(F)(F)F)cc1)N1CCCC(OCc2cc(C(F)(F)F)cc(C(F)(F)F)c2)(c2ccccc2)C1]
26
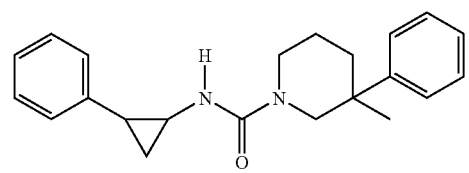 [SMILES: CC1(c2ccccc2)CCCN(C(=O)NC2CC2c2ccccc2)C1]
27
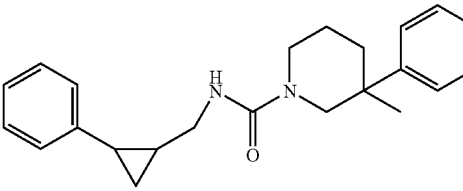
28
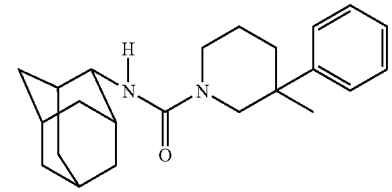 [SMILES: CC1(c2ccccc2)CCCN(C(=O)NC2C3CC4CC(C3)CC2C4)C1]
29

TABLE 1-continued
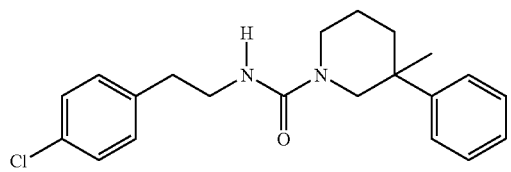 [SMILES: CC1(c2ccccc2)CCCN(C(=O)NCCc2ccc(Cl)cc2)C1]
30
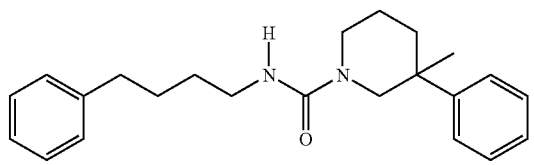 [SMILES: CC1(c2ccccc2)CCCN(C(=O)NCCCCc2ccccc2)C1]
31
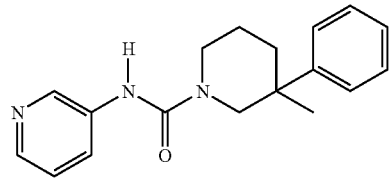 [SMILES: CC1(c2ccccc2)CCCN(C(=O)Nc2cccnc2)C1]
32
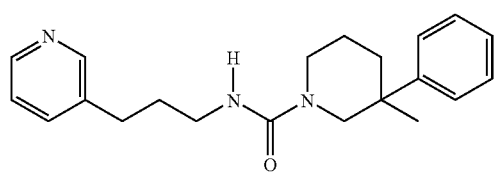 [SMILES: CC1(c2ccccc2)CCCN(C(=O)NCCCc2cccnc2)C1]
33
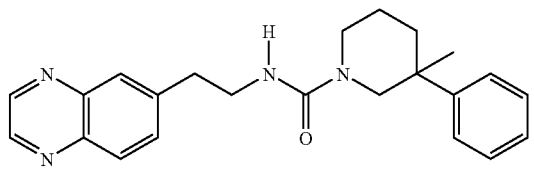 [SMILES: CC1(c2ccccc2)CCCN(C(=O)NCCc2ccc3nccnc3c2)C1]
34
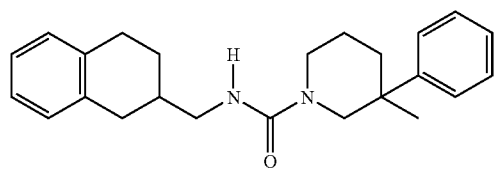 [SMILES: CC1(c2ccccc2)CCCN(C(=O)NCC2CCc3ccccc3C2)C1]
35
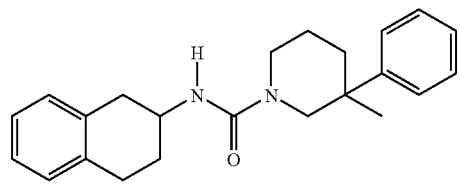 [SMILES: CC1(c2ccccc2)CCCN(C(=O)NC2CCc3ccccc3C2)C1]
36
TABLE 1-continued
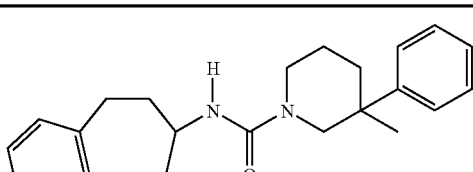
37
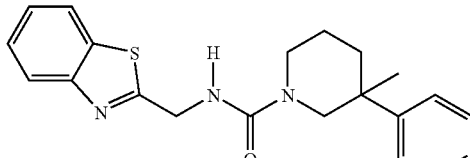
38
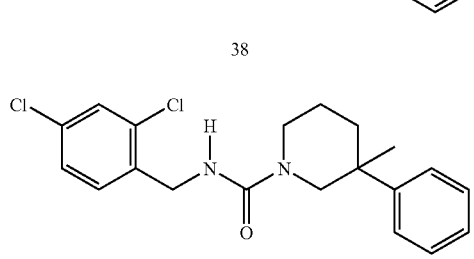
39
40
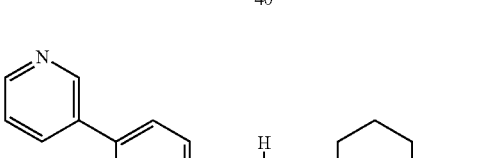
41
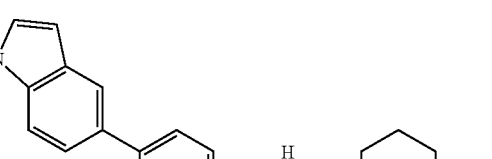
42

TABLE 1-continued
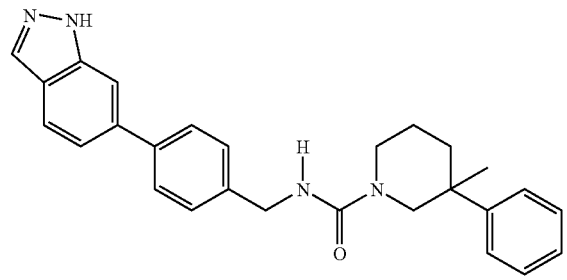
43
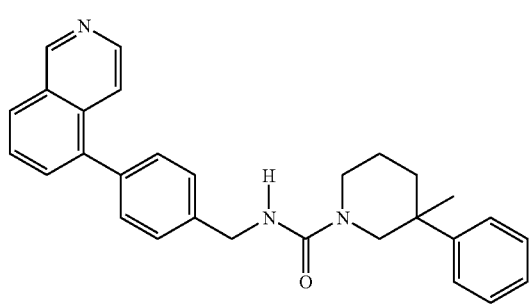
44
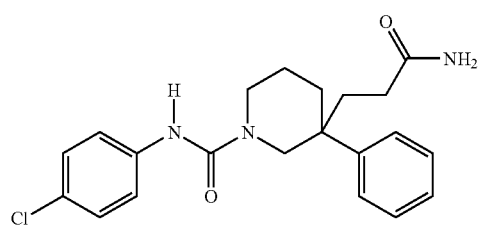
45
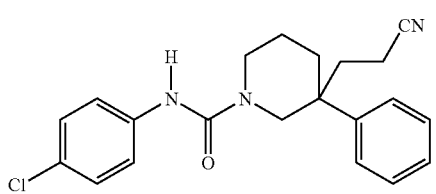
46
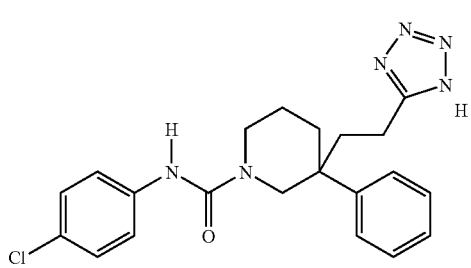
47
TABLE 1-continued
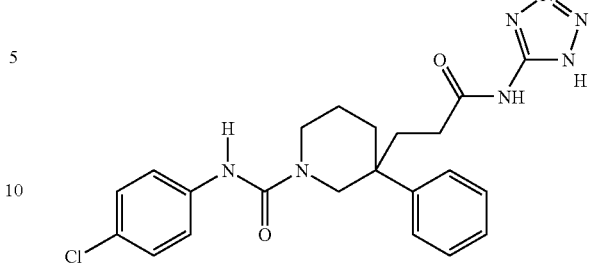
48
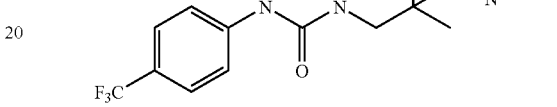
49
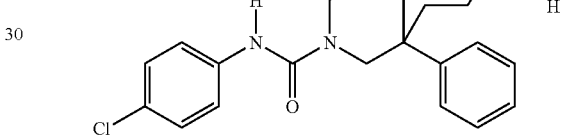
50
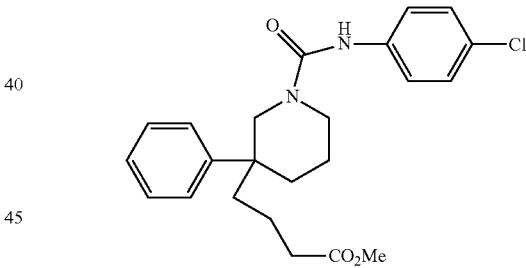
51
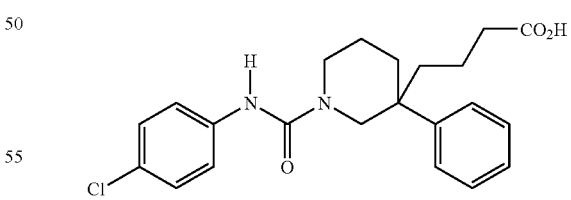
52
as well as the pharmaceutically acceptable salts and solvates thereof.
Yet another aspect of the invention that is of interest relates to a pharmaceutical composition comprised of a compound of formula I or a pharmaceutically acceptable salt or solvate thereof in combination with a pharmaceutically acceptable carrier.

Yet another aspect of the invention that is of interest relates to a method of treating diabetes in a mammalian patient in need of such treatment comprising administering to the patient a compound of formula I or a pharmaceutically acceptable salt or solvate thereof in an amount that is effective for treating diabetes.

Yet another aspect of the invention that is of interest relates to a method of treating pain in a mammalian patient in need of such treatment comprising administering to the patient a compound of formula I or a pharmaceutically acceptable salt or solvate thereof in an amount that is effective for treating pain.

Yet another aspect of the invention that is of interest relates to a method of treating atherosclerosis in a mammalian patient in need of such treatment comprising administering to the patient a compound of formula I or a pharmaceutically acceptable salt or solvate thereof in an amount that is effective for treating atherosclerosis.

Yet another aspect of the invention that is of interest relates to a method of treating hypertension in a mammalian patient in need of such treatment comprising administering to the patient a compound of formula I or a pharmaceutically acceptable salt or solvate thereof in an amount that is effective for treating hypertension.

Many of the compounds of formula I contain asymmetric centers and can thus occur as racemates and racemic mixtures, single enantiomers, diastereomeric mixtures and individual diastereomers. All such isomeric forms are included.

Moreover, chiral compounds possessing one stereocenter of general formula I, may be resolved into their enantiomers in the presence of a chiral environment using methods known to those skilled in the art. Chiral compounds possessing more than one stereocenter may be separated into their diastereomers in an achiral environment on the basis of their physical properties using methods known to those skilled in the art. Single diastereomers that are obtained in racemic form may be resolved into their enantiomers as described above.

If desired, racemic mixtures of compounds may be separated so that individual enantiomers are isolated. The separation can be carried out by methods well known in the art, such as the coupling of a racemic mixture of compounds of Formula I to an enantiomerically pure compound to form a diastereomeric mixture, which is then separated into individual diastereomers by standard methods, such as fractional crystallization or chromatography. The coupling reaction is often the formation of salts using an enantiomerically pure acid or base. The diasteromeric derivatives may then be converted to substantially pure enantiomers by cleaving the added chiral residue from the diastereomeric compound.

The racemic mixture of the compounds of Formula I can also be separated directly by chromatographic methods utilizing chiral stationary phases, which methods are well known in the art.

Alternatively, enantiomers of compounds of the general Formula I may be obtained by stereoselective synthesis using optically pure starting materials or reagents.

Some of the compounds described herein exist as tautomers, which have different points of attachment for hydrogen accompanied by one or more double bond shifts. For example, a ketone and its enol form are keto-enol tautomers. Or for example, a 2-hydroxyquinoline can reside in the tautomeric 2-quinolone form. The individual tautomers as well as mixtures thereof are included.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a weekly dosage of from about 0.05 milligrams to about 100 milligrams per kilogram of animal body weight, preferably given as a weekly dose, or in sustained release form. For most large mammals, including humans (e.g. a 70 kg adult), the total weekly dosage administered once weekly is from about 0.1 milligrams to about 1000 milligrams, is likely to be from about 0.5 milligrams to about 350 milligrams, and is often from about 1 milligram to about 50 milligrams. For a particularly potent compound, the dosage for an adult human may be as low as 0.1 mg. Examples of weekly dosages for a 70 kg adult human are 0.1 mg, 0.5 mg, 1 mg, 2 mg, 5 mg, 10 mg, 25 mg, 50 mg, 100 mg, 150 mg, 200 mg, 250 mg, 350 mg, and 500 mg per day. The dosage regimen may be adjusted within the above ranges or even outside of these ranges to provide the optimal therapeutic response.

Oral administration will usually be carried out using tablets. Examples of doses in tablets which may be administered once weekly include about 0.1 mg, 0.5 mg, 1 mg, 2 mg, 5 mg, 10 mg, 25 mg, 50 mg, 100 mg, 150 mg, 200 mg, 250 mg, 350 mg, and 500 mg. Other oral forms (e.g. capsules or suspensions) can also be administered in doses having similar sizes.

Dosing can be carried out on a daily basis, such as once, twice or three times daily, or less often, such as every other day, every third day, once weekly or even once monthly.

Combination Therapy

Compounds of Formula I may be used in combination with other drugs that may also be useful in the treatment or amelioration of one or more of the diseases or conditions for which compounds of Formula I are useful. Such other drugs may be administered, by a route and in an amount commonly used therefore, contemporaneously (such as via co-administration) or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, such as the glitazones (e.g. troglitazone, pioglitazone, englitazone, MCC-555, rosiglitazone, balaglitazone, netoglitazone, and the like), and PPAR gamma agonists and partial agonists that do not have a glitazone structure (e.g. K-111, INT-131, MBX-102 [metaglidisen], MBX-2044, FK614 including SPPARγM GSK-376501 and the like);

(b) biguanides such as metformin and phenformin;

(c) protein tyrosine phosphatase-1B (PTP-1B) inhibitors, (d) dipeptidyl peptidase IV (DPP-4) inhibitors, including sitagliptin, vildagliptin, saxagliptin, as well as those disclosed in the following published patents and applications: U.S. Pat. No. 6,699,871; U.S. Pat. No. 7,101,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-4 inhibitor compounds include isoleucine thiazolidide (P32/98); NVP-DPP-728; vildagliptin (LAF 237); P93/01; and saxagliptin (BMS 477118).

Additional specific DPP-IV inhibitors that are of interest herein include: (2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5S)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-2-(2,5-difluorophenyl)tetrahydro)-5-(4,6-dihydropyrrolo[3,4-c]pyrazol-5(1H)-yl)tetrahydro-2H-pyran-3-amine;

(2R,3S,5S)-2-(2,5-difluorophenyl)tetrahydro)-5-(4,6-dihydropyrrolo[3,4-c]pyrazol-5(1H)-yl)tetrahydro-2H-pyran-3-amine;

2R,3S,5R)-2-(2,4,5-trifluorophenyl)tetrahydro)-5-(4,6-dihydropyrrolo[3,4-c]pyrazol-5(1H)-yl)tetrahydro-2H-pyran-3-amine; and (2R,3S,5S)-2-(2,4,5-trifluorophenyl)tetrahydro)-5-(4,6-dihydropyrrolo[3,4-c]pyrazol-5(1H)-yl)tetrahydro-2H-pyran-3-amine;

(e) insulin or insulin mimetics, including rapid acting insulin, regular insulin, long acting insulin, complexed forms of insulin and the like, administered by any conventional route, such as subcutaneous, intradermal or intramuscular injection, oral, transdermal, intranasal, intrapulmonary, and the like;

(f) insulin secretagogues, such as sulfonylureas (e.g. tolbutamide, glimepiride, glicazinde, and glipizide) and meglitinides (e.g. repaglinide and nateglinide);

(g) α-glucosidase inhibitors (such as acarbose and miglitol);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid (niacin) or a salt thereof; (iv) niacin receptor agonists, (v) PPARα agonists such as fenofibric acid derivatives (gemfibrozil, clofibrate, fenofibrate and bezafibrate), (vi) cholesterol absorption inhibitors, such as for example ezetimibe, (vii) acyl CoA:cholesterol acyltransferase (ACAT) inhibitors, such as avasimibe, (viii) CETP inhibitors, such as torcetrapib, JTT-705, and compounds disclosed in WO2005/100298, WO2006/014357, and WO2006/014413, and (ix) phenolic anti-oxidants, such as probucol;

(i) antiobesity compounds such as fenfluramine, dexfenfluramine, phentiramine, sibutramine, orlistat, exentin-4 neuropeptideY5 inhibitors, Mc4r agonists, cannabinoid receptor 1 (CB-1) antagonists/inverse agonists, such as rimonabant and taranabant, and $\beta_3$ adrenergic receptor agonists;

(j) ileal bile acid transporter inhibitors;

(k) agents intended for use in inflammatory conditions such as aspirin, non-steroidal anti-inflammatory drugs as further described below, glucocorticoids, azulfidine, and cyclooxygenase 2 selective inhibitors;

(l) glucagon receptor antagonists;

(m) GLP-1;

(n) GIP-1; and (o) GLP-1 analogs, such as exendins, including exenatide;

(p) GPR 119 agonists;

(q) 11-B HSD 1 inhibitors;

(r) glucokinase activators;

(s) PPARδ agonists such as those disclosed in WO 97/28149;

(t) prandial glucose releasing agents such as repaglinide and nateglinide, (u) antihypertensives, such as diuretics, e.g., hydrochlorothiazide, furosemide and the like; beta adrenergic blocking drugs, such as propranolol, metaprolol and the like; ACE inhibitors, such as enalapril, lisinopril, ramipril, quinapril and the like, ARBs, such as losartan, valsartan, irbesartan, candesartan and the like, and calcium channel blocking drugs, such as amlodipine, diltiazem and verapamil; and (v) NSAIDS such as ibuprofen, naproxen, meloxicam, diclofenac, indomethacin, piroxicam, COX-2 inhibitors such as nabumetone, etodolac, rofecoxib, etoricoxib, celecoxib, and valdecoxib, and conventional non-opioid and opioid analgesics, such as aspirin, acetaminophen, codeine, meperidine, oxycodone, hydrocodone, pentazocine, morphine and the like.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DPP-4 inhibitors, and anti-obesity compounds.

Examples of glucagon receptor antagonist compounds that are useful as described herein include: N-[4-((1S)-1-{3-(3,5-Dichlorophenyl)-5-[6-(trifluoromethoxy)-2-naphthyl]-1H-pyrazol-1-yl}ethyl)benzoyl]-β-alanine;

N-[4-((1R)-1-{3-(3,5-Dichlorophenyl)-5-[6-(trifluoromethoxy)-2-naphthyl]-1H-pyrazol-1-yl}ethyl)benzoyl]-β-alanine;

N-(4-{1-[3-(2,5-dichlorophenyl)-5-(6-methoxy-2-naphthyl)-1H-pyrazol-1-yl]ethyl}benzoyl)-β-alanine;

N-(4-{(1S)-1-[3-(3,5-Dichlorophenyl)-5-(6-methoxy-2-naphthyl)-1H-pyrazol-1-yl]ethyl}benzoyl)-β-alanine;

3-({4-[(2S)-2-({5-chloro-1-[3-(trifluoromethyl)phenyl]-1H-indol-2-yl}carbonyl)heptyl]benzoyl}amino)propanoic acid and 3-({4-[(2R)-2-({5-chloro-1-[3-(trifluoromethyl)phenyl]-1H-indol-2-yl}carbonyl)heptyl]benzoyl}amino)propanoic acid;

3-[(3-Bromo-4-{(2S)-2-[(5-chloro-1-methyl-1H-indol-2-yl)carbonyl]heptyl}benzoyl)amino]propanoic acid and 3-[(3-Bromo-4-{(2R)-2-[(5-chloro-1-methyl-1H-indol-2-yl)carbonyl]heptyl}benzoyl)amino]propanoic acid;

3-{[4-((2R)-2-{[1-(4-tert-butylbenzyl)-5-chloro-1H-indol-2-yl]carbonyl}pentyl)benzoyl]amino}propanoic acid and 3-{[4-((2S)-2-{[1-(4-tert-butylbenzyl)-5-chloro-1H-indol-2-yl]carbonyl}pentyl)benzoyl]amino}propanoic acid;

3-{[4-((2R)-2-{[5-Chloro-1-(3,5-dichlorophenyl)-1H-indol-2-yl]carbonyl}pentyl)benzoyl]amino}propanoic acid and 3-{[4-((2S)-2-{[5-Chloro-1-(3,5-dichlorophenyl)-1H-indol-2-yl]carbonyl}pentyl)benzoyl]amino}propanoic acid;

N-(4-{(1S)-1-[3-[2-Ethoxy-5-(trifluoromethyl)phenyl]-5-(6-methoxy-2-naphthyl)-1H-pyrazol-1-yl]ethyl}benzoyl)-β-alanine;

N-(4-{(1S)-1-[3-[2-methoxy-5-(trifluoromethyl)phenyl]-5-(6-methoxy-2-naphthyl)-1H-pyrazol-1-yl]ethyl}benzoyl)-β-alanine;

N-[4-((1S)-1-{5-(6-methoxy-2-naphthyl)-3-[2-methoxy-5-(trifluoromethyl)phenyl]-1H-pyrazol-1-yl}pentyl)benzoyl]-β-alanine;

N-[4-((1S)-1-{5-(6-chloro-2-naphthyl)-3-[2-methoxy-5-(trifluoromethyl)phenyl]-1H-pyrazol-1-yl}pentyl)benzoyl]-β-alanine;

N-(4-{(1S)-1-[(R)-(4-chlorophenyl)(7-fluoro-5-methyl-1H-indol-3-yl)methyl]butyl}benzoyl)-β-alanine;

N-(4-{1-[(4-chlorophenyl)(5,7-dichloro-1H-indol-3-yl)methyl]butyl}benzoyl)-β-alanine;

N-(4-{1-[(3-chloro-4-methoxyphenyl)(5,7-dichloro-1H-indol-3-yl)methyl]pentyl}benzoyl)-β-alanine; and N-(4-{1-[(5,7-dichloro-1H-indol-3-yl)(3,5-dichloro-4-methoxyphenyl)methyl]pentyl}benzoyl)-β-alanine.

Examples of GPR-119 agonists that are of interest as described herein include

4-Methyl-6-[1'-(5-methylpyrazin-2-yl)-4,4'-bipiperidin-1-yl]pyrimidine-2-carbonitrile;

1-(5-chloropyrazin-2-yl)-1'-[5-(methylsulfonyl)pyridin-2-yl]-4,4'-bipiperidine;

2-chloro-4-(1'-pyrimidin-2-yl-4,4'-bipiperidin-1-yl)benzonitrile and 1-(5-chloro-2-methylpyrimidin-4-yl)-1'-(5-chloropyrimidin-2-yl)-4,4'-bipiperidine.

Also claimed is the use of additional PPAR alpha, gamma or delta selective agonists, PPAR alpha/gamma, gamma/delta, alpha/delta dual agonists, or PPAR alpha/gamma/delta pan agonists on a once weekly basis. These agents are useful for the treatment of diabetes, dyslipidemia and weight loss. Examples of such agents include, but are not limited to the following: netoglitazone, pioglitazone, rosiglitazone, troglitazone, balaglitazone, CS204, AZD6610, ZYH1, GFT505, LY-465608, DRF-2519, DRF-11605, DRF-2725, GW-626019, GW-625019, CS038, ONO-5129, aleglitazar, muraglitazar, soldeglitazar, teseglitazar, naveglitazar, farglitazar, KRP-297, AVE0897, AVE 0847, LBM642, PPM263, PPM202, PPM201, PPM204, PLX-204, GW-677954, NN0606, AVE8134, NS-220, SAR 35034, KD3010, GW-501516, FK614, K-111, metaglidasen, MBX-2044, INT-131, KD3010, KR-62980, SVT002149, AVE8134, AVE5378, AVE0897, SAR35034, AVE5376, MBX2130, PAT-5A, GW-501516, GW-1262570, GW677954, GW590735, R-483, and BAY-54-9801.

Examples of SPPARMs that are of interest as described herein include:

(2S)-2-({6-chloro-3-[6-(4-chlorophenoxy)-2-propylpyridin-3-yl]-1,2-benzisoxazol-5-yl}oxy)propanoic acid;

(2S)-2-({6-chloro-3-[6-(4-fluorophenoxy)-2-propylpyridin-3-yl]-1,2-benzisoxazol-5-yl}oxy)propanoic acid;

(2S)-2-{[6-chloro-3-(6-phenoxy-2-propylpyridin-3-yl)-1,2-benzisoxazol-5-yl]oxy}propanoic acid;

(2R)-2-({6-chloro-3-[6-(4-chlorophenoxy)-2-propylpyridin-3-yl]-1,2-benzisoxazol-5-yl}oxy)propanoic acid;

(2R)-2-{3-[3-(4-methoxy)benzoyl-2-methyl-6-(trifluoromethoxy)-1H-indol-1-yl]phenoxy}butanoic acid;

(2S)-2-{3-[3-(4-methoxy)benzoyl-2-methyl-6-(trifluoromethoxy)-1H-indol-1-yl]phenoxy}butanoic acid;

2-{3-[3-(4-methoxy)benzoyl-2-methyl-6-(trifluoromethoxy)-1H-indol-1-yl]phenoxy}-2-methylpropanoic acid; and (2R)-2-{3-[3-(4-chloro)benzoyl-2-methyl-6-(trifluoromethoxy)-1H-indol-1-yl]phenoxy}propanoic acid.

Examples of 11B-HSD 1 inhibiting compounds that are of interest as described herein include:

3-[1-(4-chlorophenyl)-trans-3-fluorocyclobutyl]-4,5-dicyclopropyl-r-4H-1,2,4-triazole;

3-[1-(4-chlorophenyl)-trans-3-fluorocyclobutyl]-4-cyclopropyl-5-(1-methylcyclopropyl)-r-4H-1,2,4-triazole;

3-[1-(4-chlorophenyl)-trans-3-fluorocyclobutyl]-4-methyl-5-[2-(trifluoromethoxy)phenyl]-r-4H-1,2,4-triazole;

3-[1-(4-chlorophenyl)cyclobutyl]-4-methyl-5-[2-(trifluoromethyl)phenyl]-4H-1,2,4-triazole;

3-{4-[3-(Ethylsulfonyl)propyl]bicyclo[2.2.2]oct-1-yl}-4-methyl-5-[2-(trifluoromethyl)phenyl]-4H-1,2,4-triazole;

4-Methyl-3-{4-[4-(methylsulfonyl)phenyl]bicyclo[2.2.2]oct-1-yl}-5-[2-(trifluoromethyl)phenyl]-4H-1,2,4-triazole;

3-(4-{4-Methyl-5-[2-(trifluoromethyl)phenyl]-4H-1,2,4-triazol-3-yl}bicyclo[2.2.2]oct-1-yl)-5-(3,3,3-trifluoropropyl)-1,2,4-oxadiazole;

3-(4-{4-Methyl-5-[2-(trifluoromethyl)phenyl]-4H-1,2,4-triazol-3-yl}bicyclo[2.2.2]oct-1-yl)-5-(3,3,3-trifluoroethyl)-1,2,4-oxadiazole;

5-(3,3-Difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

5-(1-Fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

2-(1,1-Difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;

2-(3,3-Difluorocyclobutyl)-5-(4-{4-methyl-5-[2-(trifluoromethyl)phenyl]-4H-1,2,4-triazol-3-yl}bicyclo[2.2.2]oct-1-yl-1,3,4-oxadiazole; and 5-(1,1-Difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole.

Examples of glucokinase activating drugs that are of interest for use as described herein include:

6-(1-acetylpyrrolidin-2-yl)-5-(6-methoxymethylpyridin-3-yl)oxy)-2-pyridin-2-yl-1H-benzimidazole 6-(1-acetylpyrrolidin-2-yl)-5-((6-methylpyridin-3-yl)oxy)-2-pyridin-2-yl-1H-benzimidazole, 6-(1-acetylpyrrolidin-2-yl)-5-((6-pyrazin-2-ylpyridin-3-yl)oxy)-2-pyridin-2-yl-1H-benzimidazole, 6-(1-acetyl-3-fluoropyrrolidin-2-yl)-5-((2'-fluorobiphenyl-4-yl)oxy)-2-pyridin-2-yl-1H-benzimidazole, 3-(6-ethanesulfonyl-pyridin-3-yloxy)-5-(2-hydroxy-1-methyl-ethoxy)-N-(1-methyl-1H-pyrazol-3-yl)benzamide;

3-(6-ethanesulfonyl-pyridin-3-yloxy)-5-isopropoxy-N-(1-methyl-1H-pyrazol-3-yl)benzamide;

5-(2-fluoro-1-fluoromethyl-ethoxy)-3-(6-methanesulfonyl-pyridin-3-yloxy)-N-(1-methyl-1H-pyrazol-3-yl)benzamide;

3-(6-ethanesulfonyl-pyridin-3-yloxy)-5-(2-hydroxy-1-methyl-ethoxy)-N-(isoxazol-3-yl)benzamide;

1-[(5-{[6-(5-methyl-1,2,4-oxadiazol-3-yl)-3-pyridinyl]oxy}-2-(2-pyridinyl)-1H-benzimidazol-6-yl)methyl]-2-pyrrolidinone, N-({5-[4-(ethylsulfonyl)phenoxy]-2-(2-pyridinyl)-1H-benzimidazol-6-yl}methyl)-N-methylacetamide, 3-{[5-[4-(5-methyl-1,2,4-oxadiazol-3-yl)phenoxy]-2-(2-pyridinyl)-1H-benzimidazol-6-yl]methyl}-1,3-oxazolidine-2,4-dione, 5-[4-(ethylsulfonyl)phenoxy]-6-((2-methyl-2H-tetrazol-5-yl)methyl)-2-(2-pyridinyl)-1H-benzimidazole, 3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide;

3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide;

3-{[4-(2-methoxyethoxy)phenyl]thio}-N-(3-methyl-1,2,4-thiadiazol-5-yl)-6-[(4-methyl-4H-1,2,4-triazol-3-yl)thio]pyridine-2-carboxamide; and 3-[(4-acetylphenyl)thio]-N-(3-methyl-1,2,4-thiadiazol-5-yl)-6-[(4-methyl-4H-1,2,4-triazol-3-yl)thio]pyridine-2-carboxamide.

Compounds of the present invention (i.e. compounds having Formula I) can be used to treat one or more diseases or conditions selected from hypercholesterolemia, atherosclerosis, low HDL levels, high LDL levels, hyperlipidemia, hypertriglyceridemia, and dyslipidemia by administering a therapeutically effective amount of a compound of claim 1 in combination with an HMG-CoA reductase inhibitor to a patient in need of such treatment. Statins are the preferred HMG-CoA reductase inhibitors for use in this combination therapy. Preferred statins include lovastatin, simvastatin, pravastatin, fluvastatin, atorvastatin, itavastatin, ZD-4522, rivastatin, and rosuvastatin. This combination treatment may be particularly desirable for treating or reducing the risk of developing atherosclerosis. Such a combination can optionally have a third pharmaceutically active ingredient, such as a CETP inhibitor (e.g. torcetrapib), niacin, or a cholesterol absorption inhibitor (e.g. ezetimibe).

Cholesterol absorption inhibitors can also be used in the present invention. Such compounds block the movement of cholesterol from the intestinal lumen into enterocytes of the small intestinal wall, thus reducing serum cholesterol levels. Examples of cholesterol absorption inhibitors are described in U.S. Pat. Nos. 5,846,966, 5,631,365, 5,767,115, 6,133,001, 5,886,171, 5,856,473, 5,756,470, 5,739,321, 5,919,672, and in PCT application Nos. WO 00/63703, WO 00/60107, WO 00/38725, WO 00/34240, WO 00/20623, WO 97/45406, WO 97/16424, WO 97/16455, and WO 95/08532. The most notable cholesterol absorption inhibitor is ezetimibe, also known as 1-(4-fluorophenyl)-3(R)-[3(S)-(4-fluorophenyl)-3-hydroxypropyl)]-4(S)-(4-hydroxyphenyl)-2-azetidinone, described in U.S. Pat. Nos. 5,767,115 and 5,846,966.

Therapeutically effective amounts of cholesterol absorption inhibitors include dosages of from about 0.01 mg/kg to about 30 mg/kg of body weight per day, preferably about 0.1 mg/kg to about 15 mg/kg.

For diabetic patients, the compounds used in the present invention can be administered with conventional diabetic medications as outlined above. For example, a diabetic patient receiving treatment as described herein may also be taking insulin or an oral antidiabetic medication. One example of an oral antidiabetic medication useful herein is metformin.

For hypertensive patients, the compounds used in the present invention can be administered with conventional antihypertensive medications as outlined above. For example, a patient with high blood pressure receiving treatment as described herein may also be taking ARBS or an ACE inhibitor. One example of an oral antihypertensive medication useful herein is losartin.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic or has a basic group in the structure, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Preferred acids include citric, hydrobromic, hydrochloric, maleic, phosphoric, sulfuric, tartaric, toluenesulfonic (tosylate), methanesulfonic (mesylate) and benzenesulfonic (besylate) acid salts, most preferably the benzenesulfonic, toluenesulfonic and methanesulfonic acid salts. In some instances the compounds of the invention may be present in zwitterionic forms.

It will be understood that, as used herein, references to the compounds of Formula I are meant to also include the pharmaceutically acceptable salts.

Metabolites—Prodrugs

Metabolites of the claimed compounds which themselves fall within the scope of the claimed invention are also compounds of the current invention. Prodrugs, which are metabolically or physically labile compounds that are converted to the claimed active pharmaceutical ingredient as they are being administered to a patient or after they have been administered to a patient, also may be considered compounds of this invention.

Pharmaceutical Compositions

The pharmaceutical compositions described herein are generally comprised of a compound of formula I or a pharmaceutically acceptable salt or solvate thereof, in combination with a pharmaceutically acceptable carrier.

The compounds used in the present invention can be administered via any conventional route of administration. The preferred route of administration is oral. Examples of suitable oral compositions include tablets, capsules, troches, lozenges, suspensions, dispersible powders or granules, emulsions, syrups and elixirs. Examples of carrier ingredients include diluents, binders, disintegrants, lubricants, sweeteners, flavors, colorants, preservatives, and the like. Examples of diluents include, for example, calcium carbonate, sodium carbonate, lactose, calcium phosphate and sodium phosphate. Examples of granulating and disintegrants include corn starch and alginic acid. Examples of binding agents include starch, gelatin and acacia. Examples of lubricants include magnesium stearate, calcium stearate, stearic acid and talc. The tablets may be uncoated or coated by known techniques. Such coatings may delay disintegration and thus, absorption in the gastrointestinal tract and thereby provide a sustained action over a longer period.

One embodiment of the invention that is of interest is a tablet or capsule that is comprised of a compound of formula I or a pharmaceutically acceptable salt or solvate thereof in an amount ranging from about 0.1 mg to about 1000 mg, in combination with a pharmaceutically acceptable carrier.

In another embodiment of the invention, a compound of formula I or a pharmaceutically acceptable salt or solvate thereof is combined with another therapeutic agent and the carrier to form a fixed combination product. This fixed combination product may be a tablet or capsule for oral use.

More particularly, in another embodiment of the invention, a compound of formula I or a pharmaceutically acceptable salt or solvate thereof (about 0.1 to about 1000 mg) and the second therapeutic agent (about 0.1 to about 500 mg) are combined with the pharmaceutically acceptable carrier, providing a tablet or capsule for oral use.

Sustained release over a longer period of time may be particularly important in the formulation. A time delay material such as glyceryl monostearate or glyceryl distearate may be employed. The dosage form may also be coated by the techniques described in the U.S. Pat. Nos. 4,256,108; 4,166,452 and 4,265,874 to form osmotic therapeutic tablets for controlled release.

Other controlled release technologies are also available and are included herein. Typical ingredients that are useful to slow the release of nicotinic acid in sustained release tablets include various cellulosic compounds, such as methylcellulose, ethylcellulose, propylcellulose, hydroxypropylcellulose, hydroxyethylcellulose, hydroxypropylmethylcellulose, microcrystalline cellulose, starch and the like. Various natural and synthetic materials are also of use in sustained release formulations. Examples include alginic acid and various alginates, polyvinyl pyrrolidone, tragacanth, locust bean gum, guar gum, gelatin, various long chain alcohols, such as cetyl alcohol and beeswax.

Optionally and of even more interest is a tablet as described above, comprised of a compound of formula I or a pharmaceutically acceptable salt or solvate thereof, and further containing an HMG Co-A reductase inhibitor, such as simvastatin or atorvastatin.

Typical release time frames for sustained release tablets in accordance with the present invention range from about 1 to as long as about 48 hours, preferably about 4 to about 24 hours, and more preferably about 8 to about 16 hours.

Hard gelatin capsules constitute another solid dosage form for oral use. Such capsules similarly include the active ingredients mixed with carrier materials as described above. Soft gelatin capsules include the active ingredients mixed with water-miscible solvents such as propylene glycol, PEG and ethanol, or an oil such as peanut oil, liquid paraffin or olive oil.

Aqueous suspensions are also contemplated as containing the active material in admixture with excipients suitable for the manufacture of aqueous suspensions. Such excipients include suspending agents, for example sodium carboxymethylcellulose, methylcellulose, hydroxypropylmethylcellulose, sodium alginate, polyvinylpyrrolidone, tragacanth and acacia; dispersing or wetting agents, e.g., lecithin; preservatives, e.g., ethyl, or n-propyl para-hydroxybenzoate, colorants, flavors, sweeteners and the like.

Dispersible powders and granules suitable for preparation of an aqueous suspension by the addition of water provide the active ingredients in admixture with a dispersing or wetting agent, suspending agent and one or more preservatives. Suitable dispersing or wetting agents and suspending agents are exemplified by those already mentioned above.

Syrups and elixirs are also included.

More particularly, a pharmaceutical composition that is of interest is a sustained release tablet that is comprised of a compound of formula I or a pharmaceutically acceptable salt or solvate thereof in combination with a pharmaceutically acceptable carrier.

Another aspect of the invention relates to the use of a compound of formula I or a pharmaceutically acceptable salt or solvate thereof in the manufacture of a medicament. This medicament has the uses described herein.

More particularly, another aspect of the invention relates to the use of a compound of formula I or a pharmaceutically acceptable salt or solvate thereof, and an HMG Co-A reductase inhibitor, such as simvastatin, in the manufacture of the medicament. This medicament has the uses described herein.

Utilities

The compounds defined above may be used in any of the following methods to treat or control diseases, as well as methods to treat other diseases not listed below, in a mammalian patient, especially a human, by administering to the patient a therapeutically effective amount for the specific disease (or diseases) of a compound of Formula I:

(1) insulin dependent (type 1 diabetes) and non-insulin dependent diabetes mellitus (type 2 diabetes);
(2) pre-diabetes (insulin resistance);
(3) hyperglycemia;
(4) metabolic syndrome;
(5) obesity;
(6) atherosclerosis;
(7) hypertension;
(8) one or more lipid disorders, including mixed or diabetic dyslipidemia, hyperlipidemia, and hypercholesterolemia;
(9) glaucoma, age related macular degeneration and the like;
(10) organ protection, such as protection from reperfusion injury; and
(11) kidney malfunction, such as proteinuria, and in particular, albuminuria, and subsequent edema resulting therefrom, macrophage infiltration, and the like.

The compounds may also be used in a method for reducing the risks of adverse sequelae associated with metabolic syndrome in a human or other mammalian patient in need of such treatment which comprises administering to the patient once weekly a therapeutically effective amount of a compound of Formula I, or a pharmaceutically acceptable salt thereof.

The compounds may also be used in a method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient a therapeutically effective amount of a compound of Formula I. Sequelae of atherosclerosis include for example angina, claudication, heart attack, stroke, etc.

The compounds are especially useful in the treatment of the following diseases, by administering a therapeutically effective amount (for the specific disease) of the compound, or a pharmaceutically acceptable salt thereof, to a patient in need of treatment:

(1) type 2 diabetes, and especially insulin resistance resulting from type 2 diabetes;
(2) hypertension;
(3) atherosclerosis; and
(4) metabolic syndrome.

Another aspect of the invention that is of interest relates to a method of treating atherosclerosis in a human patient in need of such treatment comprising administering to the patient a compound of formula I or a pharmaceutically acceptable salt or solvate thereof in an amount that is effective for treating atherosclerosis.

Another aspect of the invention that is of interest relates to a method of treating diabetes, and in particular, type 2 diabetes, in a human patient in need of such treatment comprising administering to the patient a compound of formula I or a pharmaceutically acceptable salt or solvate thereof in an amount that is effective for treating diabetes.

Another aspect of the invention that is of interest relates to a method of treating metabolic syndrome in a human patient in need of such treatment comprising administering to the patient a compound of formula I or a pharmaceutically acceptable salt or solvate thereof in an amount that is effective for treating metabolic syndrome.

Another aspect of the invention that is of interest relates to a method of treating high blood pressure in a human patient in need of such treatment comprising administering to the patient a compound of formula I or a pharmaceutically acceptable salt or solvate thereof in an amount that is effective for treating hypertension.

Another aspect of the invention that is of interest relates to a method of treating inflammatory pain or CNS-mediated pain in a human patient in need of such treatment comprising administering to the patient a compound of formula I or a pharmaceutically acceptable salt or solvate thereof in an amount that is effective for treating pain.

Another aspect of the invention that is of interest relates to a method of treating disorders of the eye in a human patient in need of such treatment comprising administering to the patient a compound of formula I or a pharmaceutically acceptable salt or solvate thereof in an amount that is effective for alleviating eye disorders.

Another aspect of the invention that is of interest relates to a method of treating cardiac hypertrophy and renal failure in a human patient in need of such treatment comprising administering to the patient a compound of formula I or a pharmaceutically acceptable salt or solvate thereof in an amount that is effective for anti-inflammatory end organ protection.

Another aspect of the invention that is of particular interest relates to a method of treating or preventing atherosclerosis, diabetes, hypertension, metabolic syndrome or a related condition in a human patient in need of such treatment, comprising administering to the patient a compound of formula I or a pharmaceutically acceptable salt or solvate thereof administered in an amount that is effective to treat or prevent atherosclerosis, diabetes, hypertension, metabolic syndrome or a related condition.

Compounds of the present invention are inhibitors of the enzyme soluble epoxide hydrolase (sEH). The compounds of this invention are useful in treating or controlling diseases, disorders or conditions which are mediated by sEH. One aspect of the present invention provides a method for the treatment and control of diseases that can be mediated by administration of an sEH inhibitor, such as type 2 diabetes or hypertension. Compounds of the present invention may be useful in treating or controlling many sEH mediated diseases and conditions, including, but not limited to, (1) diabetes mellitus, and especially non-insulin dependent type 2 diabetes mellitus (NIDDM), (2) hyperglycemia, (3) low glucose tolerance, (4) pre-diabetes or insulin resistance, (5) obesity, (6) hypertension, (7) dyslipidemia, (8) hyperlipidemia, (9) hypercholesterolemia, (10) atherosclerosis and its sequelae, (11) kidney failure, (12) cardiac hypertrophy, (13) pancreatitis, (14) vascular restenosis, (15) inflammatory pain, (16) CNS-mediated pain, (17) glaucoma, (18) macular degeneration, (19) retinopathy, (20) thrombosis, (21) metabolic syndrome, and (22) Raynaud's syndrome.

Another aspect of the invention provides a method of treating inflammatory conditions, including adult respiratory distress syndrome (ARDS), ischemia/reperfusion injury and related diseases.

The present compounds can be used to lower glucose and insulin in non-diabetic patients who have impaired glucose tolerance and/or are in a pre-diabetic condition by the administration to a patient in need of treatment a therapeutically effective amount of a compound having Formula I, or pharmaceutically acceptable salt thereof.

The present compounds can be used to treat obesity in a patient in need of such treatment by administering to the patient a therapeutically effective amount of a compound of Formula I, or pharmaceutically acceptable salt thereof.

The present compounds can be used to treat or reduce the risk of developing atherosclerosis in a patient in need of such treatment by administering to the patient a therapeutically effective amount of a compound of Formula I, or a pharmaceutically acceptable salt thereof.

The present compounds can be used to treat or reduce hyperglycemia in a diabetic patient in need of such treatment by administering to the patient a therapeutically effective amount of a compound of Formula I, or a pharmaceutically acceptable salt thereof.

The present compounds can be used to treat or reduce blood pressure and provide kidney end organ protection in a hypertensive patient in need of such treatment by administering to the patient a therapeutically effective amount of a compound of Formula I, or a pharmaceutically acceptable salt thereof.

One aspect of the invention provides a method for the treatment and control of mixed or diabetic dyslipidemia, and/or atherosclerosis, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (such as torcetrapib), niacin, niacin receptor agonists, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL-c levels, and low HDL-c levels.

Another aspect of the invention that is of interest relates to a method of treating or controlling one or more of: mixed or diabetic dyslipidemia, hypercholesterolemia, atherosclerosis, low HDL levels, high LDL levels, hyperlipidemia, and/or hypertriglyceridemia, type 2 diabetes, hyperglycemia, insulin resistance and related conditions, hypertension, and/or kidney failure, and inflammatory pain which comprises administering to a patient in need of such treatment a therapeutically effective amount of a compound having formula I in combination with a compound selected from the group consisting of:

a DPP-4 antagonist; a glucagon receptor antagonist; a glucokinase activator; a GPR119 agonist; a GPR 40 modulator; a GPR 120 agonist; an insulin sensitizer; a sulfonylurea or other insulin secretagogue; a SPPARγM such as those disclosed in WO 2006/099077 A1; an α-glucosidase inhibitor; a GLP-1, GLP-1 analogue or mimetic or a GLP-1 receptor agonist; a GIP, GIP mimetic or GIP receptor agonist; a PACAP, a PACAP mimetic or PACAP receptor agonist; an HMG Co-A reductase inhibitor; a bile acid sequestrant; (niacin) nicotinic acid or a nicotinyl alcohol; a PPAR α agonist; a PPARα/γ dual agonist; a PPAR pan agonist; inhibitors of cholesterol absorption; acyl CoA:cholesterol acyltransferase inhibitors; antioxidants; PPARδ agonists; antiobesity agents such as NPY1 or NPY5 antagonists CB1 receptor inverse agonists, ileal bile acid transporter inhibitors; aspirin, NSAIDs, glucocorticoids, azulfidine, selective COX-2 inhibitors; antihypertensive agents such as ACE inhibitors, AII receptor blockers, beta blockers and calcium channel blocking drugs; diuretics; inhibitors of 11β-HSD-1; inhibitors of CETP and inhibitors of fructose 1,6-bisphosphatase.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy. In general, compositions suitable for oral administration are preferred.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form, in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.35 |
| Benzalkonium chloride | 1.0 | Magnesium Stearate | 2.5 |
| Water for injection | t.d. 1.0 mL | Total | 500 mg |

| Capsule | mg/capsule | Aerosol | Per Canister |
|---|---|---|---|
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoro-methane, NF | 12.15 g |

REPRESENTATIVE SCHEMES AND EXAMPLES

The following Schemes and Examples are provided to more fully illustrate the present invention. Representative compounds of Formula I have been prepared by the following reaction Schemes below. It is understood that other synthetic approaches to these structure classes are conceivable to one skilled in the art. Therefore these reaction Schemes, as well as the Examples, should not be construed as limiting the scope of the invention. Unless stated otherwise:

(i) all operations were carried out at room (rt) or ambient temperature, that is, at a temperature in the range 18-25° C.;

(ii) evaporation of solvent was carried out using a rotary evaporator under reduced pressure (4.5-30 mmHg) with a bath temperature of up to 50° C.;

(iii) the course of reactions was followed by thin layer chromatography (TLC) and/or tandem high performance liquid chromatography (HPLC) followed by mass spectroscopy (MS), herein termed LCMS, and any reaction times are given for illustration only;

(iv) yields, if given, are for illustration only;

(v) the structure of all final compounds was assured by at least one of the following techniques: MS or proton nuclear magnetic resonance (1H NMR) spectrometry, and the purity was assured by at least one of the following techniques: TLC or HPLC;

(vi) 1H NMR spectra were recorded on either a Varian Unity or a Varian Inova instrument at 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;

(vii) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; the method for LCMS ES+ was 1-2 mL/min, 10-95% B linear gradient over 5.5 min (B=0.05% TFA-acetonitrile, A=0.05% TFA-water), and the method for LCMS ES− was 1-2 mL/min, 10-95% B linear gradient over 5.5 min (B=0.1% formic acid–acetonitrile, A=0.1% formic acid–water), Waters XTerra C18—3.5 um-50×3.0 mmID and diode array detection;

(viii) automated purification of compounds by preparative reverse phase RP-HPLC was performed on a Gilson system using a YMC-Pack Pro C18 column (150×20 mm i.d.) eluting at 20 mL/min with 0-50% acetonitrile in water (0.1% TFA);

(ix) column chromatography was carried out on a glass silica gel column using Kieselgel 60, 0.063-0.200 mm (Merck), or a Biotage cartridge system;

(x) chemical symbols have their usual meanings; the following abbreviations have also been used v (volume), w (weight), b.p. (boiling point), m.p. (melting point), L (litre(s)), mL (millilitres), g (gram(s)), mg (milligrams(s)), mol (moles), mmol (millimoles), eq or equiv (equivalent(s)), IC50 (molar concentration which results in 50% of maximum possible inhibition), EC50 (molar concentration which results in 50% of maximum possible efficacy), uM (micromolar), nM (nanomolar);

(xi) definitions of acronyms are as follows:

| | |
|---|---|
| TMSN$_3$ is trimethylsilyl azide | EDCI is 1-(3-dimethylaminopropyl)-3-ethyl carbodiimide HCl |
| DCM is dichloromethane (methylene chloride) | HOBT is 1-hydroxy-benzotriazole |
| DMF is dimethylformamide | THF is tetrahydrofuran |
| DMSO is dimethylsulfoxide | TFA is trifluoroacetic acid |
| Pd$_2$(dba)$_3$ is Tris(dibenzylideneacetone) dipalladium (0); | Pd(PPh$_3$)$_4$ is tetrakis triphenylphosphine palladium (0) |
| Rochelle's salt is sodium potassium tartrate | |

The various organic group transformations and protecting groups utilized herein can be performed by a number of procedures other than those described below. References for other synthetic procedures that can be utilized for the preparation of intermediates or compounds disclosed herein can be found in, for example, M. B. Smith, J. March Advanced Organic Chemistry, 5$^{th}$ Edition, Wiley-Interscience (2001); R. C. Larock Comprehensive Organic Transformations, A Guide to Functional Group Preparations, 2$^{nd}$ Edition, VCH Publishers, Inc. (1999); T. L. Gilchrist Heterocyclic Chemistry, 3$^{rd}$ Edition, Addison Wesley Longman Ltd. (1997); J. A. Joule, K. Mills, G. F. Smith Heterocyclic Chemistry, 3$^{rd}$ Edition, Stanley Thornes Ltd. (1998); G. R. Newkome, W. W. Paudler Contemporary Heterocyclic Chemistry, John Wiley and Sons (1982); or Wuts, P. G. M.; Greene, T. W.; Protective Groups in Organic Synthesis, 3$^{rd}$ Edition, John Wiley and Sons, (1999), all six incorporated herein by reference in their entirety.

Example 1

Scheme 1

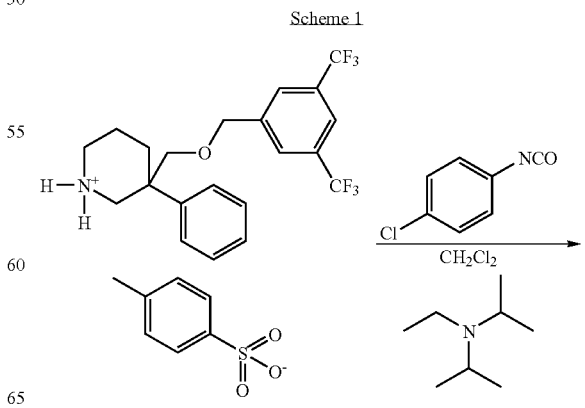

-continued

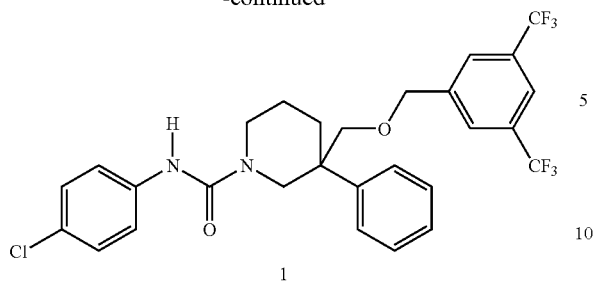

1

The mixture of amine sulfonate salt (20 mg), isocyanate (5 mg) and Hünig base (9 mg) in dichloromethane (1 mL) was stirred at rt for 12 h. The mixture was concentrated and purified by RP-HPLC to give the desired product 1.

1: $^1$H NMR (Acetone-d$_6$, 500 MHz): δ 8.03 (1H, s), 7.90 (1H, s), 7.79 (2H, s), 7.55 (2H, d), 7.49 (2H, m), 7.34 (2H, t), 7.22 (3H, m), 4.62 (2H, q), 4.07 (1H, d), 3.88 (1H, d), 3.80 (1H, d), 3.65 (2H, m), 3.42 (1H, m), 2.10 (2H, m), 1.71 (1H, m), 1.57 (1H, m); LCMS m/z: 571 (M$^+$+1).

The preparation of the second amine starting material for the synthesis of 1 follows literature procedures: Harrison, Timothy; Macleod, Angus Murray; Stevenson, Graeme Irvine; Williams, Brian John. Preparation of 4-(arylmethyloxymethyl)piperidines as tachykinin antagonists. PCT Int. Appl. (1994), WO 9410165 A1.

Example 2

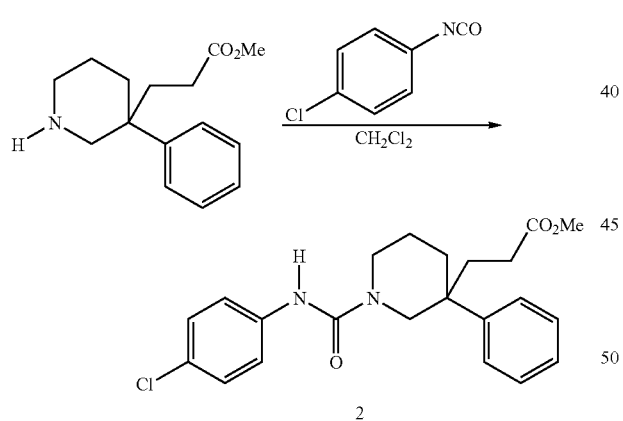

2

To a mixture of amine (30 mg) and isocyanate (7 mg) was added 2 mL of dichloromethane at rt. After 1 h, the mixture was purified by Biotage™ (5-45% ethyl acetate in hexanes) to give urea 2 as a colorless oil.

2: $^1$H NMR (Acetone-d$_6$, 500 MHz): δ 8.07 (1H, s), 7.54 (2H, d), 7.45 (2H, d), 7.35 (2H, t), 7.22 (3H, m), 3.96 (1H, d), 3.63 (1H, d), 3.58 (1H, m), 3.50 (4H, m), 1.90-2.14 (6H, m), 1.71 (1H, m), 1.54 (1H, m); LCMS m/z: 401 (M$^+$+1).

The starting secondary amine was prepared according the following reference:

Buchanan, George L. *Journal of the Chemical Society, Perkin Transactions 1: Organic and Bio-Organic Chemistry,* 1984, 11, 2669-70. Bredt's rule. Part 6. The synthesis of 5-phenyl-1-azabicyclo[3.3.1]nonan-2-one, a bridgehead amide.

Example 3

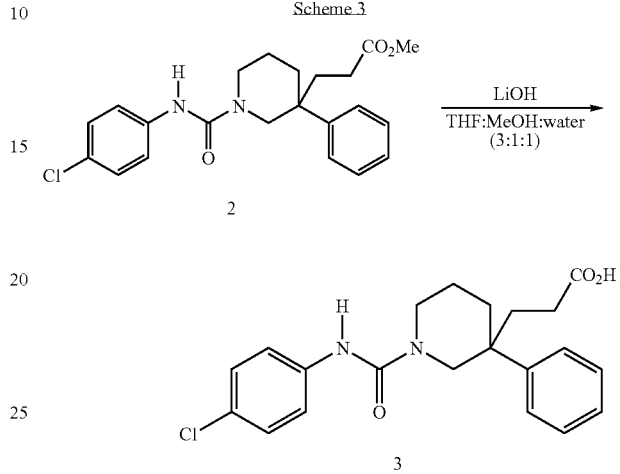

The mixture of urea 2 (11 mg) and LiOH (0.14 mL, 1 N in water) was stirred in 1 mL of THF:MeOH:water (3:1:1) at rt for 2 h, and then acidified with HCl. The mixture was then concentrated and purified by RP-HPLC to give 3 as a white solid.

3: $^1$H NMR (Acetone-d$_6$, 500 MHz): δ 8.11 (1H, s), 7.53 (2H, d), 7.46 (2H, d), 7.35 (2H, t), 7.23 (3H, m), 4.01 (1H, d), 3.64 (1H, d), 3.56 (2H, m), 2.16-1.87 (6H, m), 1.71 (1H, m), 1.52 (1H, m); LCMS m/z: 387 (M$^+$+1).

The same procedure as the synthesis of 1 was applied for the preparation of 4-7, 9-10, 14-27, and 39. The starting secondary amines or isocyanates are commercially available unless otherwise noted.

Example 4

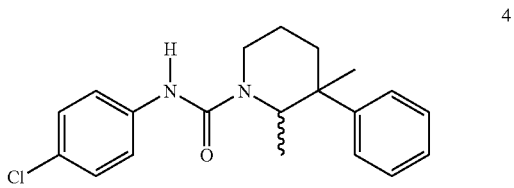

4

4: $^1$H NMR (Acetone-d$_6$, 500 MHz): δ 8.16 (1H, s), 7.60 (2H, m), 7.44 (2H, d), 7.38 (2H, t), 7.26 (3H, m), 4.71 (1H, q), 4.15 (1H, dd), 3.05 (1H, dt), 2.31 (1H, dt), 1.97 (1H, m), 1.81 (1H, d), 1.74 (1H, d), 1.40 (3H, s), 0.83 (3H, d); LCMS m/z: 343 (M$^+$+1).

The secondary amine starting material for the formation of 4 was obtained following the patent procedures: Schultz, E. M. 2-Methyl-3,3-disubstituted-piperidines. (1953), U.S. Pat. No. 2,636,881.

Example 5

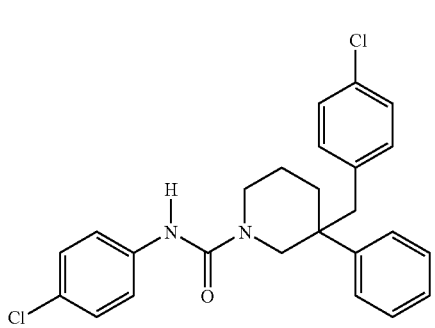

5: $^1$H NMR (Acetone-d$_6$, 500 MHz): δ 8.05 (1H, s), 7.53 (2H, d), 7.20-7.33 (7H, m), 7.09 (2H, d), 6.67 (2H, d), 4.23 (1H, d), 3.64 (1H, m), 3.50 (1H, d), 3.45 (1H, m), 3.00 (1H, d), 2.22 (1H, m), 2.08 (1H, m), 1.90 (1H, m), 1.78 (1H, m), 1.53 (1H, m); LCMS m/z: 440 (M$^+$+1).

The starting secondary amine for the synthesis of 5 could be prepared following the article below: Utjes-Le Gall, Monique; Salmon-Legagneur, Francois; Le Moal, Henri. Synthesis and study of ω-hydroxy acids, gem-disubstituted ω-amino alcohols, and their principal derivatives. *Journal of Chemical Research, Synopses*, 1978, 6, 198-9.

Example 6

Scheme 4

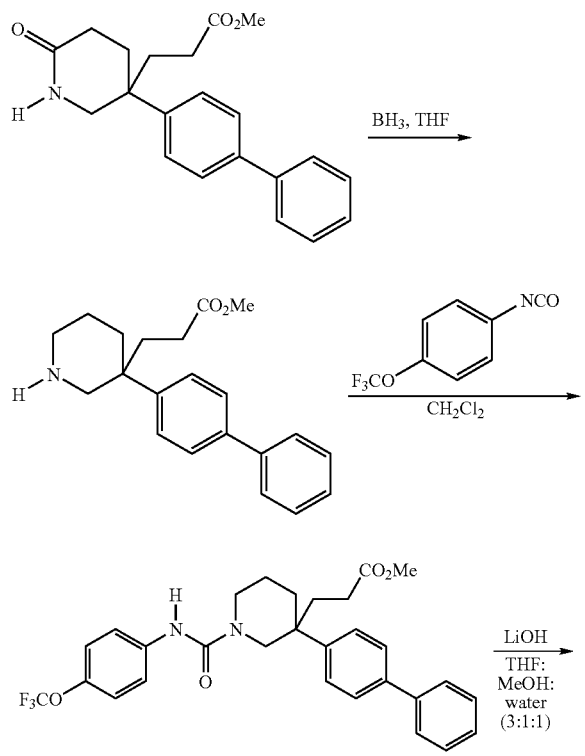

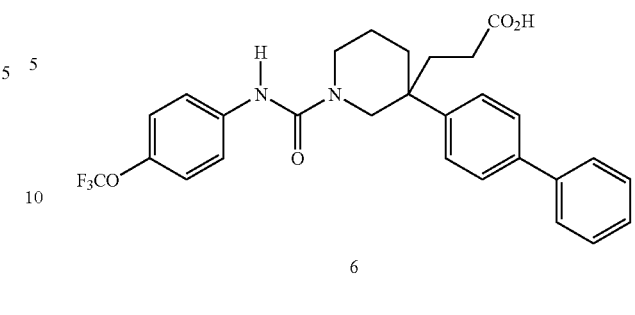

To the lactam (200 mg) in 3 mL of THF was added borane dimethyl sulfide complex in THF (0.89 mL, 2 M) at rt. The mixture was heated at 40 degrees for 2 h and carefully quenched with HCl (3 N) at 0° C. until pH=2. To the mixture was added water, and the mixture was extracted with ethyl acetate. The aqueous layer was basified with solid sodium hydroxide until pH=10. The mixture was then extracted with 30% isopropanol in chloroform. The organic layer was dried with sodium sulfate and concentrated in vacuo to give the desired secondary amine (~100 mg) as a neutral form and a colorless oil. The same procedures starting from the secondary amine as the preparation of 2 and 3 gave 6 as a white solid.

6: $^1$H NMR (CD$_3$OD, 500 MHz): δ 7.61 (4H, d), 7.51 (2H, d), 7.42 (4H, m), 7.33 (1H, t), 7.17 (2H, d), 4.12 (1H, d), 3.60 (2H, d), 3.51 (1H, m), 3.33 (1H, m), 2.27 (2H, m), 2.05 (3H, m), 1.78 (1H, m), 1.67 (1H, m); LCMS m/z: 513 (M$^+$+1).

The starting lactam was prepared in accordance with the following: Balkovec, J. et al. Preparation of 1,2,4-triazole derivatives as 11β-hydroxysteroid dehydrogenase 1 inhibitors useful for the treatment of diabetes, obesity and dyslipidemia. PCT Int. Appl. (2003), WO 2003065983 A2.

Example 7

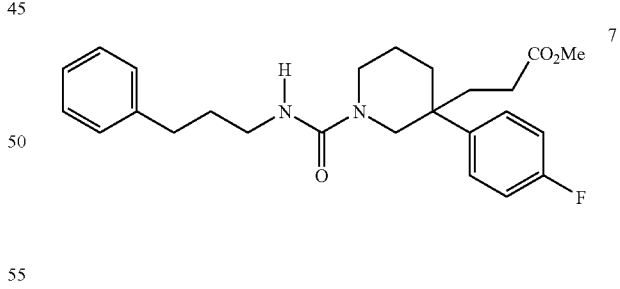

7: $^1$H NMR (Acetone-d$_6$, 500 MHz): δ 7.50 (2H, dd), 7.29 (2H, m), 7.24 (2H, m), 7.18 (1H, t), 7.10 (2H, t), 6.04 (1H, bs), 3.94 (1H, d), 3.51 (3H, s), 3.45 (1H, d), 3.78 (2H, m), 3.24 (2H, t), 2.67 (2H, t), 2.09 (2H, m), 1.80-2.04 (3H, m), 1.61 (1H, m), 1.43 (1H, m); LCMS m/z: 427 (M$^+$+1).

The starting secondary amine for the synthesis of 7 is prepared in accordance with: Burnett, D. et al. Preparation of piperidine-based MCH antagonists for treatment of obesity and CNS disorders. PCT Int. Appl. (2003), WO 2003045918 A1.

Example 8

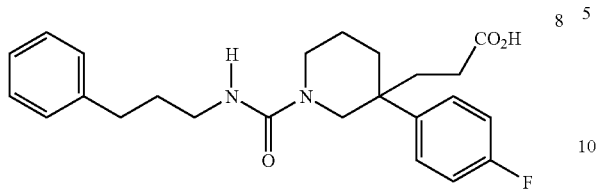

The hydrolysis of 7 gave 8 following the same procedure as the preparation of 3.

8: $^1$H NMR (Acetone-$d_6$, 500 MHz): δ 7.50 (2H, dd), 7.28 (2H, t), 7.25 (2H, d), 7.19 (1H, t), 7.10 (2H, t), 6.05 (1H, bs), 3.95 (1H, d), 3.47 (1H, d), 3.37 (2H, m), 3.34 (2H, m), 2.65 (2H, t), 1.80-2.11 (8H, m), 1.65 (1H, m), 1.45 (1H, m); LCMS m/z: 413 (M$^+$+1).

Example 9

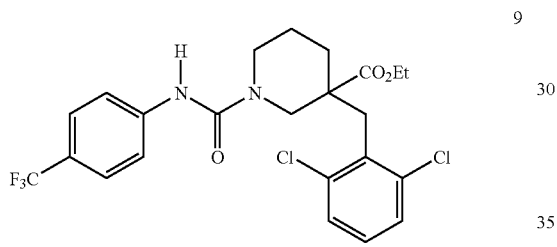

9: $^1$H NMR (Acetone-$d_6$, 500 MHz): δ 8.32 (1H, s), 7.65 (2H, dd), 7.57 (2H, d), 7.47 (2H, d), 7.33 (1H, t), 4.62 (1H, d), 4.21 (1H, d), 4.13 (2H, m), 3.32 (2H, q), 3.14 (1H, d), 2.80 (1H, m), 2.34 (1H, d), 1.81 (1H, m), 1.69 (1H, m), 1.55 (1H, m), 1.13 (3H, t); LCMS m/z: 503 (M$^+$+1).

Example 10

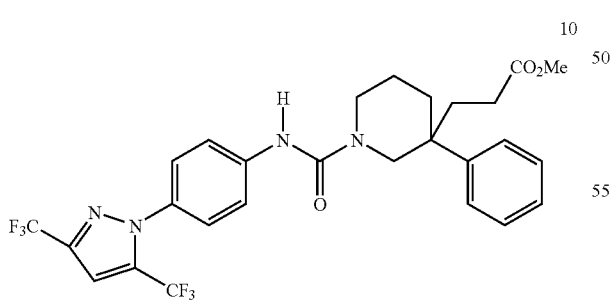

10: $^1$H NMR (Acetone-$d_6$, 500 MHz): δ 8.34 (1H, s), 7.76 (2H, d), 7.47 (5H, d), 7.36 (2H, t), 7.22 (1H, t), 4.04 (1H, d), 3.67 (1H, d), 3.62 (1H, m), 3.57 (1H, m), 3.51 (3H, s), 2.18 (1H, m), 1.90-2.14 (5H, m), 1.75 (1H, m), 1.57 (1H, m); LCMS m/z: 569 (M$^+$+1).

Example 11

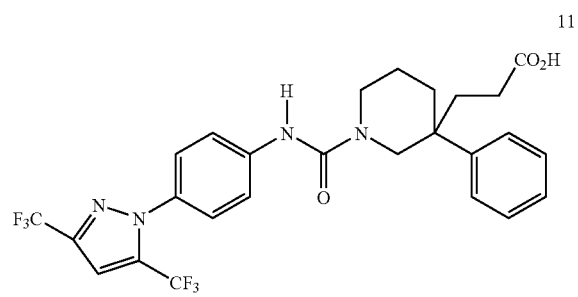

The same hydrolysis protocol as described for the preparation of 3 gave 11.

11: $^1$H NMR (Acetone-$d_6$, 500 MHz): δ 8.34 (1H, s), 7.76 (2H, d), 7.47 (4H, m), 7.36 (2H, t), 7.22 (1H, t), 4.06 (1H, d), 3.82 (1H, m), 3.62 (1H, d), 3.58 (2H, m), 2.18 (1H, m), 1.85-2.05 (3H, m), 1.75 (2H, m), 1.55 (1H, m); LCMS m/z: 555 (M$^+$+1).

Example 12

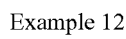

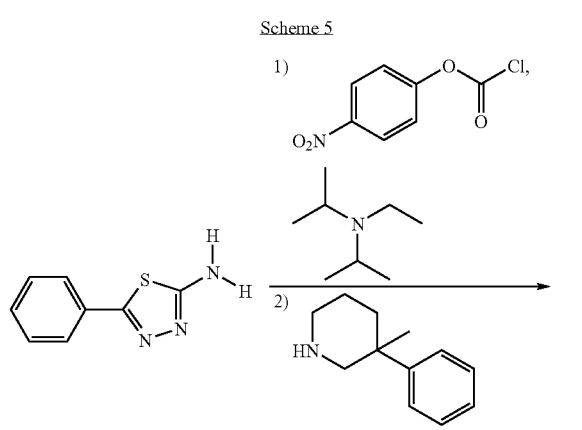

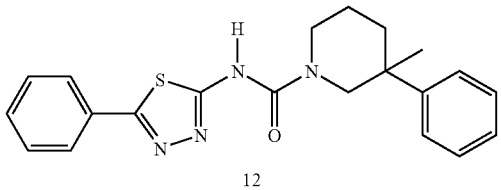

To a mixture of thiadiazole amine (50 mg), p-nitrophenyl chloroformate (57 mg) in THF (3 mL) and DCM (2 mL) was added ethyl diisopropyl amine (73 mg) at rt. After 30 min, to this mixture was added secondary amine (49 mg). The resulting mixture was stirred at rt overnight, concentrated and purified by RP-HPLC to give 12.

12: $^1$H NMR (Acetone-$d_6$, 500 MHz): δ 9.13 (1H, bs), 8.47 (1H, d), 8.37 (1H, d), 8.10 (1H, d), 7.53 (3H, m), 7.34 (2H, t), 7.21 (1H, t), 3.88 (3H, m), 3.53 (1H, bs), 2.20 (1H, m), 1.85 (2H, m), 1.64 (1H, m), 1.30 (3H, s); LCMS m/z: 379 (M$^+$+1).

Example 13

The same procedure as described in the preparation of 12 also gave 13.

13: $^1$H NMR (Acetone-d$_6$, 500 MHz): δ 8.95 (1H, s), 7.92 (1H, d), 7.61 (2H, t), 7.55 (2H, d), 7.34 (3H, m), 7.23 (1H, t), 4.06 (1H, d), 3.78 (1H, m), 3.70 (1H, d), 3.61 (1H, m), 2.25 (1H, m), 1.86 (2H, m), 1.67 (1H, m), 1.33 (3H, s); LCMS m/z: 336 (M$^+$+1).

Example 14

14: $^1$H NMR (Acetone-d$_6$, 500 MHz): δ 8.51 (1H, s), 7.69 (2H, d), 7.57 (2H, d), 7.30 (4H, m), 7.23 (1H, m), 3.98 (1H, m), 3.93 (1H, d), 3.71 (1H, d), 3.28 (1H, d), 3.10 (1H, m), 3.02 (1H, d), 2.87 (1H, d), 2.57 (1H, d), 2.08 (1H, m), 1.59 (2H, m), 1.38 (1H, m); LCMS m/z: 393 (M$^+$+1).

The starting secondary amine was prepared according to the following patents:

Morriello, G. et al. Di- and trisubstituted piperidine, pyrrolidine and hexahydro-1H-azepine peptide analogs promote release of growth hormone. U.S. (1998), Cont.-in-part of U.S. Pat. No. 5,492,916. U.S. Pat. No. 5,721,250 A. and Morriello, G. et al. Preparation of piperidines, pyrrolidines and hexahydro-1H-azepines which promote the release of growth hormone. PCT Int. Appl. (1995), WO 9513069 A1.

Example 15

15: $^1$H NMR (Acetone-d$_6$, 500 MHz): δ 7.73 (2H, d), 7.58 (2H, d), 7.32 (4H, m), 7.24 (4H, m), 7.14 (2H, m), 5.19 (1H, d), 4.92 (1H, d), 4.69 (1H, d), 4.27 (1H, d), 3.24 (1H, d), 3.12 (1H, d), 2.83 (1H, d), 2.08 (1H, m), 1.92 (1H, d), 1.78 (1H, m), 1.66 (1H, m), 1.55 (1H, m); LCMS m/z: 512 (M$^+$+1).

The secondary amine starting material is prepared following the procedures and references set forth with respect to compound 14.

Example 16

16: $^1$H NMR (Acetone-d$_6$, 500 MHz): δ 7.58 (3H, m), 7.17-7.32 (4H, m), 7.15 (2H, d), 4.40 (1H, d), 4.18 (1H, d), 2.93 (1H, d), 2.81 (1H, m), 2.70 (3H, d), 2.30 (1H, m), 2.09 (2H, m), 1.68 (2H, m), 1.47 (1H, m); LCMS m/z: 420 (M$^4$+1).

The secondary amine starting material is prepared following the patents referenced for the starting material leading to 14.

Example 17

17: $^1$H NMR (Acetone-d$_6$, 500 MHz): δ 8.47 (1H, s), 7.73 (2H, d), 7.58 (2H, d), 7.36 (5H, m), 4.50 (1H, d), 4.20 (1H, d), 3.07 (3H, d), 2.95 (1H, d), 1.99 (1H, m), 1.79 (3H, m); LCMS m/z: 388 (M$^+$+1).

The starting secondary amine was prepared following the patent below: Ishikawa, S. et al. Preparation of piperidine derivatives as histamine H3 receptor antagonists or inverse agonists. PCT Int. Appl. (2006), WO 2006129826 A1.

Example 18

Scheme 6

-continued

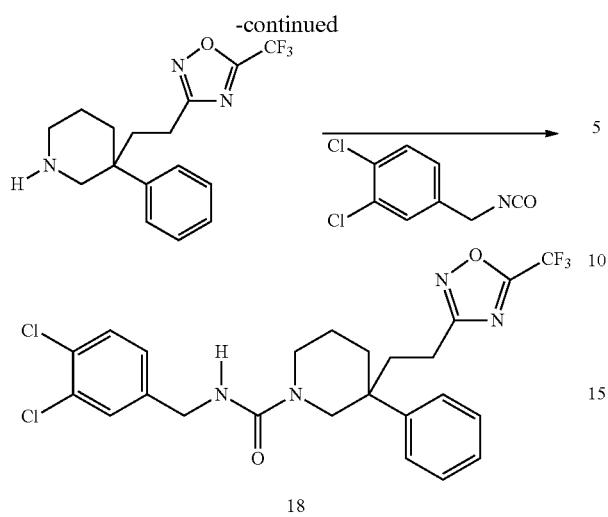

18

To trifluoromethyl hydroxyamidine (400 mg) was added molecular sieves (4A), THF and NaH (125 mg, 60% in mineral oil). The resulting mixture was stirred at 60 degrees for 1 h and to this mixture was added the secondary amine (386 mg). The mixture was then heated at reflux for 3 h. To this mixture was added 3 N HCl until pH=2. The mixture was diluted with water (20 mL), washed with ethyl acetate. The aqueous layer was basified with NaOH until pH=11. The resulting mixture was then extracted with 30% isopropanol in chloroform. The organic layer was dried with sodium sulfate, concentrated to give the secondary amine oxadiazole as a colorless oil containing a small amount of the secondary amine starting material. The secondary amine oxadiazole was then reacted with isocyanate to give product 18 following the procedure of the preparation of compound 2.

18: $^1$H NMR (Acetone-d$_6$, 500 MHz): δ 7.51 (4H, m), 7.37 (2H, m), 7.29 (2H, m), 6.65 (1H, s), 4.39 (2H, s), 3.95 (1H, d), 3.75 (1H, d), 3.56 (1H, m), 3.40 (1H, m), 2.90 (1H, m), 2.70 (1H, m), 2.28 (1, m), 2.16 (1H, m), 1.73 (1H, m), 1.54 (1H, m), 1.37 (1, m), 0.95 (1H, m); LCMS m/z: 528 (M$^+$+1).

Example 19

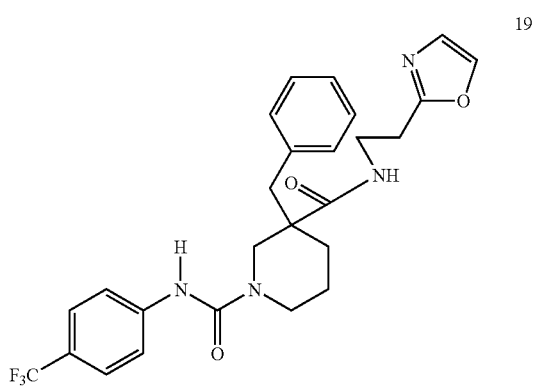

19: $^1$H NMR (Acetone-d$_6$, 500 MHz): δ 8.75 (1H, s), 8.00 (1H, s), 7.53 (4H, m), 7.25 (5H, m), 7.01 (1H, s), 4.57 (1H, dd), 4.49 (1H, dd), 4.40 (1H, d), 4.17 (1H, d), 2.97 (2H, dd), 2.88 (4H, m), 2.39 (1H, d), 1.64 (3H, m); LCMS m/z: 487 (M$^+$+1).

The secondary amine starting material is prepared following the patents referenced for the starting material leading to 14.

Example 20

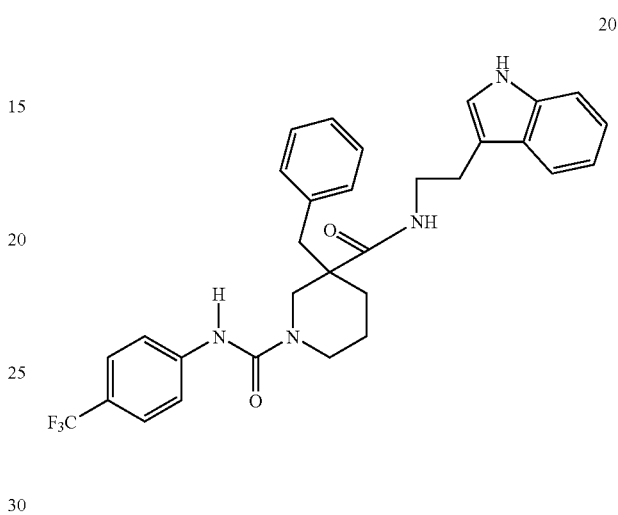

20: $^1$H NMR (Acetone-d$_6$, 500 MHz): δ 10.0 (1H, s), 9.10 (1H, s), 7.61 (4H, m), 7.39 (2H, m), 7.25 (3H, m), 7.17 (2H, m), 7.15 (1H, t), 7.03 (1H, t), 4.44 (1H, d), 4.18 (1H, d), 3.58 (1H, m), 3.52 (1H, m), 2.92 (6H, m), 2.27 (1H, d), 1.60 (2H, m), 1.43 (1H, m); LCMS m/z: 549 (M$^+$+1).

The secondary amine starting material is prepared following the patents referenced for the starting material leading to 14.

Example 21

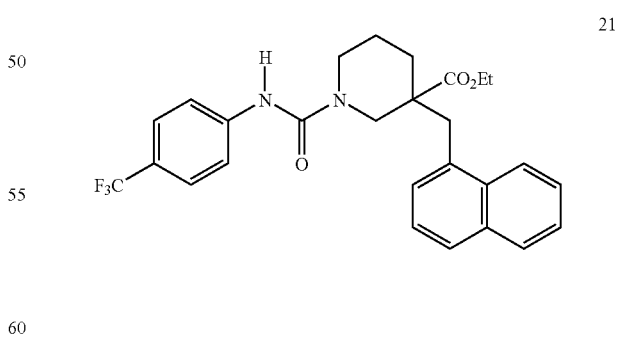

21: $^1$H NMR (Acetone-d$_6$, 500 MHz): δ 8.30 (1H, s), 8.14 (1H, d), 7.94 (1H, d), 7.85 (1H, dm), 7.63 (2H, d), 7.52 (5H, m), 7.41 (1H, d), 4.56 (1H, d), 4.15 (1H, d), 3.84 (1H, m), 3.91 (1H, m), 3.50 (1H, d), 3.37 (1H, d), 3.20 (1H, d), 2.86 (1H, t), 2.27 (1H, d), 1.75 (2H, m), 1.51 (1H, m), 0.92 (3H, t); LCMS m/z: 485 (M$^+$+1).

The secondary amine starting material is prepared following the patents referenced for the starting material leading to 14.

Example 22

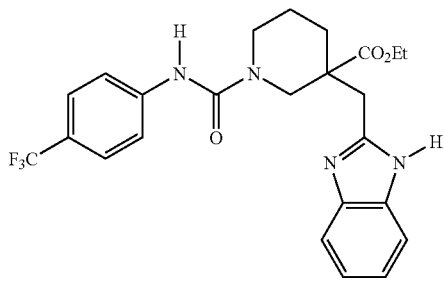

22: $^1$H NMR (Acetone-d$_6$, 500 MHz): δ 9.21 (1H, s), 7.77 (2H, bs), 7.65 (2H, d), 7.60 (2H, d), 7.43 (2H, bs), 4.08 (1H, d), 3.97 (2H, m), 3.57 (2H, m), 3.29 (2H, d), 3.22 (1H, d), 2.05 (1H, m), 1.73 (2H, m), 1.58 (1H, m), 0.90 (3H, t); LCMS m/z: 475 (M$^+$+1).

The secondary amine starting material is prepared following the patents referenced for the starting material leading to 14.

Example 23

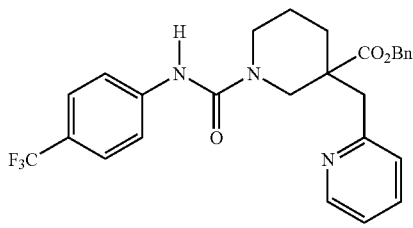

23: $^1$H NMR (DMSO-d$_6$, 500 MHz): δ 9.59 (1H, s), 8.70 (2H, d), 7.70 (4H, d), 7.60 (2H, m), 7.35 (3H, m), 7.21 (2H, d), 5.01 (2H, dd), 4.17 (1H, d), 3.97 (1H, m), 3.64 (1H, d), 3.40 (1H, d), 3.15 (1H, m), 3.02 (1H, d), 2.05 (2H, m), 1.78 (1H, m), 1.64 (1H, m); LCMS m/z: 498 (M$^+$+1).

The secondary amine starting material is prepared following the patents referenced for the starting material leading to 14.

Example 24

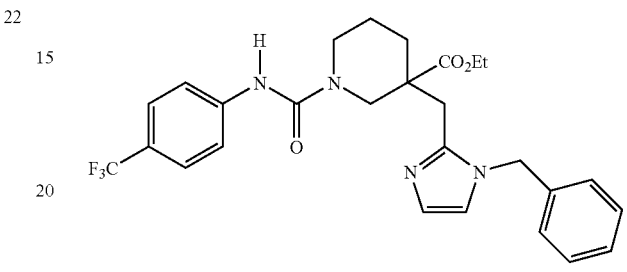

24: $^1$H NMR (Acetone-d$_6$, 500 MHz): δ 8.16 (1H, s), 7.82 (2H, d), 7.60 (2H, dd), 7.38 (3H, m), 7.22 (3H, m), 7.14 (1H, d), 5.50 (1H, d), 5.29 (1H, d), 4.64 (1H, d), 4.24 (1H, d), 3.39 (1H, d), 3.25 (1H, d), 3.07 (1H, d), 2.80 (1H, m), 2.57 (2H, s), 2.04 (4H, m), 1.95 (1H, m), 1.70 (2H, m); LCMS m/z: 515 (M$^+$+1).

The secondary amine starting material is prepared following the patents referenced for the starting material leading to 14.

Example 25

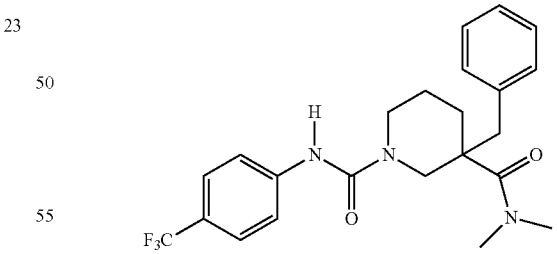

25: $^1$H NMR (Acetone-d$_6$, 500 MHz): δ 9.48 (1H, s), 7.56 (2H, d), 7.51 (2H, d), 7.33 (3H, m), 7.19 (2H, d), 4.37 (1H, d), 4.09 (1H, d), 3.06 (1H, m), 3.05 (6H, s), 2.91 (2H, d), 2.80 (1H, m), 2.59 (1H, m), 1.77 (2H, m), 1.44 (1H, m); LCMS m/z: 434 (M$^+$+1).

The secondary amine starting material is prepared following the patents referenced for the starting material leading to 14.

Example 26

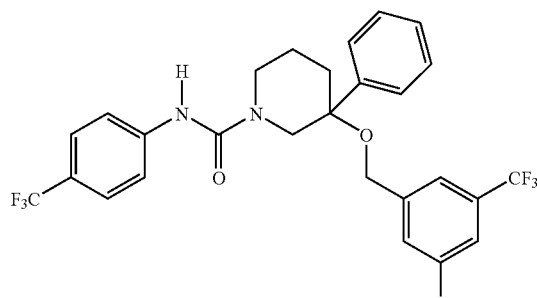

26: $^1$H NMR (Acetone-d$_6$, 500 MHz): δ 8.23 (1H, s), 7.88 (1H, s), 7.77 (2H, s), 7.65 (2H, d), 7.53 (2H, d), 7.48 (2H, d), 7.33 (2H, t), 7.22 (1H, t), 4.62 (2H, q), 4.08 (1H, d), 3.90 (1H, d), 3.78 (1H, d), 3.70 (2H, m), 3.43 (1H, m), 1.72 (1H, m), 1.58 (1H, m); LCMS m/z: 605 (M$^+$+1).

The starting secondary amine is prepared following the reference below. Martin, L. et al. Synthesis of spiro[isobenzofuran-1(3H), 4'-piperidines] as potential central nervous system agents. 5. Conformationally mobile analogs derived by furan ring opening. *Journal of Medicinal Chemistry* 1979, 22, 1347-54.

Example 27

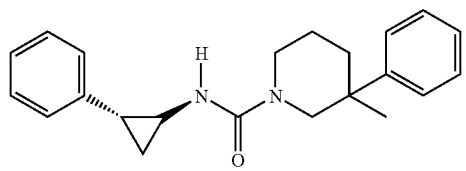

27: $^1$H NMR (Acetone-d$_6$, 500 MHz): δ 7.49 (2H, d), 7.34 (2H, t), 7.27 (2H, t), 7.22 (4H, m), 6.28 (1H, s), 3.80 (1H, dd), 3.56 (1H, m), 3.45 (1H, dd), 3.24 (1H, m), 2.82 (1H, m), 2.11 (2H, m), 1.98 (1H, m), 1.75 (1H, m), 1.64 (1H, m), 1.23 (3H, s), 1.10 (2H, m); LCMS m/z: 335 (M$^+$+1).

The secondary amine is prepared following the articles below:
Julia, M. et al. 3-Arylpiperidines. I. N-substituted 3-phenylpiperidines. *Bulletin de la Societe Chimique de France* 1968, 3, 987-99. Jones, R. et al. Conformational analysis of saturated heterocycles. XLII. 1,2-Dimethylhexahydropyridazine. *Journal of the Chemical Society, Perkin Transactions 2: Physical Organic Chemistry* (1972-1999) 1972, 1, 34-40.

The same procedure as described in the preparation of 12 also gave 28-38.

Example 28

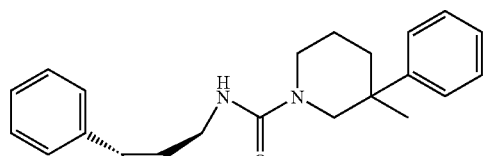

28: $^1$H NMR (Acetone-d$_6$, 500 MHz): δ 7.48 (2H, d), 7.31 (2H, q), 7.24 (2H, t), 7.20 (1H, t), 7.14 (1H, t), 7.10 (2H, d), 6.18 (1H, s), 3.81 (1H, t), 3.55 (1H, m), 3.42 (1H, t), 3.27 (2H, m), 2.10 (2H, m), 1.88 (1H, m), 1.72 (1H, m), 1.63 (1H, m), 1.40 (2H, m), 1.22 (3H, s), 0.93 (1H, m), 0.88 (1H, m); LCMS m/z: 349 (M$^+$+1).

Example 29

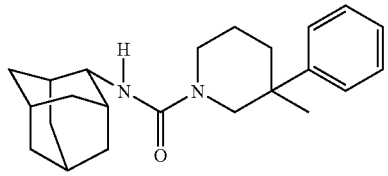

29: $^1$H NMR (Acetone-d$_6$, 500 MHz): δ 7.49 (2H, d), 7.32 (2H, t), 7.20 (2H, t), 5.55 (1H, s), 3.89 (2H, m), 3.52 (1H, m), 3.47 (1H, d), 3.40 (1H, m), 1.46-2.18 (18H, m), 1.25 (3H, s); LCMS m/z: 353 (M$^+$+1).

Example 30

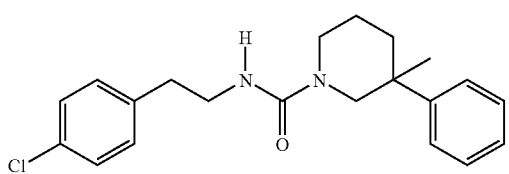

30: $^1$H NMR (Acetone-d$_6$, 500 MHz): δ 7.48 (2H, d), 7.34 (4H, m), 7.23 (3H, m), 6.04 (1H, s), 3.81 (1H, d), 3.52 (1H, m), 3.40 (3H, m), 3.22 (1H, m), 2.80 (2H, m), 2.11 (1H, m), 1.75 (1H, m), 1.62 (1H, m), 1.43 (1H, m), 1.22 (3H, s); LCMS m/z: 357 (M$^+$+1).

Example 31

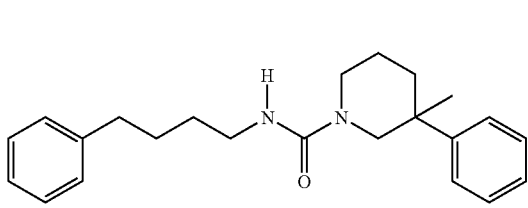

31: ¹H NMR (Acetone-d₆, 500 MHz): δ 7.48 (2H, d), 7.17-7.29 (7H, m), 5.94 (1H, s), 3.79 (1H, d), 3.51 (1H, m), 3.40 (1H, d), 3.23 (2H, m), 2.62 (2H, m), 2.08 (1H, m), 1.42-1.88 (8H, m), 1.23 (3H, s); LCMS m/z: 351 (M⁺+1).

Example 32

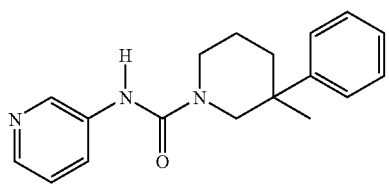

32: ¹H NMR (Acetone-d₆, 500 MHz): δ 9.37 (1H, s), 9.14 (1H, s), 8.62 (1H, d), 8.56 (1H, d), 8.00 (1H, m), 7.49 (2H, d), 7.34 (2H, t), 7.19 (1H, t), 3.93 (1H, d), 3.78 (1H, m), 3.68 (1H, d), 3.50 (1H, m), 2.19 (1H, m), 1.80 (2H, m), 1.60 (1H, m), 1.28 (3H, s); LCMS /z: 296 (M⁺+1).

Example 33

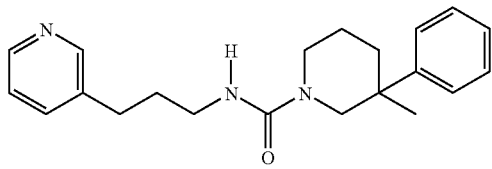

33: ¹H NMR (Acetone-d₆, 500 MHz): δ 8.47 (2H, d), 8.23 (1H, s), 7.70 (2H, d), 7.48 (1H, d), 7.35 (2H, d), 7.18 (1H, d), 6.24 (1H, s), 3.78 (1H, d), 3.68 (1H, m), 3.47 (1H, d), 3.15 (2H, m), 2.70 (2H, t), 2.08 (2H, m), 1.84 (2H, m), 1.78 (1H, m), 1.67 (1H, m), 1.47 (1H, m), 1.24 (3H, s); LCMS m/z: 338 (M⁺+1).

Example 34

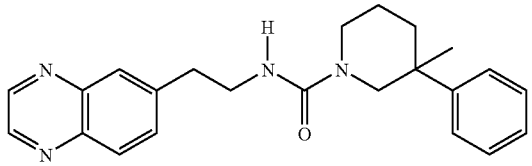

34: ¹H NMR (Acetone-d₆, 500 MHz): δ 8.87 (2H, dd), 8.00 (1H, d), 7.93 (1H, s), 7.73 (1H, dd), 7.46 (2H, d), 7.31 (2H, d), 7.19 (1H, t), 6.13 (1H, s), 3.76 (1H, d), 3.54 (2H, m), 3.42 (1H, d), 3.21 (1H, m), 3.11 (2H, t), 2.08 (2H, m), 1.74 (1H, m), 1.66 (1H, m), 1.43 (1H, m), 1.19 (3H, s); LCMS m/z: 375 (M⁺+1).

Example 35

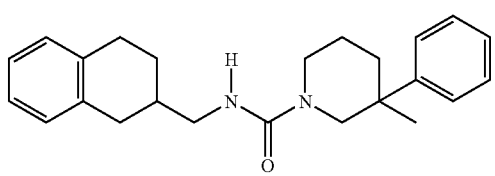

35: ¹H NMR (Acetone-d₆, 500 MHz): δ 7.50 (2H, d), 7.33 (2H, m), 7.20 (1H, m), 7.06 (4H, m), 6.14 (1H, s), 3.73 (1H, dd), 3.55 (1H, m), 3.44 (1H, dd), 3.35 (1H, m), 3.23 (2H, t), 2.85 (2H, m), 2.67 (2H, m), 2.44 (1H, m), 2.10 (1H, m), 1.99 (2H, m), 1.75 (1H, m), 1.64 (1H, m), 1.42 (2H, m), 1.25 (3H, s); LCMS m/z: 385 (M⁺+23).

Example 36

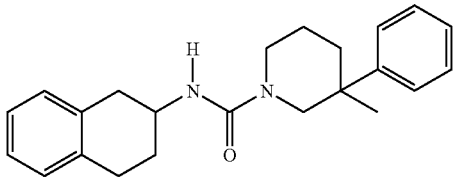

36: ¹H NMR (Acetone-d₆, 500 MHz): δ 7.49 (2H, d), 7.33 (2H, m), 7.20 (1H, t), 7.19 (3H, m), 7.05 (1H, m), 5.83 (1H, d), 4.07 (1H, m), 3.82 (1H, m), 3.55 (1H, m), 3.43 (1H, t), 3.30 (1H, m), 3.07 (1H, d), 2.90 (2H, m), 2.75 (1H, m), 2.08 (2H, m), 1.75 (2H, m), 1.42 (1H, m), 1.24 (3H, s); LCMS m/z: 349 (M⁺+1).

Example 37

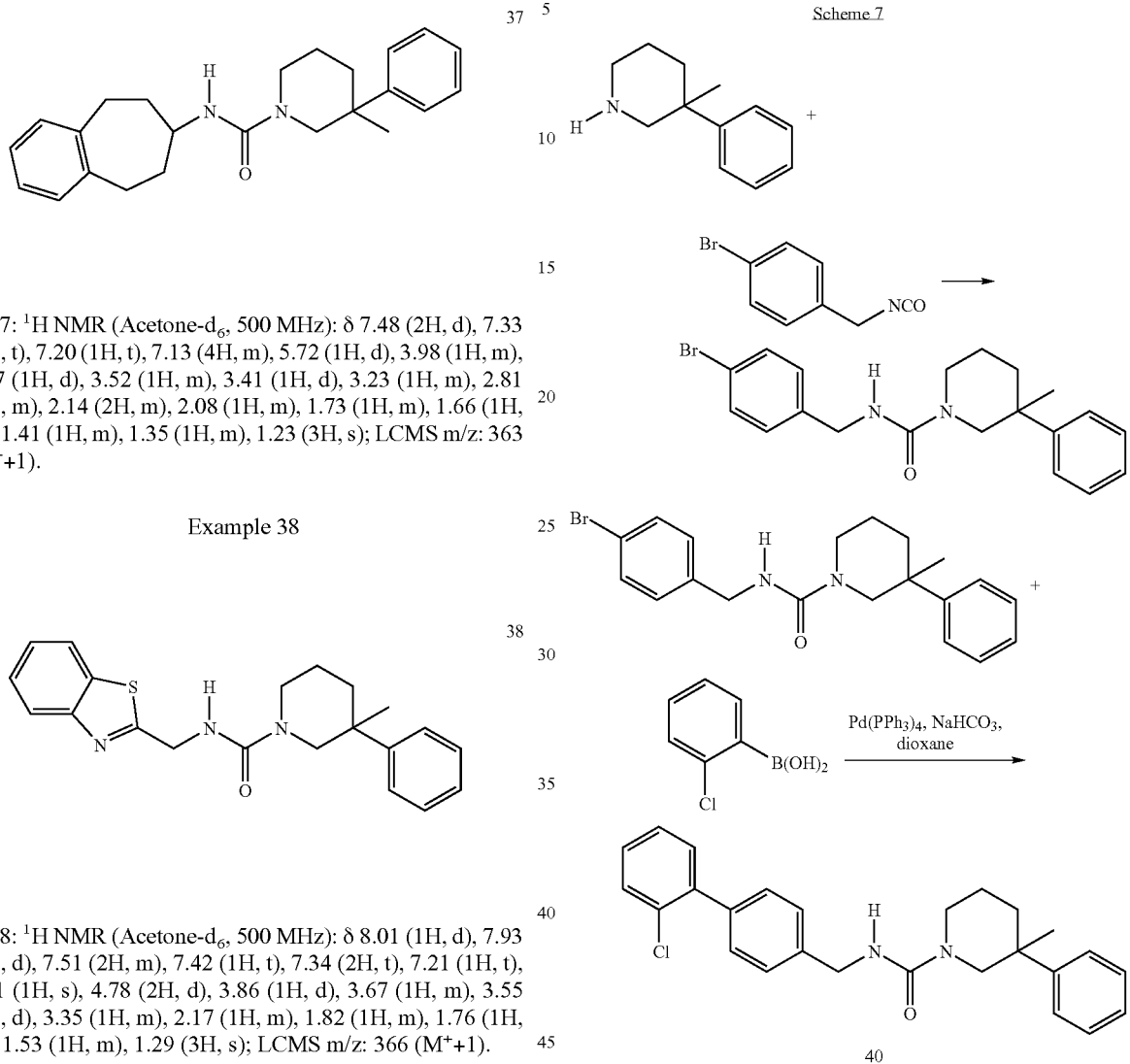

37: $^1$H NMR (Acetone-d$_6$, 500 MHz): δ 7.48 (2H, d), 7.33 (2H, t), 7.20 (1H, t), 7.13 (4H, m), 5.72 (1H, d), 3.98 (1H, m), 3.77 (1H, d), 3.52 (1H, m), 3.41 (1H, d), 3.23 (1H, m), 2.81 (4H, m), 2.14 (2H, m), 2.08 (1H, m), 1.73 (1H, m), 1.66 (1H, m), 1.41 (1H, m), 1.35 (1H, m), 1.23 (3H, s); LCMS m/z: 363 (M$^+$+1).

Example 38

38: $^1$H NMR (Acetone-d$_6$, 500 MHz): δ 8.01 (1H, d), 7.93 (1H, d), 7.51 (2H, m), 7.42 (1H, t), 7.34 (2H, t), 7.21 (1H, t), 6.91 (1H, s), 4.78 (2H, d), 3.86 (1H, d), 3.67 (1H, m), 3.55 (1H, d), 3.35 (1H, m), 2.17 (1H, m), 1.82 (1H, m), 1.76 (1H, m), 1.53 (1H, m), 1.29 (3H, s); LCMS m/z: 366 (M$^+$+1).

Example 39

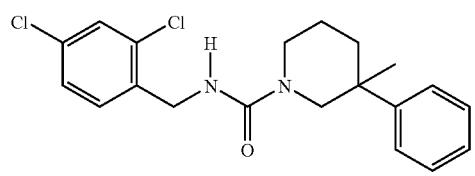 [SMILES: CC1(c2ccccc2)CCCN(C(=O)NCc2ccc(Cl)cc2Cl)C1]

39: $^1$H NMR (Acetone-d$_6$, 500 MHz): δ 7.47 (2H, d), 7.45 (1H, d), 7.34 (4H, m), 7.20 (1H, t), 4.42 (2H, s), 3.87 (1H, d), 3.53 (1H, m), 3.43 (1H, d), 3.36 (1H, m), 2.12 (1H, m), 1.75 (1H, m), 1.65 (1H, m), 1.50 (1H, m), 1.23 (3H, s); LCMS m/z: 378 (M$^+$+1).

Example 40

To the mixture of amine (330 mg) and 20 mL of dichloromethane was added isocyanate (399 mg). The mixture was stirred at rt overnight. This mixture was then concentrated and purified by Biotage™ (5-40% ethyl acetate in hexanes) to give the urea bromide intermediate (450 mg) as a colorless oil.

The mixture of urea bromide (20 mg), boronic acid (8 mg), Pd(PPh$_3$)$_2$Cl$_2$ (4 mg) and sodium bicarbonate solution (0.15 mL, 1 M in water) in dioxane (1.5 mL) was heated at 150° C. for 20 min. To this mixture was added a few drops of 3 N HCl and the resulting mixture was concentrated in vacuo. The residue was dissolved in DMSO, filtered and then purified by RP-HPLC to give the desired product 40.

40: $^1$H NMR (Acetone-d$_6$, 500 MHz): δ 7.52 (4H, m), 7.40 (5H, m), 7.32 (2H, m), 7.20 (1H, m), 6.47 (1H, m), 4.43 (2H, m), 3.92 (1H, d), 3.57 (1H, m), 3.42 (1H, d), 3.39 (1H, m), 2.15 (1H, m), 1.77 (1H, m), 1.65 (1H, m), 1.43 (1H, m) 1.25 (3H, s); LCMS m/z: 419 (M$^+$+1).

The same procedure as described for the preparation of 40 also gave 41-44.

Example 41

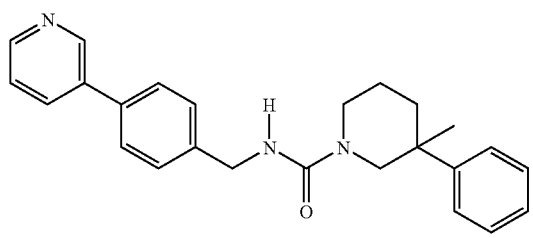 [SMILES: CC1(c2ccccc2)CCCN(C(=O)NCc2ccc(-c3cccnc3)cc2)C1]

41

41: $^1$H NMR (Acetone-d$_6$, 500 MHz): δ 8.88 (1H, d), 8.58 (1H, dd), 8.03 (1H, m), 7.65 (2H, d), 7.51 (2H, d), 7.46 (2H, d), 7.34 (2H, t), 7.20 (1H, t), 6.48 (1H, s), 4.48 (2H, m), 3.91 (1H, d), 3.58 (1H, m), 3.42 (1H, d), 3.39 (1H, m), 2.15 (1H, m), 1.778 (1H, m), 1.68 (1H, m), 1.48 (1H, m) 1.26 (3H, s); LCMS m/z: 386 (M$^+$+1).

Example 42

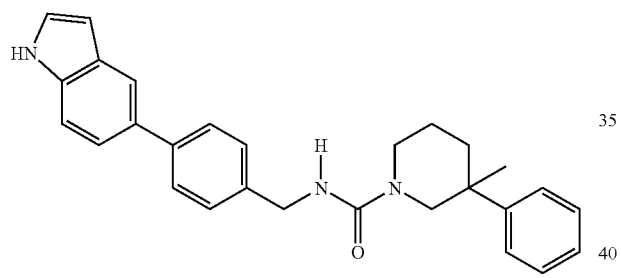

42

42: $^1$H NMR (Acetone-d$_6$, 500 MHz): δ 7.84 (1H, s), 7.60 (2H, m), 7.20-7.58 (12H, m), 6.54 (1H, m), 4.43 (1H, m), 4.36 (1H, m), 3.88 (1H, d), 3.30-3.58 (3H, m), 3.02 (1H, m), 1.70 (1H, m), 1.65 (1H, m), 1.43 (1H, m), 1.25 (3H, s); LCMS m/z: 424 (M$^+$+1).

Example 43

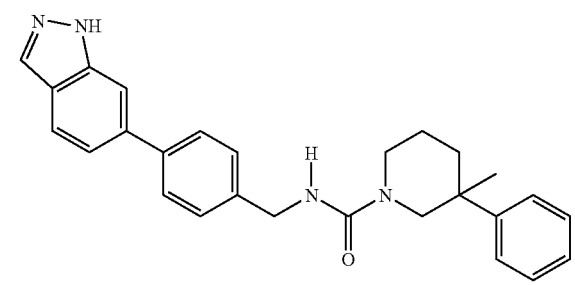 [SMILES: CC1(c2ccccc2)CCCN(C(=O)NCc2ccc(-c3ccc4cn[nH]c4c3)cc2)C1]

43

43: $^1$H NMR (Acetone-d$_6$, 500 MHz): δ 8.07 (1H, s), 7.82 (2H, m), 7.80 (1H, s), 7.20-7.70 (10H, m), 6.45 (1H, m), 4.42 (2H, s), 3.88 (1H, d), 3.58 (1H, m), 3.44 (1H, m), 3.27 (1H, m), 2.05 (1H, s), 1.78 (1H, m), 1.63 (1H, m), 1.45 (1H, m), 1.25 (3H, s); LCMS m/z: 425 (M$^+$+1).

Example 44

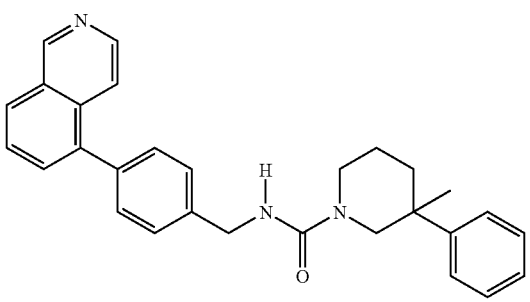 [SMILES: CC1(c2ccccc2)CCCN(C(=O)NCc2ccc(-c3cccc4cnccc34)cc2)C1]

44

44: $^1$H NMR (Acetone-d$_6$, 500 MHz): δ 9.38 (1H, s), 8.51 (1H, d), 8.17 (1H, d), 7.78 (3H, m), 7.50 (7H, m), 7.34 (2H, t), 7.20 (1H, t), 4.56 (2H, m), 3.95 (1H, d), 3.58 (1H, m), 3.45 (1H, d), 3.42 (1H, m), 2.15 (1H, m), 1.78 (1H, m), 1.67 (1H, m), 1.45 (1H, m), 1.27 (3H, s); LCMS m/z: 436 (M$^+$+1).

Example 45

Scheme 8

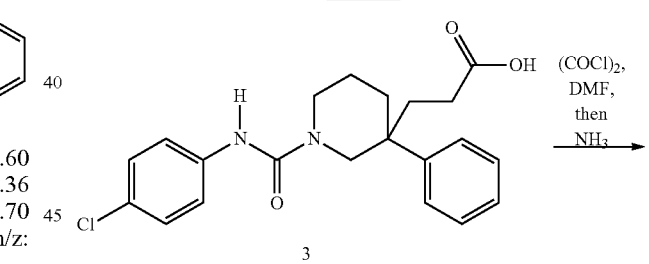

3

(COCl)$_2$, DMF, then NH$_3$ →

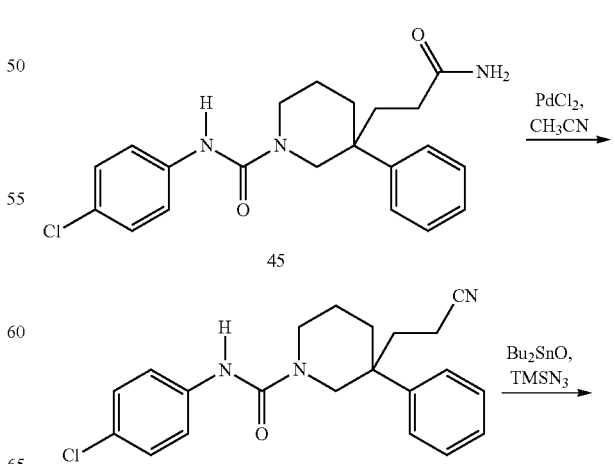

45

PdCl$_2$, CH$_3$CN →

46

Bu$_2$SnO, TMSN$_3$ →

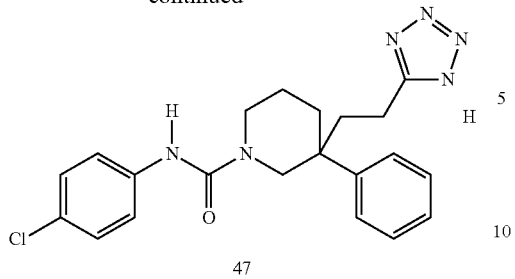

47

To 3 in 3 mL of DCM was added 1 drop of DMF and oxalyl chloride (0.26 mL, 2 M in DCM). The resulting mixture was stirred at rt for 20 min. To this mixture was bubbled ammonia gas for 2 min. The resulting slurry was purified by RP-HPLC and the resulting solid was washed with acetone. The filtrate was concentrated to give 45 as a light yellow oil.

45: $^1$H NMR (Acetone-$d_6$, 500 MHz): δ 10.84 (1H, s), 10.63 (1H, s), 7.77 (2H, d), 7.40 (2H, d), 7.44 (1H, t), 7.34 (2H, m), 7.21 (1H, m), 7.09 (1H, m), 6.61 (1H, s), 3.89 (2H, m), 3.56 (2H, m), 2.00 (2H, m), 1.80 (2H, m), 1.64 (2H, m), 1.42 (2H, m); LCMS m/z: 386 (M$^+$+1).

Example 46

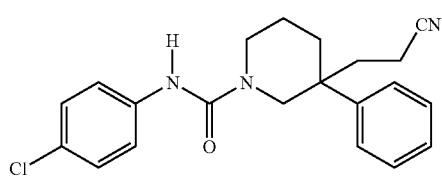

46

To 45 (10 mg) was added PdCl$_2$ (10 mg) and 3 mL of acetonitrile. The mixture was stirred at rt overnight and purified by RP-HPLC to give 46 as a colorless oil.

46: $^1$H NMR (Acetone-$d_6$, 500 MHz): δ 8.10 (1H, s), 7.56 (2H, d), 7.49 (2H, d), 7.41 (2H, t), 7.28 (3H, m), 3.94 (1H, d), 3.67 (1H, m), 3.46 (1H, m), 1.92-2.21 (5H, m), 1.78 (2H, m), 1.56 (2H, m); LCMS m/z: 368 (M$^+$+1).

Example 47

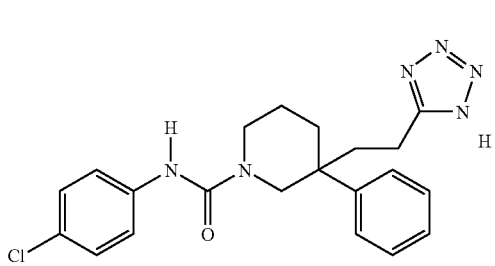

47

To 46 (48 mg) and TMSN$_3$ (45 mg) in 3 mL of toluene was added dibutyltin oxide (16 mg). The mixture was heated at 105 degrees for 24 h. After removing the solvent, the residue was purified by RP-HPLC to give 47.

47: $^1$H NMR (Acetone-$d_6$, 500 MHz): δ 8.17 (1H, s), 7.52 (4H, d), 7.39 (2H, t), 7.25 (3H, m), 4.01 (1H, d), 3.83 (1H, d), 3.68 (1H, m), 3.50 (1H, m), 2.72 (1H, m), 2.58 (1H, m), 2.20 (2H, m), 2.08 (2H, m), 1.79 (1H, m), 1.58 (1H, m); LCMS m/z: 411 (M$^+$+1).

Example 48

Scheme 9

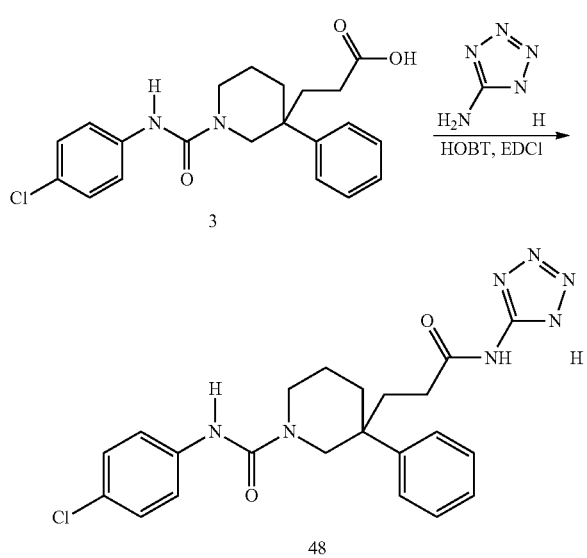

To acid 3 (26 mg) and aminotetrazole (29 mg) in 3 mL of DMF was added EDCI (10 mg) and HOBT (5 mg). The mixture was stirred at rt overnight and purified by RP-HPLC to give 48 as a white solid.

48: $^1$H NMR (Acetone-$d_6$, 500 MHz): δ 11.02 (1H, s), 8.15 (1H, s), 7.57 (2H, dd), 7.48 (2H, d), 7.36 (2H, t), 7.26 (2H, d), 7.22 (1H, t), 3.97 (1H, d), 3.79 (1H, dt), 3.65 (1H, m), 3.49 (1H, m), 2.39 (1H, m), 2.20 (1H, m), 2.14 (3H, m), 2.02 (1H, m), 1.80 (1H, m), 1.57 (1H, m); LCMS m/z: 454 (M$^+$+1).

The similar procedure as the preparation of 48 except that dichloromethane was used as the solvent gave 49 and 50.

Example 49

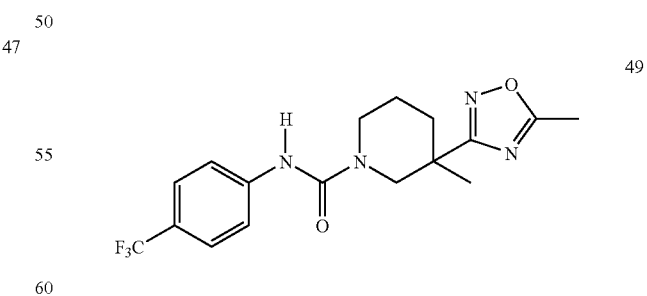

49

The similar procedures as described for the preparation of example 18 gave example 49.

49: $^1$H NMR (Acetone-$d_6$, 500 MHz): δ 8.62 (1H, s), 7.69 (2H, d), 4.34 (1H, d), 3.92 (1H, m), 3.43 (1H, d), 3.20 (1H, m), 2.39 (1H, m), 2.35 (3H, s), 1.82 (1H, m), 1.77 (1H, m), 1.57 (1H, m), 1.40 (3H, s); LCMS m/z: 369 (M$^+$+1).

Example 50

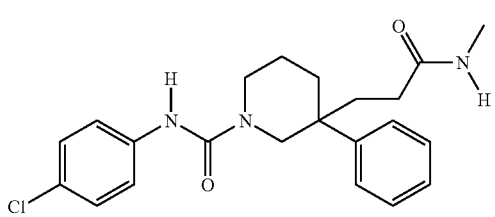

50: $^1$H NMR (Acetone-$d_6$, 500 MHz): δ 8.26 (1H, s), 7.57 (2H, d), 7.45 (2H, d), 7.37 (2H, t), 7.25 (3H, m), 6.96 (1H, bs), 3.93 (1H, d), 3.66 (2H, m), 3.42 (1H, m), 2.60 (3H, d), 1.85-2.10 (5H, m), 1.72 (2H, m), 1.51 (1H, m); LCMS m/z: 400 (M$^+$+1).

Example 51

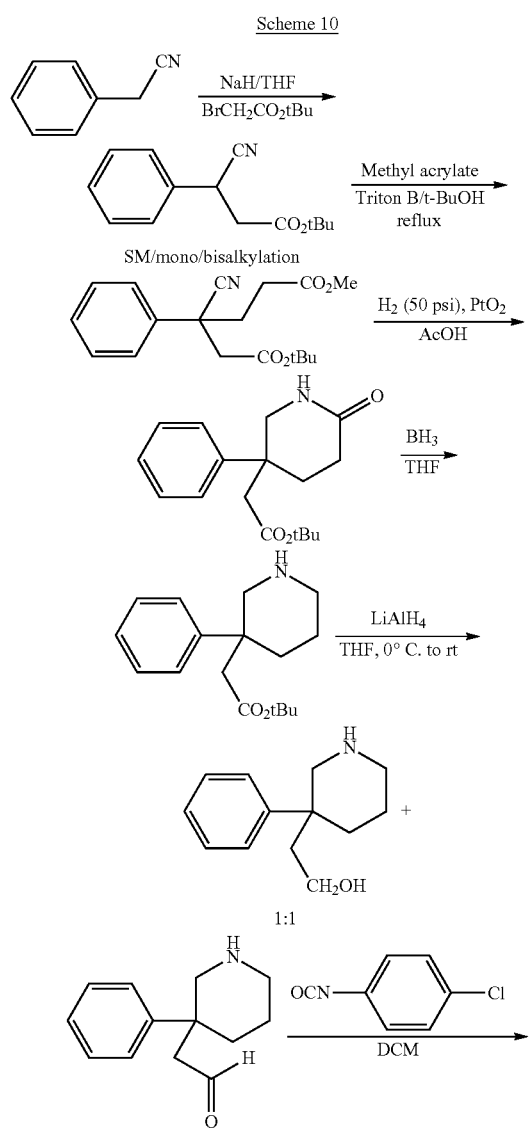

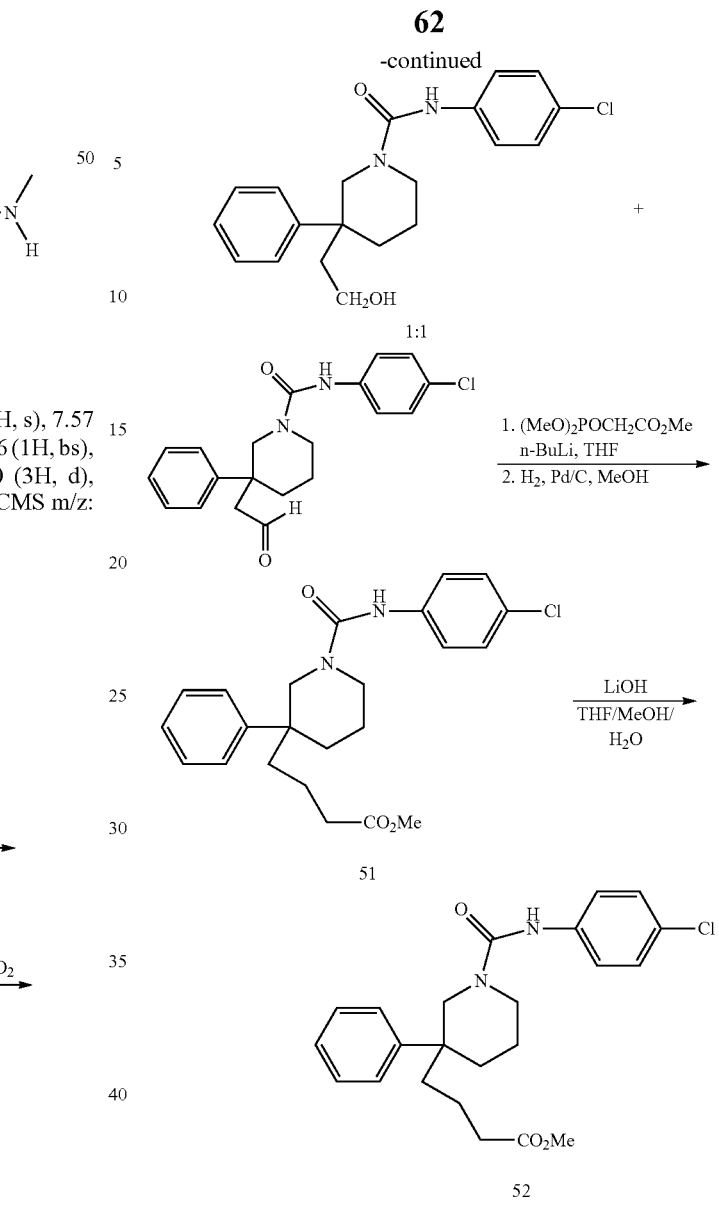

To the solution of benzylnitrile (5 g, 42.7 mmol) in 100 mL THF was added NaH (1.88 g, 47 mmol, 60%) at 0° C. After 30 min, to this mixture was added tert-butyl bromoacetate (5.83 g, 29.9 mmol) at 0° C. The resulting mixture was warmed to rt and stirred overnight. The solution was then diluted in EtOAc, washed with water, dried over sodium sulfate, and purified on silica gel eluting with 0-5% EtOAc/hexane to get a mixture of three compounds (5.48 g) (starting material/ monoalkylation/bisalkylation products).

To the solution of the mixture (5.48 g) and methyl acrylate (13 mL) in tert-butanol (14 mL) at boiling point was added a solution of 40% methanolic Triton B (3.4 mL) in 6 mL tert-butanol carefully. The resulting mixture was under reflux for 5 h. After distillating off the solvent, the residue was dissolved in chloroform, washed with 1N HCl twice, water, dried over sodium sulfate, and concentrated to get 10.4 g of the crude mixture.

This crude intermediate was then submitted to hydrogenation at 50 psi in acetic acid for 3 h. After filtration under N$_2$, the filtrate was concentrated and the residue was dissolved in EtOAc, washed with sat. NaHCO$_3$, dried over sodium sulfate, the concentrated in vacuo. The residue was purified on silica gel using 40-100%-100% ethyl acetate in hexanes to get 0.87 g of the lactam intermediate as a white solid.

To the solution of the lactam (0.87 g, 3.0 mmol) in THF (40 mL) at 0° C. was added borane-THF complex (3.6 mL, 3.6 mmol), and the resulting solution was stirred at rt for 2 h. About 50% conversion was observed by LC/MS. To the above solution was added additional 3.6 mL of borane THF complex. The solution was stirred at rt for additional 2.5 h. The reaction was quenched by addition of acetic acid at 0° C. After removing the organic solvent, the residue was dissolved in EtOAc (200 mL), washed with sat. NaHCO$_3$, dried over sodium sulfate, and concentrated to afford 0.857 g of amine ester as a crude oil.

To the solution of the amino ester (0.73 g, 2.65 mmol) in THF (40 mL) at 0° C. was added lithium aluminium hydride (13.30 mL, 1N in Et2O) and the resulting solution was stirred at rt for 5 h. The mixture was then quenched by water dropwise at 0° C. Then the mixture was diluted with EtOAc and Rochelle's salt until it became clear. The aqueous phase was extracted with EtOAc three times, the combined organic phase was washed with sat. NaHCO$_3$, dried over sodium sulfate to afford 163 mg of oily solid. The aqueous phase was extracted with 30% isopropanol/chloroform three times. The combined organic phase was washed with sat. NaHCO$_3$, dried over sodium sulfate. After concentration, the residue was dissolved in EtOAc, dried over sodium sulfate, to give 195 mg of oily solid. A total of 358 mg mixture of the alcohol and aldehyde was obtained.

The mixture was then reacted with isocyanate in the manner similar to the preparation of 2. The resulting aldehyde urea (200 mg) could be isolated by Biotage™ (20% ethyl acetate in hexanes).

To the solution of trimethyl phosphonoacetate (344 mg, 1.89 mmol) in 20 mL of THF at 0° C. was added n-BuLi (0.75 mL, 2.5M, 1.89 mmol). The solution was stirred at 0° C. for 10 min. Then to this solution was added a solution of the aldehyde urea (225 mg, 0.63 mmol) in 10 mL of THF was added. The solution was warmed to rt and stirred at it for 10 min. The mixture was then quenched by water and HCl, diluted with EtOAc, washed with water, dried over sodium sulfate. After concentration, the residue (311 mg) was directly used in next step.

The crude intermediate was placed under a hydrogen balloon, in the presence of Pd/C (62 mg, 10%) in 30 mL methanol. After 1 h, the mixture was filtered and the residue was purified on silica gel eluting with 20-40% EtOAc/hexanes to give 51.

51 was further hydrolyzed to 52 following the procedure described for the preparation of 3.

51: $^1$H NMR (Acetone-D$_6$, 500 MHz): δ 8.03 (1H, s), 7.55 (2H, d), 7.53 (2H, d), 7.32 (2H, t), 7.24 (3H, m), 4.05 (2H, m), 3.52 (4H, m), 2.18 (2H, m), 2.05 (1H, m), 1.87 (1H, m), 1.70 (3H, m), 1.55 (1H, m), 1.32 (2H, m), 1.23 (1H, m); LCMS m/z: 415 (M$^+$+1).

Example 52

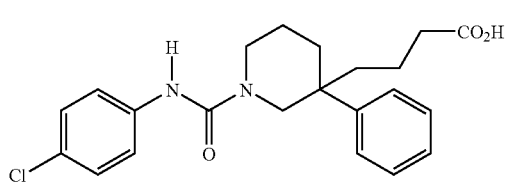

52

52: $^1$H NMR (CD$_3$OD, 500 MHz): δ 8.05 (1H, s), 7.54 (2H, m), 7.48 (2H, d), 7.35 (2H, t), 7.26 (3H, m), 4.11 (2H, d), 3.54 (4H, m), 2.15 (2H, m), 1.94 (1H, m), 1.78 (1H, m), 1.70 (1H, m), 1.53 (1H, m), 1.30 (2H, m); LCMS m/z: 401 (M$^+$+1).

sEH Human Enzyme Assay

Preparation of Recombinant sEH Human Enzyme

The DNA for expressing sEH was designed based on a rhesus monkey sEH cDNA. Necessary Modifications were introduced to optimize for its expression both in E. coli and insect cells. The designed DNA fragment encodes a protein sequence that is identical to full length human sEH, and the DNA was synthesized in vitro. The DNA was then subcloned into the pET100 vector that will generate a fusion protein with an N-terminal His-tag. The recombinant protein was expressed in E. coli. The sEH enzyme was affinity purified by a Ni$^{++}$ column. His-tag was removed by Enter Kinase (EK) digestion. The purified enzyme aliquots were frozen and held at −80° C. for later use.

Fluorescence Based Enzyme In Vitro Assay

For each assay (100 ul), an aliquot of enzymes (about 1 nM final concentration) was incubated with a fluorescence substrate, S7 (10 uM final concentration), in sEH assay buffer (25 mM HEPES, pH7.0, 0.1 mg/ml BSA) in a 96-well plate. The kinetic reaction reading (Ex330/Em465) was conducted using a plate reader, Spectra max (Molecular Devices) at 25° C.

DHET Production Assay

HEK293 (human kidney) cells were seeded at 4.2×10$^4$ cells/well (100 ul) in 96-well plate in DMEM medium (high glucose) containing 10% FBS, 100 units/ml Penicillin and 100 ug/ml Streptomycin at 37° C. in a humidified atmosphere of 10% CO$_2$. After 24 h, the medium was changed to the same medium but without FBS for 1 h. The compound, diluted in DMSO, was added to each well for 1 h. Then, the substrate EET (3 uM final conc.) was added to each well for 2 h. At the end of the incubation period, 80 ul of medium was transferred to a new 96 well plate followed by LC-MS/MS analysis for the production of DHET.

Effects of Soluble Epoxide Hydrolase Inhibitors on Blood Pressure in Adult Spontaneously Hypertensive Rats (SHR)

Adult male SHRs (4-8 months of age, 400-450 g body weight) were used for all telemetry blood pressure studies; rats were maintained on a normal Na diet (0.4% NaCl, Purina 5001) and offered food and water ad lib. Starting at 4 months of age, the rats were anesthetized with ketamine-xylazine-acepromazine mix (IM), and under sterile conditions, were implanted with a catheter from a telemetry device (TA11PA-C40, pressure & activity, Data Sciences International) into the lower abdominal aorta via the left femoral artery. The body of the transmitter was placed subcutaneously into a pocket between the left caudal edge of the ribcage and the most cranial extension of the knee's range of motion and secured by passing 3.0 silk sutures through the tissue surrounding the pocket entrance. To keep the catheter in proper orientation, the catheter stem was sutured to surrounding muscle tissue and looped subcutaneously to prevent kinking. The rats were allowed to recover from surgery until sternal recumbency on a warmed water blanket, and then housed single in shoebox cages. Rats were allowed to recover from surgery and to acclimate to single housing and daily oral dosing by gavage for at least 2 weeks.

The acute blood pressure lowering effects of compounds were assessed in adult male SEIRs. The DSI data acquisition system was used to record minute by minute mean, systolic, and diastolic blood pressure, pulse pressure, heart rate, respiratory rate and activity for 24 hours/day. Groups of 5-6 rats were randomized to receive vehicle or compound at different doses; BP data were recorded 24 h before & 72 h after oral gavage of vehicle or selected compounds. Rats were allowed to recover from any given treatment for 7-14 days before being randomized to receive vehicle or drug once again. Rats were reused until the battery life of the C40 device was exhausted (4-5 months).

TABLE 2

$IC_{50}$ [nM] for human sEH enzyme inhibition

| Compound | $IC_{50}$ |
|---|---|
| 1 | 2 |
| 2 | <1 |
| 3 | 5 |
| 4 | 5 |
| 5 | <1 |
| 6 | 8 |
| 7 | <1 |
| 8 | 6 |
| 9 | <1 |

TABLE 2-continued

IC₅₀ [nM] for human sEH enzyme inhibition

| Compound | IC₅₀ |
|---|---|
| 10 | 3 |
| 11 | 3 |
| 12 | 341 |
| 13 | 59 |
| 14 | 2 |
| 15 | 5 |
| 16 | 6 |
| 17 | 2 |
| 18 | 5 |
| 19 | <1 |

TABLE 2-continued
IC₅₀ [nM] for human sEH enzyme inhibition
| Compound | IC₅₀ |
|---|---|
| 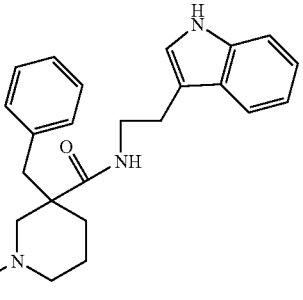 20 | <1 |
| 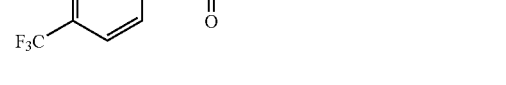 21 | 3 |
| 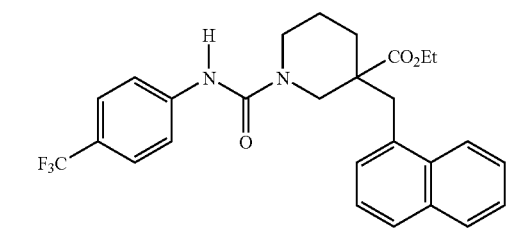 22 | 3 |
| 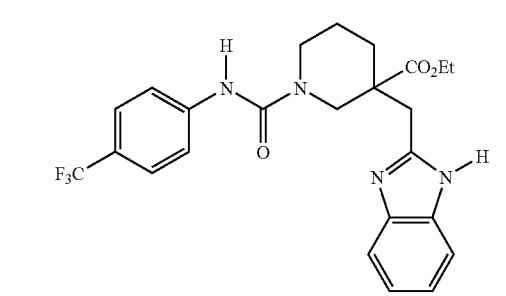 23 | 2 |
| 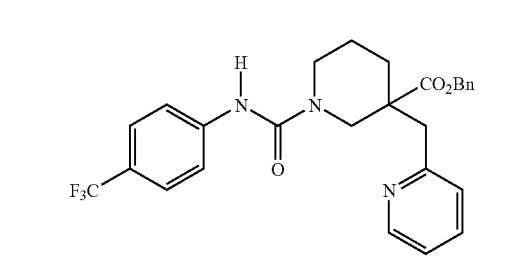 24 | 7 |
| 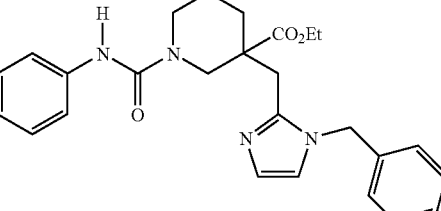 25 | 3 |
| 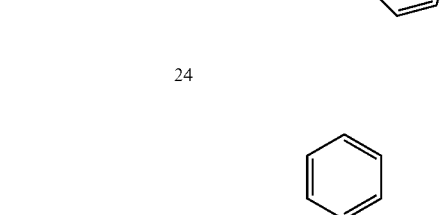 26 | 28 |
| 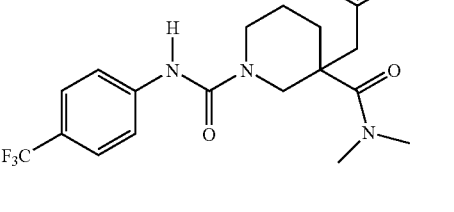 27 | 1 |
| 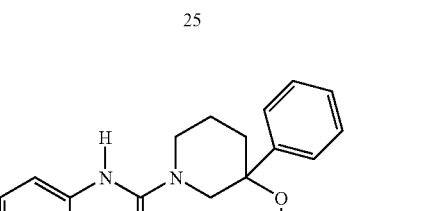 28 | 7 |

TABLE 2-continued
IC₅₀ [nM] for human sEH enzyme inhibition
| Compound | IC₅₀ |
|---|---|
| 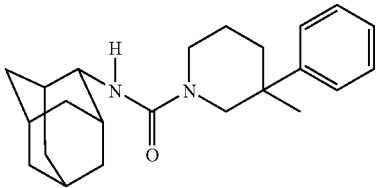 29 | 10 |
| 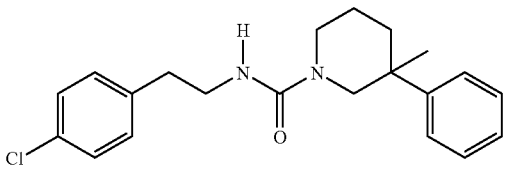 30 | <1 |
| 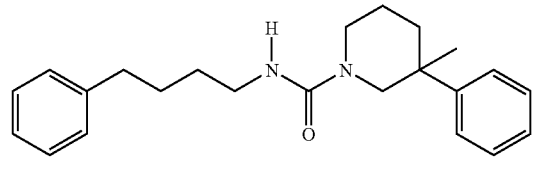 31 | 1 |
| 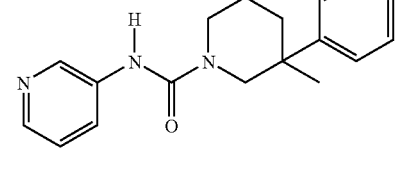 32 | 306 |
| 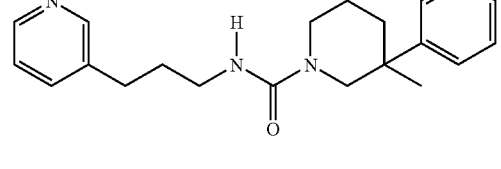 33 | 6 |
| 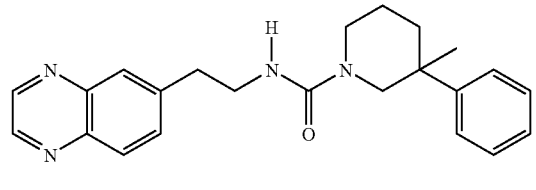 34 | 5 |
| 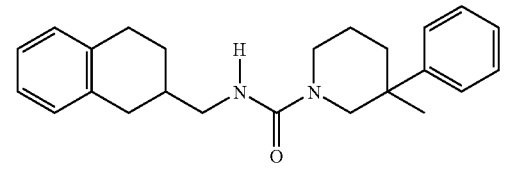 35 | 2 |
| 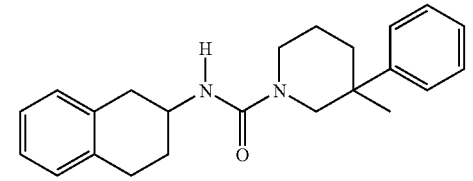 36 | 1 |
| 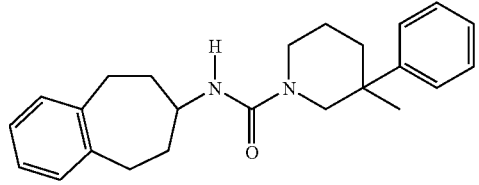 37 | 2 |
| 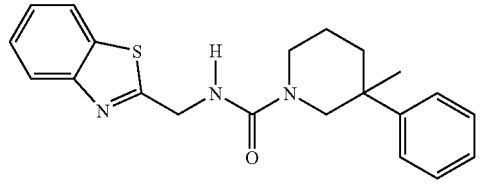 38 | 30 |
| 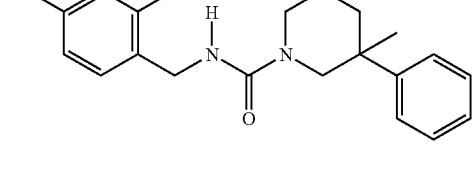 39 | <1 |
| 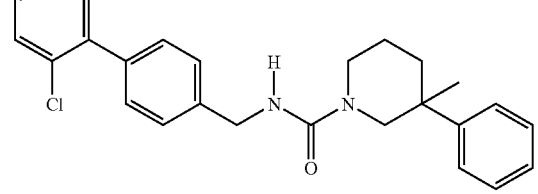 40 | 6 |

TABLE 2-continued

IC$_{50}$ [nM] for human sEH enzyme inhibition

| Compound | IC$_{50}$ |
|---|---|
| 41 | 1.5 |
| 42 | 7 |
| 43 | 6 |
| 44 | 3 |
| 45 | 5 |
| 46 | 3 |
| 47 | 5 |
| 48 | 1 |
| 49 | 5 |

TABLE 2-continued

IC$_{50}$ [nM] for human sEH enzyme inhibition

| Compound | IC$_{50}$ |
|---|---|
| 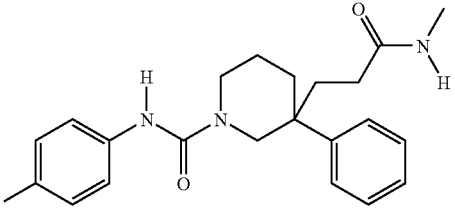 50 | 5 |
| 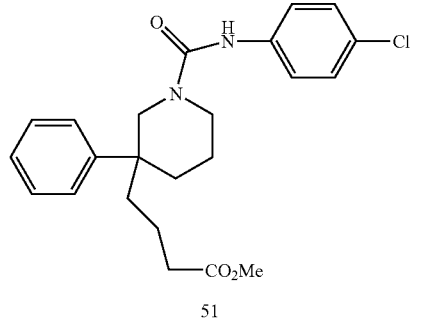 51 | <1 |
| 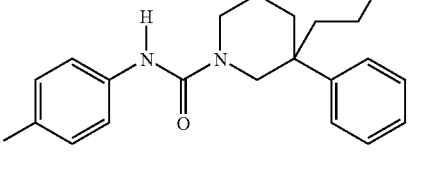 52 | 12 |

All patents, patent applications and publications that are cited herein are hereby incorporated by reference in their entirety. While certain preferred embodiments have been described herein in detail, numerous alternative embodiments are seen as falling within the scope of the invention.

What is claimed is:

1. A compound represented by formula I:

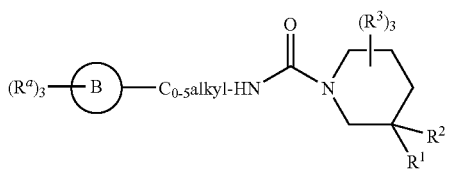

I or a pharmaceutically acceptable salt thereof wherein:
ring B is selected from the group consisting of: phenyl, pyridyl, pyrazolyl, thiadiazolyl, benzisoxazolyl, benzthiazolyl; benzopyrazinyl; pyrimidinyl, thiazolyl, oxadiazolyl, triazolyl, tetrazolyl and tetrahydronaphthyl;

each $R^a$ is defined as follows:
a) each $R^a$ is H or halo, or
b) 1-2 $R^a$ groups represent H or halo,
0-1 $R^a$ represents Aryl, HAR or Hetcy, each of which being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;
and any remaining $R^a$ groups are selected from the group consisting of: $C_{1-3}$alkyl, $OC_{1-3}$alkyl, halo$C_{1-3}$ alkyl, Ohalo$C_{1-3}$alkyl, $S(O)_xC_{1-3}$alkyl, $S(O)_x$-halo$C_{1-3}$alkyl, $S(O)_x$Aryl wherein x is 0, 1 or 2, $CO_2R^b$ and $C_{1-3}$alkyl-$CO_2R^b$, wherein $R^b$ is H, $C_{1-4}$alkyl, halo$C_{1-4}$alkyl, Aryl, HAR or Hetcy;
$R^1$ is selected from the group consisting of:
a) $CO_2R^d$ in which $R^d$ represents H, $C_{1-3}$alkyl-$R^e$, Aryl, HAR or Hetcy, wherein $R^e$ is selected from the group consisting of: H, $OC_{1-3}$alkyl, halo, Ohalo$C_{1-3}$alkyl, $S(O)_x C_{1-3}$alkyl, $S(O)_x$halo$C_{1-3}$alkyl, Aryl, HAR, Hetcy, $S(O)_x$-Aryl and $CO_2R^b$;
b) halo or CN;
c) $C_{1-6}$alkyl or $OC_{1-6}$alkyl, each optionally substituted with up to 3 halo groups, and a member selected from the group consisting of:
i) CN, $C(O)NH_2$, $C(O)NHCH_3$ or $C(O)N(CH_3)_2$;
ii) $CO_2R^d$ with $R^d$ as previously defined in a) above;
iii) OH, $OC_{1-3}$alkyl, haloO$C_{1-3}$alkyl, $NH_2$, $NHCH_3$ or $N(CH_3)_2$; and
iv) Aryl or HAR, each being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl; and
d) Aryl or HAR, each optionally substituted with 1-2 halo, $C_{1-3}$alkyl, halo$C_{1-3}$alkyl, $OC_{1-3}$alkyl, Ohalo$C_{1-3}$alkyl or Aryl($R^a$)$_3$ groups and 0-1 members selected from the group consisting of: CN, HAR($R^a$)$_3$, $CO_2C_{1-6}$alkyl, $CO_2H$, $C(O)N(R^f)_2$, $NHC(O)N(R^f)_2$ and $NHC(O)OR^g$ wherein each $R^f$ is H or $C_{1-6}$alkyl and each $R^g$ represents $C_{1-3}$alkyl, halo$C_{1-3}$alkyl, Aryl, HAR or Hetcy;
$R^2$ is selected from the group consisting of: —(CR$^h_2$)$_{0-2}$—Y—(CR$^h_2$)$_{0-2}$-Aryl($R^a$)$_3$, and —(CR$^h_2$)$_{0-2}$—Y—(CR$^h_2$)$_{0-2}$—HAR($R^a$)$_3$,
wherein Y represents a bond, $CH_2$, O, $S(O)_x$, $C(O)NR^f$, $NR^fC(O)$, $C(O)$ or $NR^fC(O)O$; x, and $R^f$ are as previously defined and $R^h$ represents a member selected from the group consisting of: H, $C_{1-3}$alkyl, $OC_{1-3}$ alkyl and halo;
and each $R^3$ is selected from the group consisting of: H, halo, $C_{1-3}$alkyl, $OC_{1-3}$alkyl, halo$C_{1-3}$alkyl and Ohalo$C_{1-3}$alkyl, or one $R^3$ group is selected from d) above, and the other two $R^3$ groups represent H, halo, $C_{1-3}$alkyl, $OC_{1-3}$alkyl, halo$C_{1-3}$alkyl, Ohalo$C_{1-3}$ alkyl, $CO_2R^b$ or $C(O)NHR^b$.

2. A compound in accordance with claim 1 wherein: $C_{0-5}$alkyl is selected from: a direct bond; —$CH_2$—; —$(CH_2)_2$—; —$(CH_2)_3$—; —$(CH_2)_4$—;

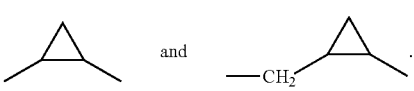

3. A compound in accordance with claim 1 wherein: each $R^a$ is defined as follows:

a) each $R^a$ is H or halo which is F or Cl, or
b) 1-2 $R^a$ groups represent H or halo which is F or Cl,
0-1 $R^a$ represents phenyl, or a 5-10 membered heteroaryl group having 1-2 N atoms, each of which being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;
and any remaining $R^a$ groups are selected from the group consisting of: $C_{1-3}$alkyl, $OC_{1-3}$alkyl, halo$C_{1-3}$alkyl and Ohalo$C_{1-3}$alkyl.

4. A compound in accordance with claim 1 wherein:
$R^1$ is selected from the group consisting of:
a) $CO_2R^d$ in which $R^d$ represents H or $C_{1-3}$alkyl-$R^e$, wherein $R^e$ represents H or Aryl;
b) CN or halo, which is F or Cl;
c) $C_{1-6}$alkyl or $OC_{1-6}$alkyl, each optionally substituted with up to 3 halo groups selected from Cl and F, and a member selected from the group consisting of:
i) CN, $C(O)NH_2$, or $C(O)NHCH_3$;
ii) $CO_2R^d$ with $R^d$ as previously defined in a) above;
iii) $OC_{1-3}$alkyl or Ohalo$C_{1-3}$alkyl, in which the halo atoms are selected from Cl and F; and
iv) phenyl, or a 5-10 membered mono or bicyclic ring system with 1-4 heteroatoms selected from O, S and N, 0-1 of which are O or S, and 0-4 of which are N,
said phenyl and 5-10 membered mono or bicyclic ring system each being optionally substituted with 1-2 halo atoms selected from F and Cl, $C_{1-2}$alkyl or halo$C_{1-2}$alkyl groups, in which the halo atoms are selected from F and Cl, and 0-1 members selected from —$C_{1-3}$alkyl-Aryl and —$CO_2$—$C_{1-6}$alkyl; and
d) Aryl or HAR, each optionally substituted with 1-2 halo atoms selected from F and Cl, $C_{1-2}$alkyl, halo$C_{1-2}$alkyl, $OC_{1-2}$alkyl, Ohalo$C_{1-2}$alkyl, the halo atoms contained in haloalkyl and Ohaloalkyl being selected from F and Cl, and Aryl($R^a$)$_3$ in which the Aryl portion is phenyl,
and 0-1 members selected from the group consisting of: CN, HAR($R^a$)$_3$, $CO_2C_{1-4}$alkyl, $CO_2H$ and $C(O)N(R^f)_2$, wherein each $R^f$ is H or $C_{1-6}$alkyl.

5. A compound in accordance with claim 1 wherein $R^2$ is selected from the group consisting of:
—$(CR^h_2)_{0-1}$—Y—$(CR^h_2)_{0-2}$-Aryl($R^a$)$_3$, and —$(CR^h_2)_{0-1}$—Y—$(CR^h_2)_{0-2}$-HAR($R^a$)$_3$, in which Aryl represents phenyl or naphthyl, and HAR represents a 5-10 membered mono or bicyclic aromatic ring system containing 1-4 heteroatoms from 0, S and N, 0-1 of which are O or S, and 1-4 of which are N;
Y represents a bond, $CH_2$, O, $C(O)NR^f$, $NR^fC(O)$ or $NR^fC(O)O$; and $R^h$ represents a member selected from the group consisting of: H, $CH_3$ and F.

6. A compound in accordance with claim 1 wherein each $R^3$ is selected from the group consisting of: H, F, $CH_3$, $OCH_3$, $CF_3$ and $OCF_3$.

7. A compound in accordance with claim 1 wherein ring B is selected from the group consisting of: phenyl, pyridyl, pyrazolyl, thiadiazolyl, benzthiazolyl, pyrimidinyl, thiazolyl, oxadiazolyl, triazolyl, tetrazolyl and tetrahydronaphthyl.

8. A compound in accordance with claim 7 wherein ring B is selected from the group consisting of: phenyl, pyridyl, pyrazolyl, and thiadiazolyl.

9. A compound in accordance with claim 8 wherein ring B represents phenyl.

10. A compound in accordance with claim 2 wherein $C_{0-5}$ alkyl represents a member selected from the group consisting of: a bond, —$CH_2$—, —$CH_2CH_2$—, —$CH_2CH_2CH_2$—,

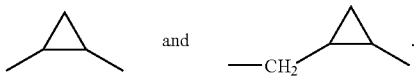

11. A compound in accordance with claim 10 wherein $C_{0-5}$ alkyl represents a member selected from the group consisting of: a bond, —$CH_2$—, —$CH_2CH_2$—, —$CH_2CH_2CH_2$— and

12. A compound in accordance with claim 3 wherein: one $R^a$ represents H;
another $R^a$ is selected from the group consisting of: H and Cl, and the third $R^a$ is selected from the group consisting of H, Cl, phenyl, pyridyl, indolyl, isoquinolinyl, and benzopyrazolyl, $CH_3$, $OCH_3$, $CF_3$, $SCF_3$ and $OCF_3$.

13. A compound in accordance with claim 12 wherein: two $R^a$ groups represents H;
and the third $R^a$ is selected from the group consisting of H, Cl, phenyl, pyridyl, $CH_3$, $OCH_3$, $CF_3$, $SCF_3$ and $OCF_3$.

14. A compound in accordance with claim 4 wherein:
$R^1$ is selected from the group consisting of:
a) $CO_2R^d$ in which $R^d$ represents H or $CH_2$—$R^e$, wherein $R^e$ represents H, $CH_3$, or phenyl;
b) F, Cl or CN;
c) $C_{1-3}$alkyl or $OC_{1-3}$alkyl, each optionally substituted with up to 3 fluorine atoms, and a member selected from the group consisting of:
i) CN or $C(O)NH_2$;
ii) $CO_2R^d$ with $R^d$ as previously defined in a) above; and
iii) Phenyl or HAR, which is a 5-10 membered mono or bicyclic ring system with 1-4 heteroatoms selected from 0, S and N, 0-1 of which are O or S, and 0-4 of which are N,
said Aryl and HAR each being optionally substituted with 1-2 halo atoms selected from F and Cl, $C_{1-2}$alkyl or halo$C_{1-2}$alkyl groups, in which the halo atoms are selected from F and Cl, and 0-1 members selected from —$C_{1-3}$alkyl-Aryl and —$CO_2$—$C_{1-6}$alkyl; and
d) Phenyl or HAR containing 5-10 atoms, 1-4 of which are heteroatoms, 0-1 being selected from O and S, and 1-4 of which are N atoms, said Phenyl and HAR being optionally substituted with 1-2 halo atoms selected from F and Cl, $C_{1-2}$alkyl, halo$C_{1-2}$alkyl, $OC_{1-2}$alkyl, Ohalo$C_{1-2}$alkyl, the halo atoms contained in haloalkyl and Ohaloalkyl being selected from F and Cl, and Phenyl($R^a$)$_3$,
and 0-1 members selected from the group consisting of: CN, HAR($R^a$)$_3$, $CO_2C_{1-4}$alkyl, $CO_2H$ and $C(O)N(R^f)_2$, wherein each $R^f$ is H or $C_{1-6}$alkyl.

15. A compound in accordance with claim 5 wherein:
$R^2$ is selected from the group consisting of:
—$(CR^h_2)_{0-1}$—Y—$(CR^h_2)_{0-2}$-Aryl($R^a$)$_3$, and —$(CR^h_2)_{0-1}$—Y—$(CR^h_2)_{0-2}$-HAR($R^a$)$_3$, in which Aryl represents phenyl or naphthyl, and HAR represents a 5-9 membered mono or bicyclic aromatic ring system containing 1-4 heteroatoms selected from 0, S and N, 0-1 of which are O or S, and 1-4 of which are N;
Y represents a bond, $CH_2$, O, $C(O)NR^f$, $NR^fC(O)$, or $NR^fC(O)O$; and each $R^h$ represents a hydrogen atom.

16. A compound in accordance with claim 6 wherein:
each $R^3$ is selected from the group consisting of: H, F and $CH_3$.

17. A compound of the formula:

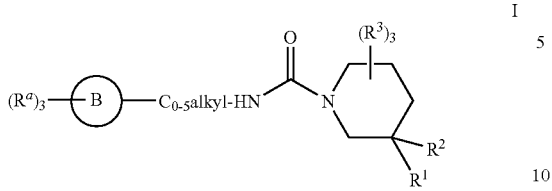

or a pharmaceutically acceptable salt thereof wherein:
ring B represents: a) phenyl; b) HAR which is selected from the group consisting of: pyridyl, pyrazolyl, thiadiazolyl, benzisoxazolyl, benzthiazolyl, pyrimidinyl, thiazolyl, oxadiazolyl, triazolyl, tetrazolyl and benzopyrazinyl; c) $C_{10}$-bicycloalkyl or d) $C_{6-7}$cycloalkyl fused to phenyl;
—$C_{0-5}$alkyl is selected from: a direct bond; —$CH_2$—; —$(CH_2)_2$—; —$(CH_2)_3$—; —$(CH_2)_4$—;

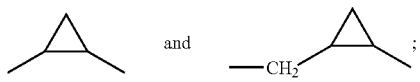

each $R^a$ is defined as follows:
a) each $R^a$ is H or halo which is F or Cl, or
b) 1-2 $R^a$ groups represent H or halo which is F or Cl, 0-1 $R^a$ represents phenyl, or a 5-10 membered heteroaryl group having 1-2 N atoms, each of which being optionally substituted with 1-3 halo, $C_{1-3}$alkyl or halo$C_{1-3}$alkyl groups, and 0-1 members selected from —$C_{1-3}$alkyl-Aryl and —$CO_2$—$C_{1-6}$alkyl;
and any remaining $R^a$ groups are selected from the group consisting of: $C_{1-3}$alkyl, $OC_{1-3}$alkyl, halo $C_{1-3}$alkyl and Ohalo$C_{1-3}$alkyl;
$R^1$ is selected from the group consisting of:
a) $CO_2R^d$ in which $R^d$ represents H or $C_{1-3}$alkyl-$R^e$, wherein $R^e$ represents H or Aryl;
b) halo, which is F or Cl, or CN;
c) $C_{1-6}$alkyl or $OC_{1-6}$alkyl, each optionally substituted with up to 3 halo groups selected from Cl and F, and a member selected from the group consisting of:
i) CN, $C(O)NH_2$, or $C(O)NHCH_3$;
ii) $CO_2R^d$ with $R^d$ as previously defined in a) above;
iii) $OC_{1-3}$alkyl or Ohalo$C_{1-3}$alkyl, in which the halo atoms are selected from Cl and F; and
iv) phenyl, or a 5-10 membered mono or bicyclic ring system with 1-4 heteroatoms selected from 0, S and N, 0-1 of which are O or S, and 0-4 of which are N, said phenyl or 5-10 membered mono or bicyclic ring system each being optionally substituted with 1-2 halo atoms selected from F and Cl, $C_{1-2}$alkyl or halo$C_{1-2}$alkyl groups, in which the halo atoms are selected from F and Cl, and 0-1 members selected from —$C_{1-3}$alkyl-Aryl and —$CO_2$—$C_{1-6}$alkyl; and
d) Aryl or HAR, each optionally substituted with 1-2 halo atoms selected from F and C, $C_{1-2}$alkyl, halo $C_{1-2}$alkyl, $OC_{1-2}$alkyl, Ohalo$C_{1-2}$alkyl, the halo atoms contained in haloalkyl and Ohaloalkyl being selected from F and Cl, and Aryl($R^a$)$_3$ in which the Aryl portion is phenyl, and 0-1 members selected from the group consisting of: CN, HAR($R^a$)$_3$, $CO_2C_{1-4}$alkyl, $CO_2H$ and $C(O)N(R^f)_2$, wherein each $R^f$ is H or $C_{1-6}$alkyl;
$R^2$ is selected from the group consisting of: —$(CR^h_2)_{0-1}$—Y—$(CR^h_2)_{0-2}$-Aryl($R^a$)$_3$, and —$(CR^h_2)_{0-1}$—Y—$(CR^h_2)_{0-2}$-HAR($R^a$)$_3$, in which Aryl represents phenyl or naphthyl, and HAR represents a 5-10 membered mono or bicyclic aromatic ring system containing 1-4 heteroatoms selected from 0, S and N, 0-1 of which are O or S, and 1-4 of which are N;
Y represents a bond, $CH_2$, O, $C(O)NR^f$, $NR^fC(O)$ or $NR^fC(O)O$; and $R^h$ represents a member selected from the group consisting of: H, $CH_3$ and F;
and
each $R^3$ is selected form the group consisting of: H, F, $CH_3$, $OCH_3$, $CF_3$ and $OCF_3$.

18. A compound of formula I:

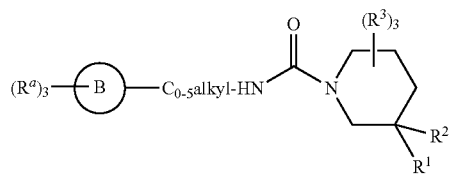

or a pharmaceutically acceptable salt or solvate thereof wherein:
ring B is selected from the group consisting of: phenyl; pyridyl, pyrazolyl, thiadiazolyl, benzisoxazolyl, benzthiazolyl, benzopyrazinyl, pyrimidinyl, thiazolyl, oxadiazolyl, triazolyl, tetrazolyl and tetrahydronaphthyl;
$C_{0-5}$ alkyl represents a member selected from the group consisting of: a bond, —$CH_2$—, —$CH_2CH_2$—, —$CH_2CH_2CH_2$—, and

one $R^a$ represents H;
another $R^a$ is selected from the group consisting of: H and Cl, and the third $R^a$ is selected from the group consisting of H, Cl, phenyl, pyridyl, indolyl, isoquinolinyl, and benzopyrazolyl, $CH_3$, $OCH_3$, $CF_3$ and $OCF_3$;
$R^1$ is selected from the group consisting of:
a) $CO_2R^d$ in which $R^d$ represents H or $CH_2$—$R^e$, wherein $R^e$ represents H or methyl;
b) For CN;
c) $C_{1-3}$alkyl or $OC_{1-3}$alkyl, each optionally substituted with up to 3 fluorine atoms, and a member selected from the group consisting of:
i) CN or $C(O)NH_2$;
ii) $CO_2R^d$ with $R^d$ as previously defined in a) above; and
iii) Phenyl or HAR, which is a 5-10 membered mono or bicyclic ring system with 1-4 heteroatoms selected from 0, S and N, 0-1 of which are O or S, and 0-4 of which are N,
said Phenyl and HAR each being optionally substituted with 1-2 halo atoms selected from F and Cl, $C_{1-2}$alkyl or halo$C_{1-2}$alkyl groups, in which the halo atoms are F atoms, and 0-1 members selected from —C$_{1-3}$alkyl-Aryl and —CO$_2$—C$_{1-6}$alkyl; and d) Phenyl or HAR containing 5-10 atoms, 1-4 of which are heteroatoms, 0-1 being selected from O and S, and 1-4 of which are N atoms, said Phenyl and HAR being optionally substituted with 1-2 halo atoms selected from F and Cl, C$_{1-2}$alkyl, haloC$_{1-2}$alkyl, OC$_{1-2}$alkyl, OhaloC$_{1-2}$alkyl, the halo atoms contained in haloalkyl and Ohaloalkyl being selected from F and Cl, and Phenyl(R$^a$)$_3$, and 0-1 members selected from the group consisting of: CN, HAR(R$^a$)$_3$, CO$_2$C$_{1-4}$alkyl, CO$_2$H and C(O)N(R$^f$)$_2$, wherein each R$^f$ is H or C$_{1-6}$alkyl;

R$^2$ is selected from the group consisting of:
—(CR$^h_2$)$_{0-1}$—Y—(CR$^h_2$)$_{0-2}$-Aryl(R$^a$)$_3$, and —(CR$^h_2$)$_{0-1}$—Y—(CR$^h_2$)$_{0-2}$-HAR(R$^a$)$_3$, in which Aryl represents phenyl or naphthyl, and HAR represents a 5-10 membered mono or bicyclic aromatic ring system containing 1-4 heteroatoms selected from O, S and N, 0-1 of which are O or S, and 1-4 of which are N;

Y represents a bond, CH$_2$, O, C(O)NR$^f$, NR$^f$C(O) or NR$^f$C(O)O; and each R$^h$ represents a hydrogen atom, and each R$^3$ is selected from the group consisting of: H, F and CH$_3$.

19. A compound selected from Table I:

TABLE 1

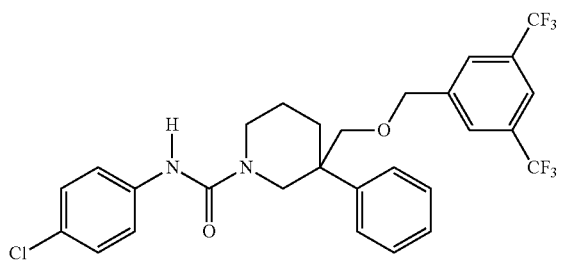

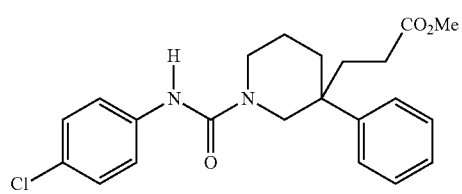

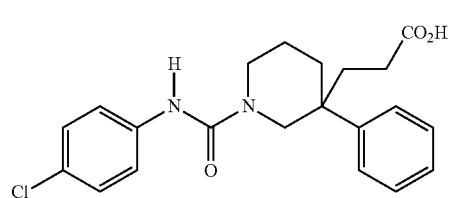

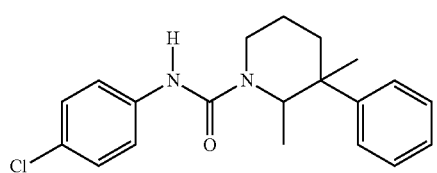

TABLE 1-continued

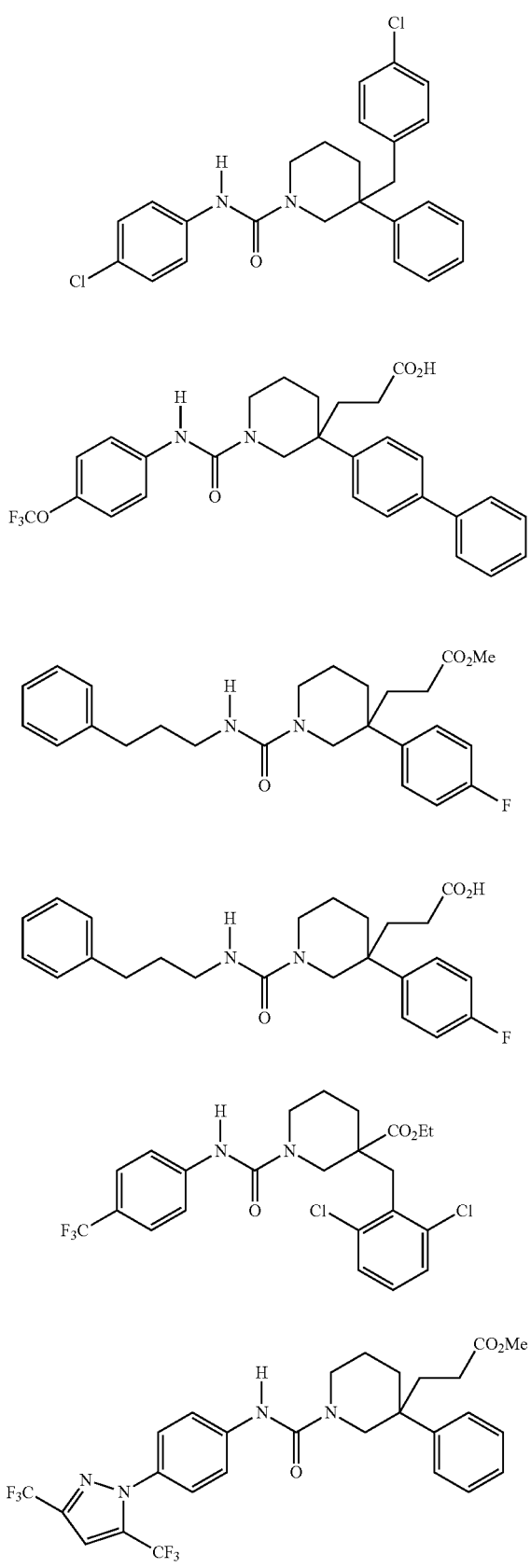

TABLE 1-continued
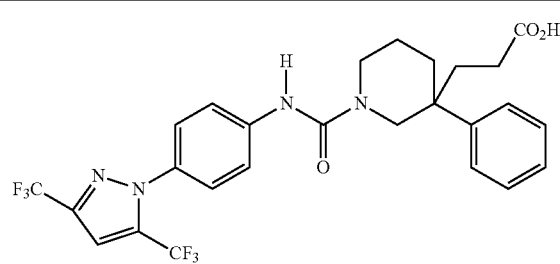
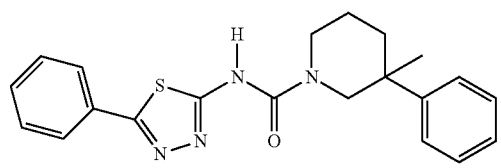
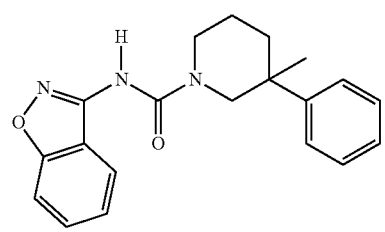
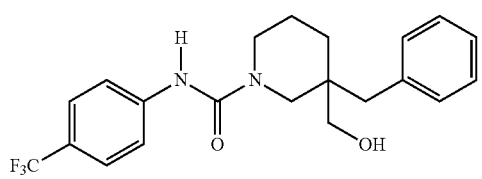
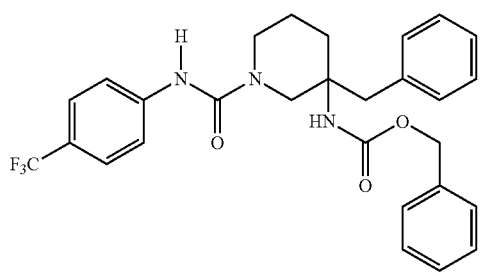
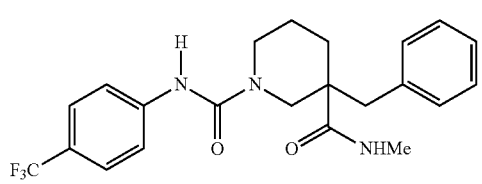
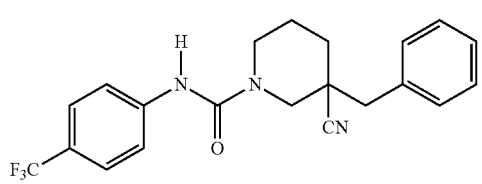
TABLE 1-continued
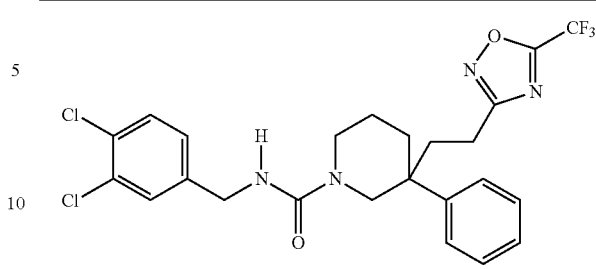
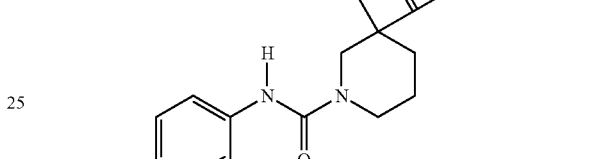
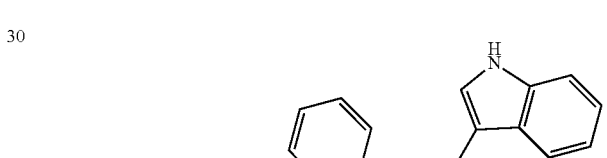
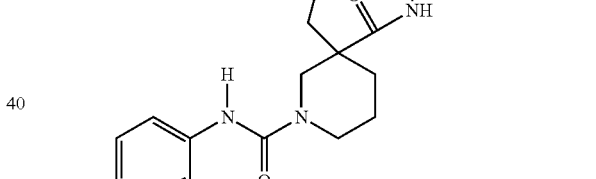
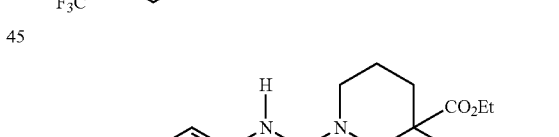
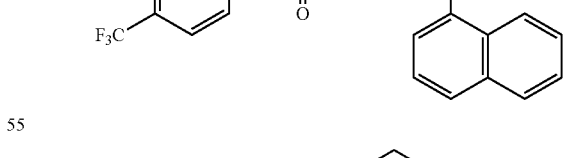
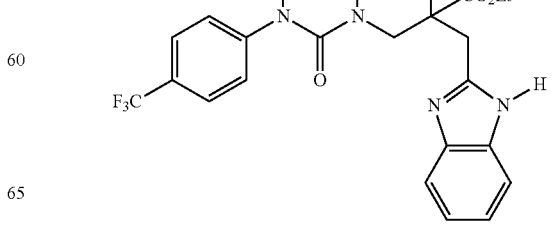

TABLE 1-continued
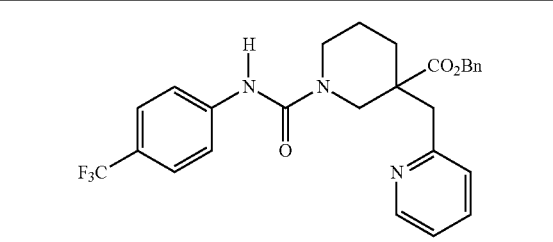
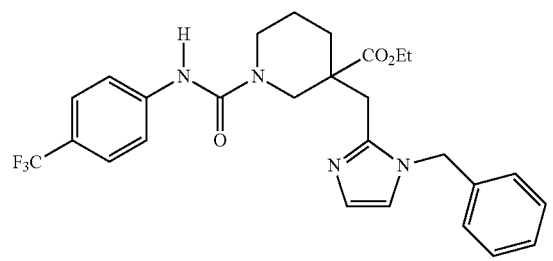
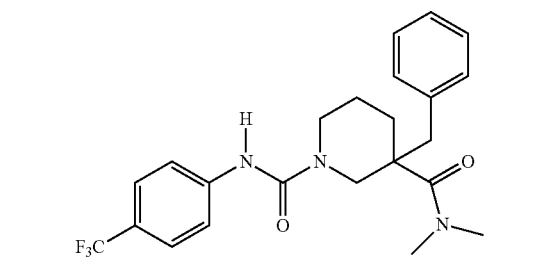
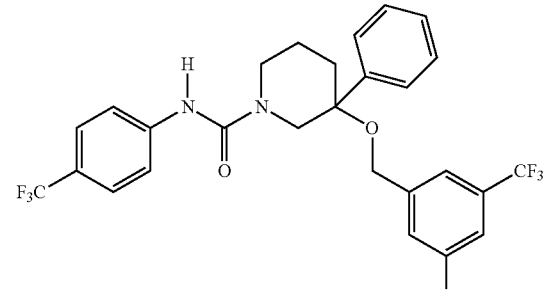
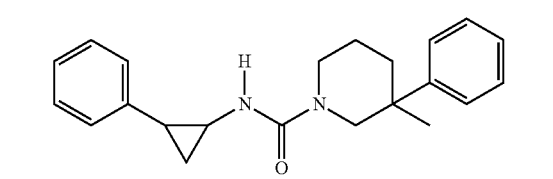
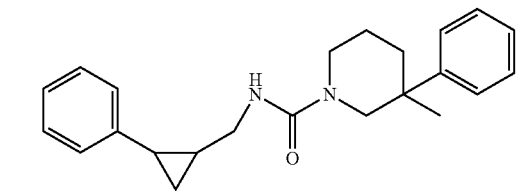
TABLE 1-continued
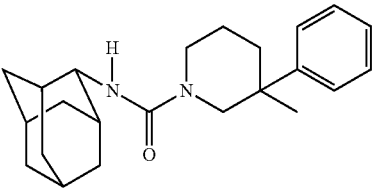
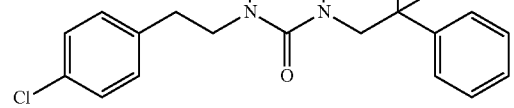
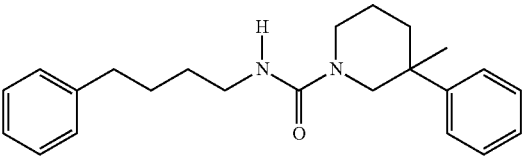
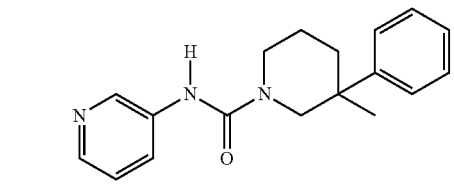
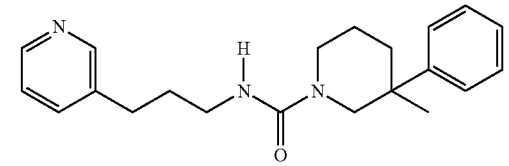
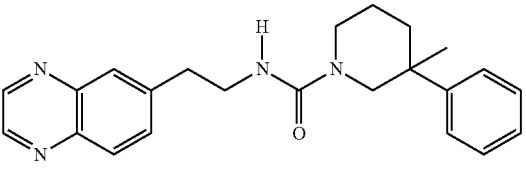
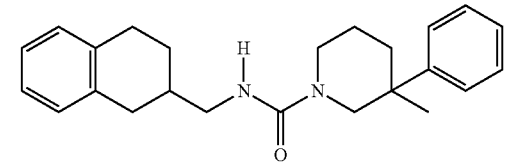
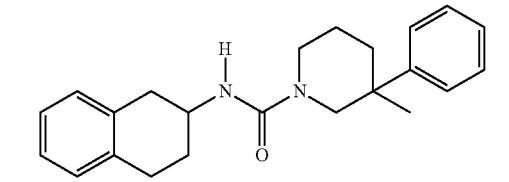

TABLE 1-continued
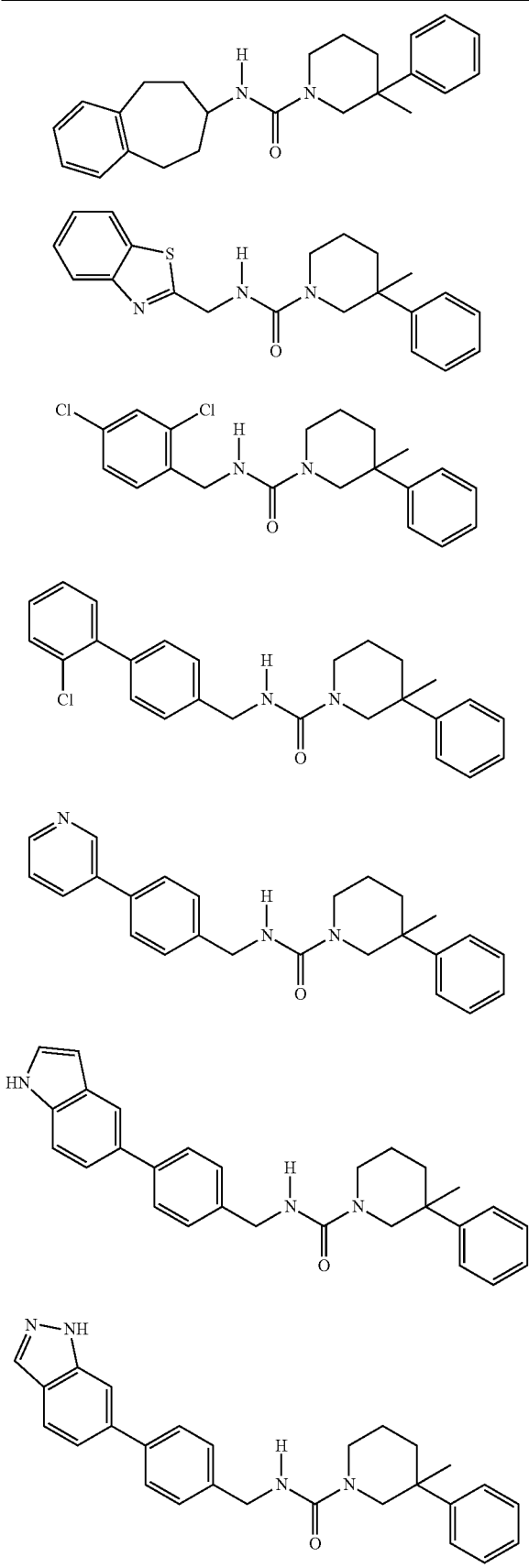
TABLE 1-continued
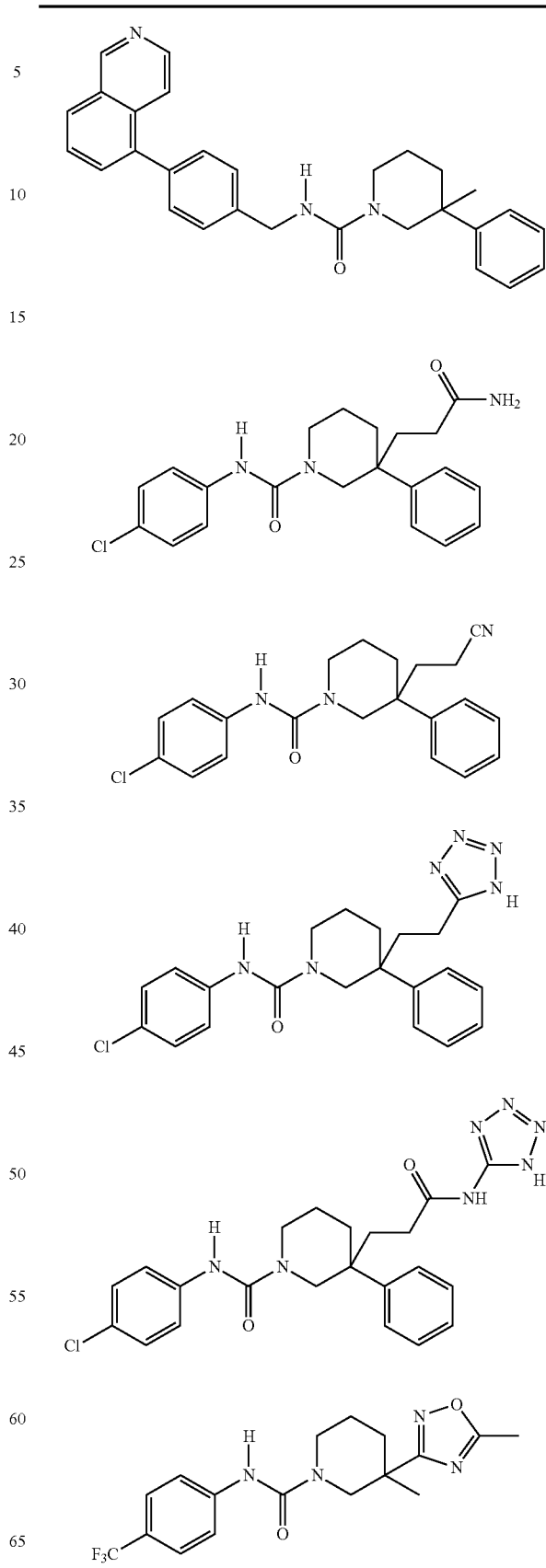

TABLE 1-continued

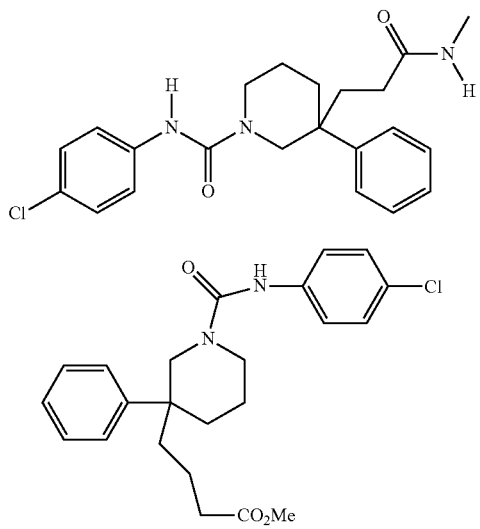

TABLE 1-continued

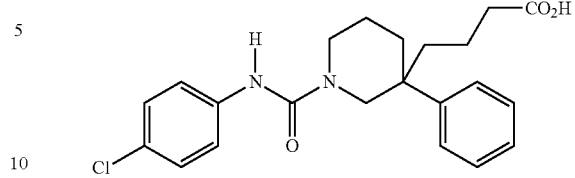

or a pharmaceutically acceptable salt thereof.

20. A pharmaceutical composition comprised of a compound in accordance with claim 1 in combination with a pharmaceutically acceptable carrier.

21. A method of treating type 2 diabetes in a mammalian patient in need of such treatment comprising administering to the patient a compound in accordance with claim 1 in an amount that is effective for treating type 2 diabetes.

* * * * *